United States Patent
Barrangou et al.

(10) Patent No.: US 11,542,466 B2
(45) Date of Patent: Jan. 3, 2023

(54) METHODS AND COMPOSITIONS FOR DELIVERY OF CRISPR BASED ANTIMICROBIALS

(71) Applicant: NORTH CAROLINA STATE UNIVERSITY, Raleigh, NC (US)

(72) Inventors: Rodolphe Barrangou, Raleigh, NC (US); Jan-Peter van Pijkeren, Madison, WI (US)

(73) Assignee: NORTH CAROLINA STATE UNIVERSITY, Raleigh, NC (US)

( * ) Notice: Subject to any disclaimer, the term of this patent is extended or adjusted under 35 U.S.C. 154(b) by 263 days.

(21) Appl. No.: 16/063,409

(22) PCT Filed: Dec. 20, 2016

(86) PCT No.: PCT/US2016/067657
§ 371 (c)(1),
(2) Date: Jun. 18, 2018

(87) PCT Pub. No.: WO2017/112620
PCT Pub. Date: Jun. 29, 2017

(65) Prior Publication Data
US 2018/0371405 A1 Dec. 27, 2018

Related U.S. Application Data

(60) Provisional application No. 62/271,114, filed on Dec. 22, 2015, provisional application No. 62/275,421, filed on Jan. 6, 2016.

(51) Int. Cl.
| | | |
|---|---|---|
| C12N 1/20 | (2006.01) | |
| A61P 31/04 | (2006.01) | |
| C12N 7/00 | (2006.01) | |
| C12N 9/22 | (2006.01) | |
| C12N 15/11 | (2006.01) | |
| C12N 15/113 | (2010.01) | |
| C12N 15/74 | (2006.01) | |
| A61K 35/74 | (2015.01) | |
| C12N 15/70 | (2006.01) | |

(52) U.S. Cl.
CPC ............ *C12N 1/20* (2013.01); *A61P 31/04* (2018.01); *C12N 7/00* (2013.01); *C12N 9/22* (2013.01); *C12N 15/11* (2013.01); *C12N 15/113* (2013.01); *C12N 15/74* (2013.01); *A61K 35/74* (2013.01); *C12N 15/70* (2013.01); *C12N 2310/20* (2017.05); *C12N 2320/32* (2013.01); *C12N 2795/00011* (2013.01); *C12N 2795/10322* (2013.01); *C12N 2795/10343* (2013.01); *C12N 2795/10351* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 8,697,359 B1 | 4/2014 | Zhang | |
| 9,023,649 B2 | 5/2015 | Mali et al. | |
| 9,260,723 B2 | 2/2016 | Mali et al. | |
| 10,506,812 B2 * | 12/2019 | Clube | A61K 45/06 |
| 2009/0007301 A1 | 1/2009 | Wintz et al. | |
| 2013/0288251 A1 | 10/2013 | Horvath et al. | |
| 2014/0068797 A1 | 3/2014 | Doudna et al. | |
| 2014/0113376 A1 | 4/2014 | Sorek et al. | |
| 2014/0186958 A1 | 7/2014 | Zhang et al. | |
| 2014/0273233 A1 | 9/2014 | Chen et al. | |
| 2014/0356867 A1 | 12/2014 | Peter et al. | |
| 2014/0356956 A1 | 12/2014 | Church et al. | |
| 2015/0050699 A1 | 2/2015 | Siksnys et al. | |
| 2015/0064138 A1 * | 3/2015 | Lu | C12N 9/22 424/93.2 |
| 2015/0093473 A1 | 4/2015 | Barrangou et al. | |
| 2015/0098954 A1 | 4/2015 | Hyde et al. | |
| 2015/0132263 A1 | 5/2015 | Liu et al. | |
| 2015/0291961 A1 | 10/2015 | Siksnys et al. | |
| 2015/0315576 A1 | 11/2015 | Caliando et al. | |
| 2015/0353901 A1 | 12/2015 | Liu et al. | |
| 2016/0017366 A1 | 1/2016 | Chen et al. | |
| 2016/0024510 A1 | 1/2016 | Bikard et al. | |
| 2016/0186213 A1 | 6/2016 | Zhang et al. | |
| 2016/0289700 A1 | 10/2016 | Barrangou et al. | |
| 2016/0298096 A1 | 10/2016 | Charpentier et al. | |
| 2016/0333348 A1 | 11/2016 | Clube et al. | |
| 2017/0002339 A1 | 1/2017 | Barrangou et al. | |
| 2017/0028083 A1 | 2/2017 | Beisel et al. | |
| 2017/0073663 A1 * | 3/2017 | Wang | C12N 15/01 |
| 2017/0196225 A1 | 7/2017 | Clube et al. | |
| 2017/0246221 A1 | 8/2017 | Clube et al. | |
| 2017/0275648 A1 | 9/2017 | Barrangou et al. | |
| 2018/0064114 A1 | 3/2018 | Clube | |
| 2018/0064115 A1 | 3/2018 | Clube et al. | |
| 2018/0070594 A1 | 3/2018 | Clube et al. | |
| 2018/0084785 A1 | 3/2018 | Clube | |
| 2018/0084786 A1 | 3/2018 | Clube | |
| 2018/0146681 A1 | 5/2018 | Clube | |
| 2018/0155729 A1 | 6/2018 | Beisel et al. | |
| 2018/0200387 A1 | 7/2018 | Porteus | |
| 2018/0258411 A1 | 9/2018 | Kadiyala et al. | |
| 2018/0273937 A1 | 9/2018 | Beisel et al. | |

FOREIGN PATENT DOCUMENTS

| | | |
|---|---|---|
| EP | 286267 A1 | 4/2015 |
| EP | 2860267 | 4/2015 |

(Continued)

OTHER PUBLICATIONS

Wilson et al. (Wilson, K.; Walker, J. (2010). Principles and Techniques of Biochemistry and Molecular Biology. 7th ed. New York: Cambridge University Press, pp. 214-218).*

(Continued)

*Primary Examiner* — Suzanne M Noakes
*Assistant Examiner* — Jae W Lee
(74) *Attorney, Agent, or Firm* — Myers Bigel, P.A.

(57) ABSTRACT

The invention is directed to antibacterial compositions comprising bacteria modified to comprise phasmids engineered to deliver of CRISPR RNAs and methods for their use.

22 Claims, 9 Drawing Sheets

Specification includes a Sequence Listing.

(56) References Cited

FOREIGN PATENT DOCUMENTS

| | | |
|---|---|---|
| WO | 2006/113709 | 10/2006 |
| WO | WO 2010/054154 | 5/2010 |
| WO | WO 2010/075424 | 7/2010 |
| WO | WO 2013/098244 | 7/2013 |
| WO | 2013/141680 | 9/2013 |
| WO | WO 2013/176772 | 11/2013 |
| WO | WO 2013/188522 | 12/2013 |
| WO | WO 2013/188638 | 12/2013 |
| WO | WO 2014/022702 | 2/2014 |
| WO | WO 2014/065596 | 5/2014 |
| WO | WO 2014/071235 | 5/2014 |
| WO | 2014/093479 | 6/2014 |
| WO | 2014093595 A9 | 6/2014 |
| WO | WO 2014/110006 | 7/2014 |
| WO | WO 2014/113493 | 7/2014 |
| WO | WO 2014/124226 | 8/2014 |
| WO | WO 2014/144155 | 9/2014 |
| WO | WO 2014/144592 | 9/2014 |
| WO | WO 2014/150624 | 9/2014 |
| WO | WO 2014/186686 | 11/2014 |
| WO | 2014/204727 | 12/2014 |
| WO | WO 2014/191128 | 12/2014 |
| WO | WO 2014/191518 | 12/2014 |
| WO | WO 2014/201015 | 12/2014 |
| WO | WO 2014/204727 | 12/2014 |
| WO | WO 2015/021353 | 2/2015 |
| WO | WO 2015/026886 | 2/2015 |
| WO | WO 2015/034872 | 3/2015 |
| WO | WO 2015/035139 | 3/2015 |
| WO | WO 2015/040402 | 3/2015 |
| WO | WO 2015/053995 | 4/2015 |
| WO | WO 2015/070193 | 5/2015 |
| WO | WO 2015/077290 | 5/2015 |
| WO | 2015/089486 | 6/2015 |
| WO | WO 2015/089277 | 6/2015 |
| WO | WO 2015/089406 | 6/2015 |
| WO | 2015112896 A2 | 7/2015 |
| WO | WO 2015/116686 | 8/2015 |
| WO | WO 2015/119941 | 8/2015 |
| WO | WO 2015/139139 | 9/2015 |
| WO | 2015/159068 | 10/2015 |
| WO | WO 2015/148680 | 10/2015 |
| WO | WO 2015/153791 | 10/2015 |
| WO | WO 2015/153889 | 10/2015 |
| WO | WO 2015/153940 | 10/2015 |
| WO | WO 2015/155686 | 10/2015 |
| WO | WO 2015/159086 | 10/2015 |
| WO | WO 2015/159087 | 10/2015 |
| WO | WO 2015/160683 | 10/2015 |
| WO | WO 2015/189693 | 12/2015 |
| WO | WO 2015/200555 | 12/2015 |
| WO | WO 2016/084088 | 6/2016 |
| WO | WO 2016/177682 | 11/2016 |
| WO | 2016/196361 | 12/2016 |
| WO | 2017/027423 | 2/2017 |

OTHER PUBLICATIONS

Citorik et al. (Sequence-specific antimicrobials using efficiently delivered RNA-guided nucleases, Nat Biotechnol 2014, 32:1141-1145).*

Lecuit et al. (Internalin of Listeria monocytogenes withan Intact Leucine-Rich Repeat Region Is Sufficient To Promote Internalization, Infection and Immunity, Dec. 1997, p. 5309-5319 vol. 65, No. 12).*

Milani C et al. Genomic encyclopedia of type strains of the genus Bifidobacterium. Applied and Environmental Microbiology. Oct. 2014; 80(20): 6290-6302.

Database GenBank [online]. NBI, U.S. National Library of Medicine. Aug. 5, 2014. "CRISPER-associated protein, Csn1 family [Bifidobacterium bombi DSM 19703]." XP002785852, retrieved from NCBI accession No. GenBank; KFF31259. Database accession No. KFF31259. 1 page.

Beloglazova et al. "Structure and activity of the Cas3 HD nuclease MJ0384, an effector enzyme of the CRISPR Interference" The EMBO Journal, 30(22):4616-4627 (2011).

Office Action, U.S. Appl. No. 15/032,985, dated Feb. 5, 2019, 11 pages.

Rath D et al. The CRISPR-Cas immune system: Biology, mechanisms and applications. Biochimie. 2015;117:119-128.

Spath K et al. Lactobacillus plantarum and Lactobacillus buchneri as expression systems: Evaluation of different origins of replication for the design of suitable shuttle vectors. Mol. Biotechnol. 2012; 52: 40-48.

Grissa I et al. The CRISPRdb database and tools to display CRISPRs and to generate dictionaries of spacers and repeats. BMC Bioinformatics. 2007; 8(172): pp. 1-10.

Luo et al. "The CRISPR RNA-guided surveillance complex in Escherichia coli accommodates extended RNA Spacers" Nucleic Acids Research, 44(15):7385-7394 2016.

Boudry et al. "Function of CRISPR-Cas System of the Human Pathogen Clostridium difficile" mBio, 6(5):1-15 2015.

Edgar et al. Supplemental Material "The Escherichia coli CRISPR System Protects from Lysogenization, Lysogens, and Prophage induction" Journal of Bacteriology, 192(23): 6292-6294 2010.

Shinkai "Structure and Function of CRISPR-Cas System" Seibutsu Butsuri, 54(5):247-252 (2014) Abstract Only.

Extended European Search Report regarding European Application No. EP19196063, dated Jun. 26, 2020 12 pages.

Third Party Observations corresponding to European Patent Application No. 16804164.8, dated Jul. 24, 2019 60 pages.

Third Party Observations corresponding to European Patent Application No. 16812275.2, dated May 15, 2020 108 pages.

Chauthaiwale, V. M. et al. "Bacteriophage Lamda as a Cloning Vector" Microbiological Reviews, 56(4):577-591 (1992).

Dang, Y. et al. "Optimizing sgRNA structure to improve CRISPR-Cas9 knockout efficiency" Genome Biology, 16(280):1-10 (2015).

Edgar, R. et al. "Reversing Bacterial Resistance to Antibiotics by Phage-Mediated Delivery of Dominant Sensitive Genes" Applied and Environmental Microbiology, 78(3):744-751 (2011).

Extended European Search Report corresponding to European Patent Application No. 18806333.3 (8 pages) (dated Feb. 9, 2021).

Third Party Observation filed in European Patent Application No. 16804164.8 on Feb. 19, 2021, 15 pages.

Third Party Observation filed in European Patent Application No. 16812275.2 on Feb. 19, 2021, 38 pages.

Yosef, I. et al. "Temperate and lytic bacteriophages programmed to sensitize and kill antibiotic-resistant bacteria" PNAS, 112(23):7267-7272 (2015).

Gutierrez et al. "Predicting CRISPR-Cas9 activity in E. coli" bioRxviv, https://doi.org/10.1101/308148, pp. 1-22 2018.

Hochstrassera et al. "CasA mediates Cas3-catalyzed target degradation during CRISPR RNA-guided interference" PNAS, 111(18):6618-23 2014.

Nizet et al. "Bacterial sepsis and meningitis" Remington and Klein's Infectious diseases of the fetus and newborn infant, 8th Edition, pp. 217-271 2011.

Verco et al. "Cytotoxic Chromosomal Targeting by CRISPR/Cas Systems Can Reshape Bacterial Genomes and Expel or Remodel Pathogenicity Islands" PLOS Genetics, 9(4):1-13 2013.

Final Office Action, U.S. Appl. No. 15/302,655, dated Nov. 2, 2018, 21 pp.

International Search Report and Written Opinion, PCT/US2018/034322, dated Sep. 13, 2018, 7 pages.

Final Office Action, U.S. Appl. No. 16/153,052, dated Dec. 26, 2018, 14 pages.

Final Office Action, U.S. Appl. No. 15/507,176, dated Jan. 16, 2019, 19 pages.

Claesson MJ et al. NCBI reference sequence NC_007929, direct submission Dec. 16, 2005, p. 1 (2005).

Written Opinion of the International Search Report regarding International Application No. PCT/US2016/067657, dated Mar. 6, 2017, 9 pages.

Uchiyama Jumpei et al., "Characterization of Helicobacter pylori bacteriophage KHP30", Applied and environmental microbiology, 79(10):3176-3184 (2013).

(56) References Cited

OTHER PUBLICATIONS

Nale Janet Y. et al., "Diverse temperate bacteriophage carriage in Clostridium difficile 027 strains", PLoS One, 7(5) 1-9 (2012).
Cochrane Kyla et al., "Complete genome sequences and analysis of the *Fusobacterium nucleatum* subspecies *animalis* 7-1 bacteriophage PHIFunu1 and PHIFunu2", Anaerobe, 38:125-129 (2016).
Barrangou R. "CRISPR-Cas systems and RNA-guided interference", *Wiley interdisciplinary reviews*, RNA (2013) 4: pp. 267-278.
Barrangou R., et al. "CRISPR: new horizons in phage resistance and strain identification" *Annu Rev Food Sci Technol* (2012) 3, pp. 143-162.
Barrangou R., et al. "CRISPR-Cas systems: prokaryotes upgrade to adaptive immunity", *Mol Cell* (2014) 54(2): pp. 234-244.
Barrangou, R. "Diversity of CRISPR-Cas immune systems and molecular machines", *Genome Biology* (2015) 16:247, 11 pages.
Barrangou, R., et al. "CRISPR provides acquired resistance against viruses in prokaryotes", *Science* (2007) 315(5819): pp. 1709-1712.
Bhaya et al. "CRISPR-Cas Systems in Bacteria and Archaea: Versatile Small RNAs for Adaptive Defense and Regulation", *Annu. Rev. Genet.* (2011) 45: pp. 273-297.
Bikard D. et al. "Programmable repression and activation of bacterial gene expression using an engineered CRISPR-Cas system" *Nucleic Acids Res* (2013) 41(15): pp. 7429-7437.
Bikard D., et al. "CRISPR interference can prevent natural transformation and virulence acquisition during in vivo bacterial infection", *Cell Host & Microbe* (2012), 10 pages.
Bikard D., et al. "Exploiting CRISPR-Cas nucleases to produce sequence-specific antimicrobial", *Nature Biotechnology* 2014, 6 pages.
Briner AE, Barrangou R. "*Lactobacillus buchneri* Genotyping on the Basis of Clustered Regularly Interspaced Short Palindromic Repeat (CRISPR) Locus Diversity", *Appl Environ Microbiol.* 80:994-1001, (2014).
Briner et al. "Guide RNA Functional Modules Direct Cas9 Activity and Orthogonality", *Molecular Cell.* (2014) 56(2): pp. 333-339.
Brouns SJJ, et al. "Small CRISPR RNAs guide antiviral defense in prokaryotes", *Science* (2008) 321:5891, pp. 960-964.
Carte et al. "The three major types of CRISPR-Cas systems function independently in CRISPR RNA biogenesis in *Streptococcus thermophilus*", *Molecular Microbiology*, 93(1), pp. 98-112 (2014).
Chylinski et al. "Classification and evolution of type II CRISPR-Cas Systems", *Nucleic Acids Research*, (2014) 15 pages.
Chylinski Krzysztof et al., "The tracrRNA and Cas9 families of type II CRISPR-Cas immunity systems", *RNA biology*, 10:5, 13 pages (2013).
Citorik R., et al. "Sequence-specific antimicrobials using efficiently delivered RNA-guided nucleases", *Nature Biotechnology* 2014, 7 pages.
Cong et al. "Multiplex Genome Engineering Using CRISPR/Cas Systems" *Science* (2013) vol. 339 (6121): pp. 819-823.
Darmon E, Leach DF "Bacterial Genome Instability", *Microbiol. Mol. Biol. Rev.* (2014) vol. 78, pp. 1-39.
Deltcheva, E. et al. "CRISPR RNA maturation by trans-encoded small RNA and host factor RNase III", *Nature*, vol. 471, (Mar. 2011) pp. 602-607.
Doench et al. "Rational design of highly active sgRNAs for CRISPR-Cas9-mediated gene inactivation", *Nature Biotechnology*, 32:12 (2014) 8 pages.
Dupuis MÈ et al., "CRISPR-Cas and restriction-modification systems are compatible and increase phaqe resistance", *Nat Commun.*, vol. 4, p. 2087 (2013).
Edgar R., et al. "The *Escherichia coli* CRISPR System Protects from Lysogenization, Lysogens, and Prophage Induction", *Journal of Bacteriology* (2010), vol. 192, No. 23, pp. 6292-6294.
Estvelt et al. "Orthogonal Cas9 proteins for RNA-guided gene regulation and editing", *Nature Methods*, 10:11 (2013) pp. 1116-1121.
Fonfara, I et al. "Phylogeny of Cas9 determines functional exchangeability of dual-RNA and Cas9 among orthologous type II CRISPR-Cas systems", *Nucleic Acids Res* (2013) 14 pages.

Fu et al. "Improving CRISPR-Cas nuclease specificity using truncated guide RNAs", *Nature Biotechnology*, 32:3 (2013) 9 pages.
Garneau JE, et al. "The CRISPR/Cas bacterial immune system cleaves bacteriophage and plasmid DNA" *Nature* (2010) 468(7320): pp. 67-71.
Gasiunas et al. "Cas9-crRNA ribonucleoprotein complex mediates specific DNA cleavage for adaptive immunity in bacteria", *Proc. Natl. Acad. Sci.* (2012), 109:E2579-E2586.
Gilbert et al. "Genome-Scale CRISPR-Mediated Control of Gene Repression and Activation", *Cell*, 159 (2014) pp. 647-661.
Gilbert, L. A. et al. "CRISPR-Mediated Modular RNA-Guided Regulation of Transcription in Eukaryotes", *Cell 154*, (2013) pp. 442-451.
Gomaa AA, et al. "Programmable Removal of Bacterial Strains by Use of Genome-Targeting CRISPR-Cas Systems", *mBio* (2014), 5(1):e00928-13.
Haurwitz et al. "Sequence- and Structure-Specific RNA Processing by a CRISPR Endonuclease", *Science* (2010) 329: pp. 1355-1358.
Horvath and Barrangou "CRISPR/Cas, the Immune System of Bacteria and Archaea", *Science* (2010) 327, pp. 167-170.
Horvath, P. et al. "Diversity, Activity, and Evolution of CRISPR Loci in *Streptococcus thermophilus*", *J Bacteriol.* 190 (2008) pp. 1401-1412.
Hsu et al. "DNA targeting specificity of RNA-guided Cas9 nucleases", *Nature Biotechnology*, 31:9 (2013) pp. 827-834.
Jiang, W. et al. "Dealing with the Evolutionary Downside of CRISPR Immunity: Bacteria and Beneficial Plasmids", *PLOS Genetics* (2013) vol. 9, issue 9, 13 pages.
Jiang, W. et al. "RNA-guided editing of bacterial genomes using CRISPR-Cas systems", *Nat. Biotechnol.* (2013) vol. 31, pp. 233-239.
Jinek et al. "A Programmable Dual-RNA-Guided DNA Endonuclease in Adaptive Bacterial Immunity", *Science* (2012) vol. 337, pp. 816-821.
Jinek, M. et al., "Structures of Cas9 endonucleases reveal RNA-mediated conformational activation", *Science* (2014) vol. 343, 6176, 28 pages.
Karvelis et al. "crRNA and tracrRNA guide Cas9-mediated DNA interference in *Streptococcus thermophilus*", *RNA Biol.* (2013) vol. 10: pp. 841-851.
Kobayashi K, et al. "Essential *Bacillus subtilis* genes", *Proc. Natl. Acad. Sci.* U.S.A. (2003) vol. 100, pp. 4678-4683.
Labrie SJ et al. "Bacteriophage resistance mechanisms" *Nat. Rev. Microbiol* (2010) vol. 8, pp. 317-327.
Luo, M. et al., "Repurposing endogenous type I CRISPR-Cas systems for programmable gene repression", *Nucleic Acid Research* (2014) 8 pages.
Magadan et al. "Cleavage of Phage DNA by the *Streptococcus thermophilus* CRISPR3-Cas System", *PLoS One* (2012) 7:040913. 8 pages.
Mahillon J. et al. "Insertion sequences", *Microbiol Mol Biol Rev* (1998) vol. 62(3): pp. 725-774.
Makarova and Koonin "Annotation and Classifi cation of CRISPR-Cas Systems", *Methods Mol Biol.* (2015), 1311: pp. 47-75.
Makarova et al. "An updated evolutionary classification of CRISPR-Cas systems", *Nat Rev Microbiol.* 13:722-736 (2015), 15 pages.
Makarova et al. "Unification of Cas protein families and a simple scenario for the origin and evolution of CRISPRCas systems", *Biol Direct.* (2011) vol. 6:38, 27 pages.
Makarova, K. S. et al. "Evolution and classification of the CRISPR-Cas systems", *Nat Rev Microbiol* (2011) vol. 9, pp. 467-477.
Marraffini and Sontheimer "CRISPR Interference Limits Horizontal Gene Transfer in Staphylococci by Targeting DNA", *Science* (2008) vol. 322: pp. 1843-1845.
Mojica, F. et al. "Short motif sequences determine the targets of the prokaryotic CRISPR defence system", *Microbiology* (2009) vol. 155, 8 pages.
Nishimasu, H., et al. "Crystal Structure of Cas9 in Complex with Guide RNA and Target DNA", *Cell* (2014) vol. 156, pp. 935-949.
Notification of International Preliminary Report on Patentability corresponding to International Application No. PCT/IB2015/052515; dated Oct. 12, 2016, 7 pages.

(56) References Cited

OTHER PUBLICATIONS

Notification and Transmittal of International Search Report and Written Opinion of the International Searching Authority for International Application No. PCT/IB2015/052515; dated Oct. 10, 2015; 12 pages.
Notification of Transmittal of the International Search Report and the Written Opinion of the International Searching Authority, or the Declaration, PCT/US2016/034812, dated Sep. 15, 2016, 9 pages.
Novagen "pCDF-1b Vector" Sep. 10, 2003, Retrieved from the Internet on Sep. 1, 2015, at http://www.helmholtz-muenchen.de/fieadmin/PEPF/pCDF_vectors/pCDF-1b_map.pdf, 2 pages.
Oh JH and van Pijkeren JP "CRISPR-Cas9-assisted recombineering in *Lactobacillus reuteri*", *Nucleic Acids Res* (2014) vol. 10.1093/nar/gku623.
Qi, L. S. et al. "Repurposing CRISPR as an RNA-Guided Platform for Sequence-Specific Control of Gene Expression", *Cell* 152, 1173-1183 (2013), 11 pages.
Sander JD, and Joung JK. "CRISPR-Cas systems for editing, regulating and targeting genomes", *Nat. Biotechnol.* (2014) vol. 32, pp. 347-355.
Sapranauskas et al. "The Streptococcus thermophilus CRISPR/Cas system provides immunity in *Escherichia coli*", *Nucleic Acid Res.* (2011) vol. 39: pp. 9275-9282.
Seed Kimberley D. et al., "A bacteriophage encodes its own CRISPR/Cas adaptive response to evade host innate immunity", *Nature*, 494:7438, pp. 489-491 (2013).
Selle K, Barrangou R. "Harnessing CRISPR-Cas systems for bacterial genome editing", *Cell Press: Trends Microbiol.* (2015) vol. 23(4): pp. 225-232.
Selle, K. et al. "CRISPR-based screening of genomic island excision events in bacteria", *Proc Natl Acad Sci USA*, (2015); 112(26): pp. 8076-8081.
Selle, K. et al., "CRISPR-Based Technologies and the Future of Food Science", *Journal of Food Science* (2015) vol. 80, 6 pages.
Semenova et al. "Interference by clustered regularly interspaced short palindromic repeat (CRISPR) RNA is governed by a seed sequence", *PNAS*, 108:25 (2011) 6 pages.
Sinkuna, T. et al. "In vitro reconstitution of Cascade-mediated CRISPR immunity in *Streptococcus thermophilus*", *The EMBO Journal* (2013) vol. 32, pp. 385-394.
Stern, A. et al., "Self-targeting by CRISPR: gene regulation or autoimmunity", *Cell Press: Trends in Genetics*, (2010) vol. 26, No. 8, 6 pages.
Sternberg et al. "DNA interrogation by the CRISPR RNA-guided endonuclease Cas9", *Nature*, vol. 507, (2014) 17 pages.
Terns and Terns "CRISPR-based adaptive immune systems", *Curr. Opin. Microbiol.* (2011) vol. 14: pp. 321-327.
Vercoe RB, et al. "Cytotoxic chromosomal targeting by CRISPR/Cas systems can reshape bacterial genomes and expel or remodel pathogenicity islands", *PLoS Genet* (2013) vol. 9(4):e1003454.
Westra et al. "The CRISPRs, They Are A-Changin': How Prokaryotes Generate Adaptive Immunity", *Annu. Rev. Genet.* (2012) vol. 46: pp. 311-339.

Wiedenheft et al. "RNA-guided complex from a bacterial immune system enhances target recognition through seed sequence interactions", *PNAS*, 108:36 (2011) 7 pages.
Written Opinion and International Search Report corresponding to International Application No. PCT/US2016/037493, dated Sep. 15, 2016, 8 pages.
Sashital et al. "Mechanism of foreign DNA selection in a bacterial adaptive immune system" Mol Cell., 46(5):6061-615 2012.
Third Party Observations corresponding to U.S. Appl. No. 15/735,028, dated Aug. 30, 2019 17 pages.
Beisel CL et al. A CRISPR design for next-generation antimicrobials. Genome Biology. 2014; 15: 516, 4 pages.
Citorik RJ et al. "Sequence-specific antimicrobials using efficiently delivered RNA-guiding nucleases Supplemental Material." Nature Biotechnology. Sep. 21, 2014; 32(11): 1141-1145. DOI:10.1038/nbt.3011, 14 pages.
Final Office Action, U.S. Appl. No. 15/133,656, dated Jul. 30, 2018, 8 pages.
Liu S et al. Complete genome sequence of *Lactobacillus buchneri* NRRL B-30929, a novel strain from a commercial ethanol plant. Journal of Bacteriology. Aug. 2011; 193(15): 4019-4020.
Liu S et al. NCBI (2011) CRISPR-associated protein, Csn1 family [*Lactobacillus buchneri*], pp. 1-3.
Ajdic et al. "hypothetical protein SMU_1405c [*Streptococcus mutans* UA159]", Proc. Natl. Acad. Sci. U.S.A. 99 (22), 14434-14439 (2002) URL: https://www.ncbi.nlm.nih.gov/protein/NP_721764.1/, retrieved Jul. 20, 2018.
Heinl, Stefan et al. "Insights into the completely annotated genome of Lactobacillus buchneri C0034, a strain isolated from stable grass silage", Journal of Biotechnology, 161:153-166 (2012).
International Search Report and Written Opinion for PCT/US2015/047136 dated Nov. 26, 2015, 10 pages.
Karvelis, Tautvydas et al., "crRNA and tracerRNK guide Cas9-mediated DNA interference in *Streptococcus thermophilus*," RNA Biology, 2013, vol. 10, Issue 5, pp. 841-851.
Karvelis, Tautvydas et al., "Programmable DNA cleavage in vitro by Cas9," Biochem. Soc. Trans. 2013, vol. 41, part 6, pp. 1401-1406.
Marcotte, H. et al. "Proteomes—Lactobacillus gasseri DSM 14869", NCBI Reference Sequence CP006803, (2013) URL: https://www.uniprot.org/proteomes/UP000217220, retrieved Jul. 20, 2018.
Ramakrishna Suresh et al. "Gene disruption by cell-penetrating peptide-mediated delivery of Cas9 protein and guide RNA", Genome Research, 24:1020-1027 (2014).
Cong et al. Supplementary Materials for "Multiplex Genome Engineering Using CRISPR/Cas Systems" Science (2013) vol. 339 (6121): pp. 819-823.
Lund, Paul E. "Pseudovirions as vehicles for the delivery of siRNA." Pharm Res. 27(3): 400-420 (2010).
Lowman, H B "Phage Display for Protein Binding." Encyclopedia of Biological Chemistry: Second Edition DO10.1016/B978-0-12-378630-2.00061-X (2013).

\* cited by examiner

METHODS AND COMPOSITIONS FOR DELIVERY OF CRISPR BASED ANTIMICROBIALS

STATEMENT REGARDING ELECTRONIC FILING OF A SEQUENCE LISTING

A Sequence Listing in ASCII text format, submitted under 37 C.F.R. § 1.821, entitled 5051-897_ST25.txt, 2805 bytes in size, generated on Aug. 14, 2020 and filed via EFS-Web, is provided in lieu of a paper copy. This Sequence Listing is hereby incorporated herein by reference into the specification for its disclosures.

STATEMENT OF PRIORITY

This application claims the benefit, under 35 U.S.C. § 119(e), of U.S. Provisional Application No. 62/275,421 filed on Jan. 6, 2016 and U.S. Provisional Application No. 62/271,114 filed on Dec. 22, 2015, the entire contents of which is incorporated by reference herein.

FIELD OF THE INVENTION

The invention relates to antibacterial compositions comprising bacteria modified to comprise phasmids engineered to deliver CRISPR RNAs and methods for their use.

BACKGROUND OF THE INVENTION

Antibiotic-resistance combined with the lack of alternative treatment strategies has become a worldwide threat. Despite decades of high-throughput screening approaches, in both industrial and academic settings, the results have been limited with no new antibiotics having been identified, and the number of synthetic derivatives that have been developed being relatively limited.

Increased understanding of the pathogenic nature of select microbes, combined with a key role for the gastrointestinal (GI) microbiota as a whole to maintain human health, has created a conundrum in health care. As of today, antibiotics are the primary line of treatment to eradicate bacterial pathogens. Yet, application of antibiotics results in major perturbations of the GI microbiota. These perturbations, especially in early life, have been correlated with long-lasting metabolic changes leading to obesity and allergic asthma (Oox et al. *Nature Reviews Endocrinology* 2014, 11, 182-190 DOI: 10.1038/nrendo.2014.210; Russell et al. *EMBO Rep* 2012, 13, 440-447), while antibiotic treatment in immune-compromised and elderly patients can result in antibiotic-associated diarrhea (Slimings et al. *J Antimicrob Chemother* 2014, 69, 881-891 DOI: 10.1093/jac/dkt477). In addition, historical over-use of antibiotics in both agriculture and health-care has led to the emergence of microbial antibiotic resistance, a major health threat in 21st century medicine (World Health Organization. *Antimicrobial resistance: global report on surveillance*; World Health Organization, 2014). Efforts to identify novel antimicrobials, in both industrial and academic settings, have been mostly futile. A major hurdle in the identification and development of novel antimicrobials is the requirement of the molecule to effectively penetrate the bacterial cell wall for subsequent activity (Lewis, K. *Nature Reviews Drug Discovery* 2013, 12, 371-387 DOI: 10.1038/nrd3975). Thus, there is an urgent need to develop novel antimicrobial therapeutics that can be delivered in-situ to modify the microbiota in a user-defined manner.

Accordingly, the present invention overcomes previous shortcomings in the art by providing compositions and methods of use that can alter the microbiome as well as circumvent commonly transmitted modes of drug resistance and treat bacterial infections.

SUMMARY OF THE INVENTION

In a first aspect, the invention provides a recombinant host bacterium comprising a recombinant phasmid, the recombinant phasmid comprising: (a) an origin of replication for a plasmid, (b) a genome from a bacteriophage of a target bacterium, wherein the bacteriophage genome does not include the bacteriophage replication and lysis modules, and (c) one or more CRISPR RNAs (crRNAs) comprising (i) a repeat sequence, having a 5' end and a 3' end, and (ii) a spacer-repeat sequence, having a 5' end and a 3' end, and the repeat sequence is linked at its 3' end to the 5' end of the spacer-repeat sequence, wherein the spacer is at least about 70% complementary to a nucleic acid of the target bacterium.

In a second aspect, a method of treating a bacterial infection in a subject in need thereof is provided, comprising administering to the subject a therapeutically effective amount of the host bacteria of the invention or a composition comprising the host bacterium of the invention.

In a third aspect, a method of killing of a target bacterial genus, species or strain present in or on a subject is provided, the method comprising administering to the subject a therapeutically effective amount of the host bacteria of the invention or a composition comprising the host bacterium of the invention, thereby killing the target bacterial genus, species or strain.

In a fourth aspect, a method of killing of a target bacterial genus, species or strain is provided, the method comprising contacting the target bacterial genus, species or strain with the host bacteria of the invention or a composition comprising the host bacterium of the invention thereby killing the target bacterial genus, species or strain.

In a fifth aspect, a method of altering the microbial (e.g., the bacterial population) population of a microbiome is provided, the method comprising introducing a host bacteria of the invention or a composition comprising the host bacterium of the invention into the microbiome, thereby altering the microbial composition of the microbiome.

Additional aspects of the invention provide kits comprising a host bacteria of the invention and/or a composition comprising the host bacterium of the invention.

These and other aspects of the invention are set forth in more detail in the description of the invention below.

BRIEF DESCRIPTION OF THE DRAWINGS

FIG. 2A provides an overview of a prototypical Type I CRISPR-Cas system. The universal cast and cast genes are shown in black. The Type I signature gene, cas3, is shown in dark grey, while the crRNA maturation nuclease cas6 is shown in light grey. Repeats are represented as black diamonds, and spacers as rectangles in various shades of grey located between the repeats. The leader sequence, which encodes transcription signals for the array is shown as a white rectangle. A typical Repeat-Spacer-Array (SEQ ID NOS:6-9) sub-section is shown on top. A prototypical Cascade complex is shown. In the transcription stage, the repeat-spacer array is transcribed as a full-length pre-crRNA, which is processed by cleavage into mature crRNAs, that contain a 5' handle followed by a full spacer and then a 3' handle containing a hairpin. The mature RNAs then form a ribonucleoprotein complex with Cascade to mediate interference by guiding endonucleases towards homologous nucleic acid sequences. Following R-loop formation, a double strand break is generated, and the Cas3 exonuclease then processes cleaved DNA in a 3' to 5' unidirectional manner. FIG. 2B shows an exemplary phasmid that supports replication in *E. coli*. DNA fragments of about 5 kb each are synthesized, corresponding to open reading frames (ORF) 1-21 of a phage, for example, CD38-2, as shown in FIG. 2B. These ORFs encode all the genes essential for the phage head morphogenesis, tail morphogenesis, and DNA packaging, and are sufficient to generate virions that can inject DNA into a target organism such as *C. difficile*. The synthetic CRISPR array (grey trapezoid) consists of a promoter, and a repeat-spacer-repeat sequence. In this example, the genome sequence of *C. difficile* 196 is used as a template for design, which is a rational approach as the CRISPR-Cas repeats and promoter sequences are highly conserved in *C. difficile* genomes. The spacer sequence corresponds to the toxin A (tcdA) that is conserved in hyper-virulent *C. difficile*. As shown, the CRISPR-cassette, the gene encoding alanine racemace (alr), and the lactococcal origin of replication (ORI) are fused to yield a single amplicon. Alanine racemase is an exemplary auxotrophic marker that can be used for selection for the phasmid in *L. lactis*Δalr.

DETAILED DESCRIPTION

Figure 1:
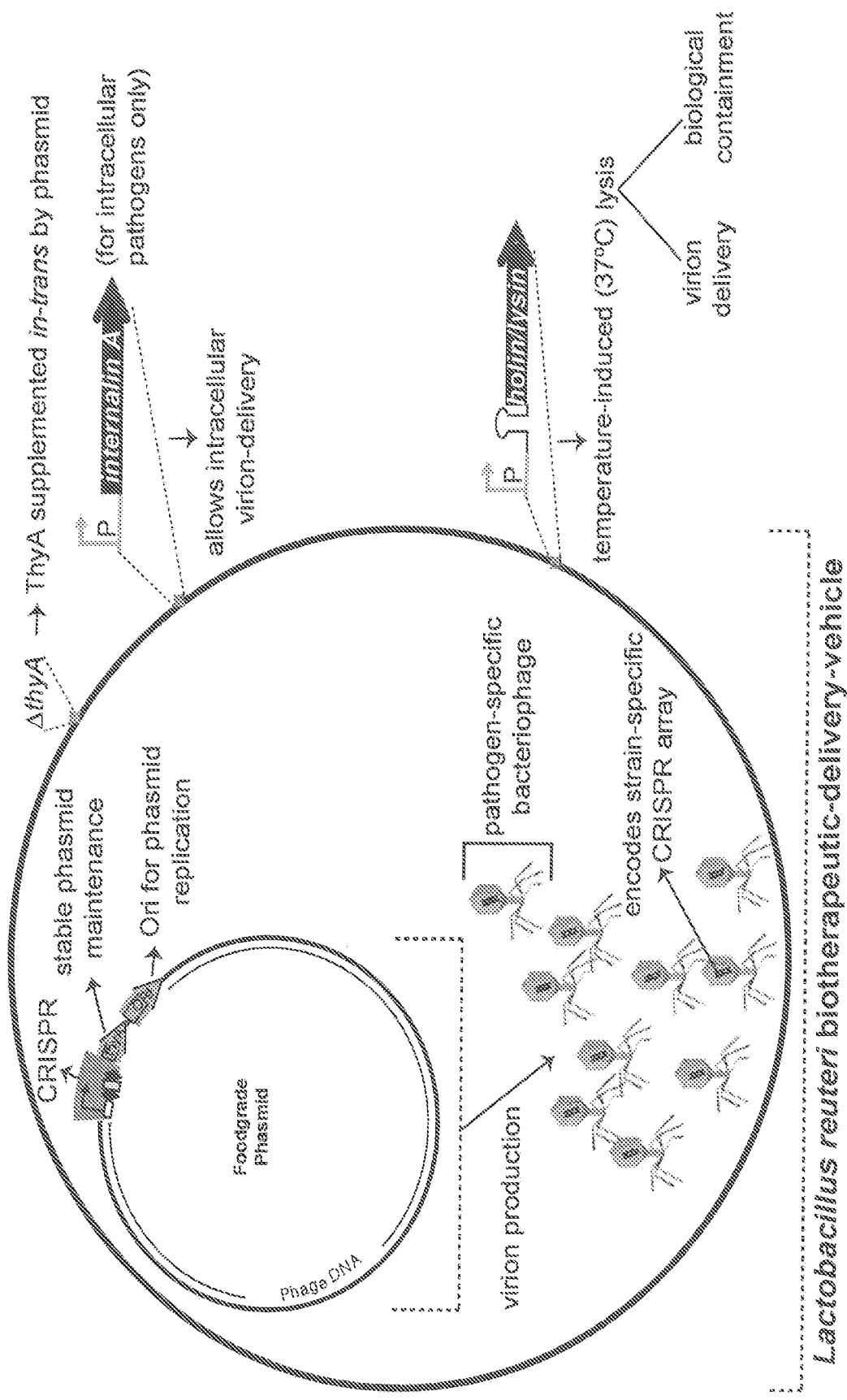
FIG. 1 shows an exemplary construct for a biotherapeutic delivery-vehicle comprising *Lactobacillus reuteri* as the host bacterium and including optional features such as an auxotrophic selection marker (e.g., thyA), internalin A (for use with intracellular target bacteria) and a construct for temperature induced lysis of the host bacterium and release of the bacteriophage particles in a regulated manner.

The present invention now will be described hereinafter with reference to the accompanying drawings and examples, in which embodiments of the invention are shown. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

As used in the description of the invention and the appended claims, the singular forms "a," "an" and "the" are intended to include the plural forms as well, unless the context clearly indicates otherwise. Also as used herein, "and/or" refers to and encompasses any and all possible combinations of one or more of the associated listed items, as well as the lack of combinations when interpreted in the alternative ("or").

The term "about," as used herein when referring to a measurable value such as a dosage or time period and the like refers to variations of ±20%, ±10%, ±5%, ±1%, ±0.5%, or even ±0.1% of the specified amount.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

As used herein, "chimeric" may refer to a nucleic acid molecule and/or a polypeptide in which at least two components are derived from different sources (e.g., different organisms, different coding regions). Also as used herein, chimeric refers to a construct comprising a polypeptide linked to a nucleic acid.

"Complement" as used herein can mean 100% complementarity with the comparator nucleotide sequence or it can mean less than 100% complementarity (e.g., about 80%, 81%, 82%, 83%, 84%, 85%, 86%, 87%, 88%, 89%, 90%, 91%, 92%, 93%, 94%, 95%, 96%, 97%, 98%, 99%, and the like, complementarity). Complement may also be used in terms of a "complement" to or "complementing" a mutation.

The terms "complementary" or "complementarity," as used herein, refer to the natural binding of polynucleotides under permissive salt and temperature conditions by base-pairing. For example, the sequence "5'-A-G-T-3" binds to the complementary sequence "5'-A-C-T-3'." Complementarity between two single-stranded molecules may be "partial," in which only some of the nucleotides bind, or it may be complete when total complementarity exists between the single stranded molecules. The degree of complementarity between nucleic acid strands has significant effects on the efficiency and strength of hybridization between nucleic acid strands.

"Cas9 nuclease" refers to a large group of endonucleases that catalyze the double stranded DNA cleavage in the CRISPR Cas system. These polypeptides are well known in the art and many of their structures (sequences) are characterized (See, e.g., WO2013/176772; WO/2013/188638). The domains for catalyzing the cleavage of the double stranded DNA are the RuvC domain and the HNH domain. The RuvC domain is responsible for nicking the (−) strand and the HNH domain is responsible for nicking the (+) strand (See, e.g., Gasiunas et al. *PNAS* 109(36):E2579-E2586 (Sep. 4, 2012)).

In some embodiments, the invention relies upon the presence of a native CRISPR-Cas system in the target bacterium to drive self-destruction directed by a synthetic crRNA. In other embodiments, the phasmid can be engineered to further comprise a heterologous CRISPR-Cas system (e.g., the polypeptides and polynucleotides of a CRISPR-Cas system) that can be used in the killing of the target bacterium.

Thus, in some embodiments, a phasmid can be engineered to comprise a heterologous nucleic acid encoding a Cas9 nuclease. In some embodiments, a Cas9 nuclease useful with this invention is any Cas9 nuclease that in combination with a crRNA of the phasmid and a tracr RNA (trans-encoded CRISPR RNA), or a synthetic single guide RNA (sgRNA) can drive the killing of the target bacterial cell. Thus, in some embodiments, a Cas9 nuclease useful with this invention can be a wild-type Cas9 nuclease. In other embodiments, a Cas9 nuclease useful with this invention can be a Cas9 nuclease that comprises one or more of the modifications as described herein, thereby resulting in a Cas9 nuclease having one or more modified activities relative to a wild-type Cas9 nuclease or a Cas9 nuclease not so modified.

In some embodiments, a Cas9 nuclease useful with the invention is a modified Cas9 nuclease that releases the cleaved target DNA (cleaved by the Cas9) more readily than a native Cas9 or a Cas9 that is not modified to more readily release cleaved target DNA as described herein. In some embodiments, a Cas9 nuclease modified to more readily release cleaved DNA, comprises a modified protospacer adjacent motif (PAM)-interacting domain (PIM). Modifications would reduce the affinity between Cas9 and the PAM without disrupting cleavage activity. The corresponding mutations to Cas9 can be identified by saturation mutagenesis of sites within the PIM implicated in binding the PAM as well as regions important for the folding and structural integrity of the PIM.

In some embodiments, a phasmid of the invention can be engineered to further comprises a Type I CRISPR-Cas system (e.g., Type I polypeptides, Type I Cascade polypeptides) in addition to a Type I crRNA.

As used herein, "Type I polypeptide" refers to any of a Cas3 polypeptide, Cas3' polypeptide, a Cas3" polypeptide, fusion variants thereof, and any one or more of the Type I Clustered Regularly Interspaced Short Palindromic Repeats (CRISPR)-associated complex for antiviral defense ("Cascade") polypeptides. Thus, the term "Type I polypeptide" refers to the polypeptides that make up a Type I-A CRISPR-Cas system, a Type I-B CRISPR-Cas system, a Type I-C CRISPR-Cas system, a Type I-D CRISPR-Cas system, a Type I-E CRISPR-Cas system, and/or a Type I-F CRISPR- Cas system. Each Type-I CRISPR-Cas system comprises at least one Cas3 polypeptide. Cas3 polypeptides generally comprise both a helicase domain and an HD domain. However, in some Type I CRISPR-Cas systems, the helicase and HD domain are found in separate polypeptides, Cas3' and Cas3". In particular, Cas3' encodes the helicase domain whereas Cas3" encodes the HD domain. Consequently, because both domains are required for Cas3 function, Type I subtypes either encode Cas3 (I-C, I-D, I-E, I-F) or Cas3' and Cas3" (I-A, I-B).

As used herein, "Type I Cascade polypeptides" refers to a complex of polypeptides involved in processing of pre-crRNAs and subsequent binding to the target DNA in type I CRISPR-Cas systems. These polypeptides include, but are not limited to, the Cascade polypeptides of Type I subtypes I-A, I-B, I-C, I-D, I-E and I-F. Non-limiting examples of Type I-A polypeptides include Cas7 (Csa2), Cas8a1 (Csx13), Cas8a2 (Csx9), Cas5, Csa5, Cas6a, Cas3' and/or a Cas3". Non-limiting examples of Type I-B polypeptides include Cas6b, Cas8b (Csh1), Cas7 (Csh2) and/or Cas5. Non-limiting examples of Type-IC polypeptides include Cas5d, Cas8c (Csd1), and/or Cas7 (Csd2). Non-limiting examples of Type-ID polypeptides include Cas10d (Csc3), Csc2, Csc1, and/or Cas6d. Non-limiting examples of Type I-E polypeptides include Cse1 (CasA), Cse2 (CasB), Cas7 (CasC), Cas5 (CasD) and/or Cas6e (CasE). Non-limiting examples of Type I-F polypeptides include Cys1, Cys2, Cas7 (Cys3) and/or Cas6f (Csy4).

In some embodiments, a phasmid of the invention further comprises a Type III CRISPR-Cas system in addition to a Type III crRNA. In some embodiments, a Type III CRISPR-Cas system can comprise a Cas6 polypeptide, a Csm complex (e.g., Type III-A Csm) and/or a Cmr complex (e.g., Type III-B Cmr). In some embodiments, a Csm complex may comprise Cas10 (or Csm1), Csm2, Csm3, Csm4, Csm5, and Csm6 polypeptides. In some embodiments, a Cmr complex may comprise Cmr1, Cas10 (or Csm2), Cmr3, Cmr4, Cmr5, and Cmr6 polypeptides.

In some embodiments, a phasmid of the invention further comprises a Type V CRISPR-Cas system, in addition to a Type V crRNA. Type V CRISPR-Cas systems can comprise a Cpf1 polypeptide and or a Cas1, Cas2 and/or Cas4 polypeptide. (Makarova et al. Nature Reviews Microbiology 13:722-736 (2015)).

A "fragment" or "portion" of a nucleotide sequence will be understood to mean a nucleotide sequence of reduced length relative (e.g., reduced by 1, 2, 3, 4, 5, 6, 7, 8, 9, 10, 11, 12, 13, 14, 15, 16, 17, 18, 19, 20 or more nucleotides) to a reference nucleic acid or nucleotide sequence and comprising, consisting essentially of and/or consisting of a nucleotide sequence of contiguous nucleotides identical or almost identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical) to the reference nucleic acid or nucleotide sequence. Such a nucleic acid fragment or portion according to the invention may be, where appropriate, included in a larger polynucleotide of which it is a constituent. In some embodiments, a fragment of a polynucleotide can be a functional fragment that encodes a polypeptide that retains its function (e.g., a fragment of a Cas9 polypeptide retains one or more of the activities of a native Cas9 nuclease including, but not limited to, HNH nuclease activity, RuvC nuclease activity, DNA, RNA and/or PAM recognition and binding activities). In representative embodiments, the invention may comprise a functional fragment of a Cas9 nuclease that is encoded by a fragment of a Cas9 polynucleotide. In further representative embodiments, the invention may comprise a functional fragment of a Cas3 nuclease that is encoded by a fragment of a Cas3 polynucleotide.

As used herein, the term "gene" refers to a nucleic acid molecule capable of being used to produce mRNA, tRNA, rRNA, miRNA, anti-microRNA, regulatory RNA, and the like. Genes may or may not be capable of being used to produce a functional protein or gene product. Genes can include both coding and non-coding regions (e.g., introns, regulatory elements, promoters, enhancers, termination sequences and/or 5' and 3' untranslated regions). A gene may be "isolated" by which is meant a nucleic acid that is substantially or essentially free from components normally found in association with the nucleic acid in its natural state. Such components include other cellular material, culture medium from recombinant production, and/or various chemicals used in chemically synthesizing the nucleic acid.

The term "genome" as used herein includes an organism's chromosomal/nuclear genome as well as any mitochondrial, and/or plasmid genome. In some embodiments, the genome of an organism may further comprise a phasmid and/or viral nucleic acid elements comprised in the organism.

A "hairpin sequence" as used herein, is a nucleotide sequence comprising hairpins (e.g., that forms one or more hairpin structures). A hairpin (e.g., stem-loop, fold-back) refers to a nucleic acid molecule having a secondary structure that includes a region of nucleotides that form a single strand that are further flanked on either side by a double stranded-region. Such structures are well known in the art. As known in the art, the double stranded region can comprise some mismatches in base pairing or can be perfectly complementary.

A "heterologous" or a "recombinant" nucleotide sequence is a nucleotide sequence not naturally associated with a host cell into which it is introduced, including non-naturally Different nucleic acids or proteins having homology are referred to herein as "homologues." The term homologue includes homologous sequences from the same and other species and orthologous sequences from the same and other species. "Homology" refers to the level of similarity between two or more nucleic acid and/or amino acid sequences in terms of percent of positional identity (i.e., sequence similarity or identity). Homology also refers to the concept of similar functional properties among different nucleic acids or proteins. Thus, the compositions and methods of the invention further comprise homologues to the nucleotide sequences and polypeptide sequences of this invention. "Orthologous," as used herein, refers to homologous nucleotide sequences and/or amino acid sequences in different species that arose from a common ancestral gene during speciation. A homologue of a nucleotide sequence or polypeptide of this invention has a substantial sequence identity (e.g., at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and/or 100%) to the nucleotide sequence or polypeptide of the invention. Thus, for example, a homologue of a repeat, a tracr sequence, a Cas9 polypeptide/polynucleotide, a Cas 3 polypeptide/polynucleotide, a Cmr polypeptide/polynucleotide, a Cascade polypeptide/polynucleotide and the like, can be about 70% homologous or more to any known repeat, tracr nucleic acid, Cas9 polypeptide/polynucleotide, Cas 3 polypeptide/polynucleotide, Cmr polypeptide/polynucleotide, or Cascade polypeptide/polynucleotide, respectively.

As used herein, hybridization, hybridize, hybridizing, and grammatical variations thereof, refer to the binding of two complementary nucleotide sequences or substantially complementary sequences in which some mismatched base pairs are present. The conditions for hybridization are well known in the art and vary based on the length of the nucleotide sequences and the degree of complementarity between the nucleotide sequences. In some embodiments, the conditions of hybridization can be high stringency, or they can be medium stringency or low stringency depending on the amount of complementarity and the length of the sequences to be hybridized. The conditions that constitute low, medium and high stringency for purposes of hybridization between nucleotide sequences are well known in the art (See, e.g., Gasiunas et al. (2012) *Proc. Natl. Acad. Sci.* 109:E2579-E2586; M. R. Green and J. Sambrook (2012) Molecular Cloning: A Laboratory Manual. 4th Ed., Cold Spring Harbor Laboratory Press, Cold Spring Harbor, N.Y.).

As used herein, the terms "increase," "increasing," "increased," "enhance," "enhanced," "enhancing," and "enhancement" (and grammatical variations thereof) describe an elevation of at least about 25%, 50%, 75%, 100%, 150%, 200%, 300%, 400%, 500% or more as compared to a control.

A "native" or "wild type" nucleic acid, nucleotide sequence, polypeptide or amino acid sequence refers to a naturally occurring or endogenous nucleic acid, nucleotide sequence, polypeptide or amino acid sequence. Thus, for example, a "wild type mRNA" is an mRNA that is naturally occurring in or endogenous to the organism. A "homologous" nucleic acid is a nucleotide sequence naturally associated with a host cell into which it is introduced. Thus, for example, as used herein, the term "an endogenous restriction enzyme" means a restriction enzyme that is naturally occurring in (native to) the production host bacterium.

Also as used herein, the terms "nucleic acid," "nucleic acid molecule," "nucleic acid construct," "nucleotide sequence" and "polynucleotide" refer to RNA or DNA that is linear or branched, single or double stranded, or a hybrid thereof. The term also encompasses RNA/DNA hybrids. When dsRNA is produced synthetically, less common bases, such as inosine, 5-methylcytosine, 6-methyladenine, hypoxanthine and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. The nucleic acid constructs of the present disclosure can be DNA or RNA, but are preferably DNA. Thus, although the nucleic acid constructs of this invention may be described and used in the form of DNA, depending on the intended use, they may also be described and used in the form of RNA.

A "synthetic" nucleic acid or polynucleotide, as used herein, refers to a nucleic acid or polynucleotide that is not found in nature but is constructed by the hand of man and as a consequence is not a product of nature.

As used herein, the term "polynucleotide" refers to a heteropolymer of nucleotides or the sequence of these nucleotides from the 5' to 3' end of a nucleic acid molecule and includes DNA or RNA molecules, including cDNA, a DNA fragment or portion, genomic DNA, synthetic (e.g., chemically synthesized) DNA, plasmid DNA, mRNA, and anti-sense RNA, any of which can be single stranded or double stranded. The terms "polynucleotide," "nucleotide sequence" "nucleic acid," "nucleic acid molecule," and "oligonucleotide" are also used interchangeably herein to refer to a heteropolymer of nucleotides. Except as otherwise indicated, nucleic acid molecules and/or polynucleotides provided herein are presented herein in the 5' to 3' direction, from left to right and are represented using the standard code for representing the nucleotide characters as set forth in the U.S. sequence rules, 37 CFR §§ 1.821-1.825 and the World Intellectual Property Organization (WIPO) Standard ST.25.

As used herein, the term "percent sequence identity" or "percent identity" refers to the percentage of identical nucleotides in a linear polynucleotide of a reference ("query") polynucleotide molecule (or its complementary strand) as compared to a test ("subject") polynucleotide molecule (or its complementary strand) when the two sequences are optimally aligned. In some embodiments, "percent identity" can refer to the percentage of identical amino acids in an amino acid sequence.

A "protospacer sequence" refers to the target double stranded DNA and specifically to the portion of the target DNA (e.g., or target region in the genome (e.g., the genome of the target bacterium)) that is fully or substantially complementary (and hybridizes) to a spacer sequence of a CRISPR RNA (crRNA). In the case of Type I and II CRISPR-Cas systems, the protospacer sequence is directly flanked by a PAM. In the case of Type III systems, the protospacer sequence is flanked by a sequence that shows limited complementarity to the 5' handle of the processed crRNA.

A "sub-optimal protospacer sequence" refers to a target DNA to which a spacer is designed, wherein the spacer comprises greater than 50% complementarity and less than 100% complementarity to the protospacer sequence. The reduced complementarity can come from, for example, truncating the spacer sequence at the 5' end by up to about 5 nucleotides, introducing up to 5 mismatches within the non-seed region, or introducing up to 3 mismatches within the seed region.

A "sub-optimal PAM sequence" refers to a PAM sequence that allows DNA cleavage but at a rate that is below an optimal PAM. For instance, the optimal PAM for the *Streptococcus pyogenes* Cas9 is NGG, whereas the sub-optimal PAM for this same Cas9 is NAG. Sub-optimal PAMs are commonly identified when applying high-throughput techniques for PAM elucidation. Recent studies have shown that various sub-optimal and non-canonical PAM sequences can be used, albeit with lower affinities and efficiencies.

As used herein, the terms "reduce," "reduced," "reducing," "reduction," "diminish," "suppress," and "decrease" (and grammatical variations thereof), describe, for example, a decrease of at least about 5%, 10%, 15%, 20%, 25%, 35%, 50%, 75%, 80%, 85%, 90%, 95%, 97%, 98%, 99%, or 100% as compared to a control. In particular embodiments, the reduction results in no or essentially no (i.e., an insignificant amount, e.g., less than about 10% or even less than about 5%) detectable activity or amount.

A "repeat sequence" as used herein, refers to, for example, any repeat sequence of a wild-type CRISPR locus (Type I, Type II, Type III or Type V) or a repeat sequence of a synthetic crRNA. A repeat sequence useful with this invention can be any known or later identified repeat sequence of a CRISPR locus (Type I, Type II, Type III or Type V) or it can be a synthetic repeat designed to function in a Type I, Type II, Type III or Type V CRISPR-Cas system. A repeat sequence may comprise a hairpin structure and/or a stem loop structure. Thus, in some embodiments, a repeat sequence can be identical to or substantially identical to a repeat sequence from a wild-type Type I, Type II, Type III or Type V CRISPR loci. A repeat sequence from a wild-type Type I, Type II, Type III or Type V CRISPR loci may be determined through established algorithms, such as using the CRISPRfinder offered through CRISPRdb (see, Grissa et al. *Nucleic Acids Res.* 35(Web Server issue):W52-7). In some embodiments, a repeat sequence or portion thereof is linked to the 5' end of a spacer sequence, thereby forming a repeat-spacer sequence. In other embodiments, a repeat sequence or portion thereof is linked to the 3' end of a spacer sequence, thereby forming a spacer-repeat sequence. In further embodiments, a repeat sequence or portion thereof is linked to the 5' end and to the 3' end of a spacer sequence, thereby forming a repeat-spacer-repeat sequence.

In some embodiments, a repeat sequence comprises, consists essentially of, or consists of at least one nucleotide (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or more nucleotides, or any range therein) depending on the CRISPR-Cas system (e.g., Type I, Type II, Type III, Type V), the particular repeat and whether the crRNA comprising the repeat is processed or unprocessed. In some embodiments, a repeat sequence comprises, consists essentially of, or consists of at least about one to about 40 nucleotides. In still other embodiments, a repeat sequence comprises, consists essentially of, or consists of at least about 8 nucleotides to about 40 nucleotides, or any range or value therein. In further embodiments, a repeat sequence can comprise, consist essentially of, or consist of about 10 nucleotides to about 40 nucleotides, about 15 nucleotides to about 40 nucleotides, about 20 nucleotides to about 40 nucleotides, about 25 nucleotides to about 40 nucleotides, about 1 to about 35 nucleotides, about 10 to about 35 nucleotides, about 15 to about 35 nucleotides, about 20 to about 35 nucleotides, about 25 to about 35 nucleotides, about 20 to about 30 nucleotides, and/or about 25 to about 30 nucleotides, or any range or value therein. In representative embodiments, a repeat sequence can comprise, consist essentially of, or consist of about 25 nucleotides to about 38 nucleotides, or any range or value therein. When more than one spacer sequence is present in a CRISPR array, each spacer nucleotide sequence is separated from another spacer by a repeat sequence. When more than one spacer is present in an array, each spacer may be complementary to a sequence (protospacer) in the genome of the same or a different target bacterium, thereby providing a single host bacterium delivery vehicle that can target one or more different bacterial genera, species or strains.

A "CRISPR RNA" or "crRNA" as used herein means a nucleic acid that comprises at least one spacer sequence and at least one repeat sequence, or a portion thereof, linked to the 5' end of the spacer sequence. The design of a crRNA of this invention will vary based on the CRISPR-Cas system in which the crRNA is to be used. The crRNAs of this invention are synthetic, made by man and not found in nature. In some embodiments, a crRNA may comprise, from 5' to 3', a repeat sequence (full length or portion thereof ("handle")), a spacer sequence, and a repeat sequence (full length or portion thereof). In some embodiments, a crRNA may comprise, from 5' to 3', a repeat sequence (full length or portion thereof ("handle")) and a spacer sequence. In some embodiments, a crRNA of this invention can further comprise a tracrRNA, thereby forming a single guide RNA (sgRNA) for a Type II CRISPR-Cas system.

In some embodiments, crRNA comprises at least one spacer sequence (having a 5' end and a 3' end) linked at its 3' end to the 5' end of at least one repeat sequence or a portion of the least one repeat sequence to form a "spacer-repeat sequence" having a 5' end and a 3' end In some embodiments, a crRNA may comprise a spacer-repeat sequence that comprises a further repeat sequence, or portion thereof, the further repeat sequence linked at its 3' end to the 5' end of a spacer-repeat sequence, thereby forming a "repeat-spacer-repeat sequence." In still further embodiments, a repeat-spacer-repeat sequence may be linked at the 3' end to at least one to up to about nine further spacer-repeat sequences (e.g., 1, 2, 3, 4, 5, 6, 7, 8, 9 additional consecutive spacer-repeat sequences). In such embodiments, each of the at least one up to nine additional consecutive spacer-repeat sequences, each having a 5' end and a 3' end, are linked at the 3' end to the 5' end of the next spacer-repeat sequence (e.g., a first spacer-repeat sequence linked at the 3' end to a second spacer-repeat sequence) and so on, to form, for example, a repeat-spacer-repeat-spacer-repeat with up to 10 spacer sequences alternating with up to 11 repeat sequences.

A crRNA of this invention can be "processed" or "unprocessed." An "unprocessed crRNA" may comprise at least one spacer linked at both the 5' end and at the 3' end to a full-length repeat sequence ("repeat-spacer-repeat" sequence). An unprocessed crRNA may comprise further spacer-repeat sequences linked to the 3' end of the repeat-spacer-repeat sequence (e.g., repeat-spacer-repeat-spacer-repeat-spacer-repeat-spacer-repeat and the like, up to about ten "spacer-repeat sequence" units). The design of a "processed crRNA may vary depending on whether the crRNA is intended for use with a Type I, Type II, Type III or a Type V CRISPR-Cas system. Thus, in some embodiments, a "processed crRNA" may comprise a spacer sequence linked at its 5' end to the 3' end of a portion of consecutive nucleotides of a repeat sequence (e.g., "a handle"). In some embodiments, a processed crRNA may further comprise a full length repeat sequence or a portion of consecutive nucleotides of a repeat sequence, the full length repeat sequence or portion of a repeat sequence being linked at its 5' end to the 3' end of the spacer sequence (see, e.g., R. Barrangou *Genome Biology* 16:247 (2015)).

A "spacer sequence" as used herein is a nucleotide sequence that is complementary to a target DNA in the genome of a target bacterium. In some embodiments, the target bacterium may be an animal bacterial pathogen, optionally a human bacterial pathogen. The spacer sequence can be fully complementary or substantially complementary (e.g., at least about 70% complementary (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to a target DNA in the genome of a target bacterium. Thus, in some embodiments, the spacer sequence can have one, two, three, four, or five mismatches as compared to the target DNA, which mismatches can be contiguous or non-contiguous. In some embodiments, the spacer sequence can have 70% identity to a target DNA. In other embodiments, the spacer nucleotide sequence can have 80% identity to a target DNA. In still other embodiments, the spacer nucleotide sequence can have 85%, 90%, 95%, 96%, 97%, 98%, 99% identity, and the like, to a target nucleotide sequence of a target gene. In representative embodiments, the spacer sequence has 100% complementarity to the target DNA. In some embodiments, the spacer sequence comprises a seed sequence that comprises about 9 nucleotides of the 5' portion of the spacer. In representative embodiments, the seed sequence has 100% complementarity to the target DNA. In particular embodiments, a spacer sequence has complete identity or substantial identity over a region of a target nucleotide sequence that is at least about 17 nucleotides to about 100 nucleotides in length or about 25 nucleotides to about 100 nucleotides in length.

Thus, in some embodiments, the 5' region of a spacer sequence can be identical to a target DNA while the 3' region of the spacer can be substantially identical to the target DNA and therefore the overall complementarity of the spacer sequence to the target DNA is less than 100%. Thus, for example, the first 7, 8, 9, 10, 11, 12, 13, 14, 15, 16, and the like, nucleotides in the 5' region of, for example, a 20 nucleotide spacer sequence (seed region) can be 100% complementary to the target DNA, while the remaining nucleotides in the 3' region of the spacer sequence are substantially complementary (e.g., at least about 70% complementary) to the target DNA. Thus, in some embodiments, the first 7 to 12 nucleotides, or the first 7 to 9 nucleotides, or the first 9 nucleotides of the 5' end of the spacer sequence can be 100% complementary to the target DNA, while the remaining nucleotides in the 3' region of the spacer sequence are substantially complementary (e.g., at least about 50% complementary (e.g., 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to the target DNA. In some embodiments, the 5' end of the spacer sequence can be 75%-99% complementary to the target DNA, while the remaining nucleotides in the 3' region of the spacer sequence can be at least about 50% to about 99% complementary to the target DNA. In other embodiments, the first 7 to 10 nucleotides in the 5' end of the spacer sequence can be 75%-99% complementary to the target DNA, while the remaining nucleotides in the 3' region of the spacer sequence are at least about 50% to about 99% complementary to the target DNA. In other embodiments, the first 7 to 10 nucleotides in the 5' end of the spacer sequence can be 100% complementary to the target DNA, while the remaining nucleotides in the 3' region of the spacer sequence are substantially complementary (e.g., at least about 70% complementary) to the target DNA.

In some embodiments, a spacer sequence of this invention can be about 17 nucleotides to about 100 nucleotides in length. In representative embodiments, a spacer nucleotide sequence of this invention can be about 17 nucleotides to about 100 nucleotides in length for a crRNA (e.g., for a crRNA intended for use in a Type II CRISPR-Cas system) (e.g., about 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 nucleotides, or any value or range therein) or about 25 nucleotides to about 100 nucleotides in length for a crRNA (e.g., for a crRNA intended for use in a Type I or a Type III CRISPR-Cas system) (e.g., about 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 nucleotides, or any value or range therein). In some particular embodiments, a spacer nucleotide sequence can be a length of about 17 to about 90 nucleotides, about 17 to about 80 nucleotides, about 17 to about 50 nucleotides, about 17 to about 40 nucleotides, about 17 to about 30 nucleotides, about 17 to about 25 nucleotides, about 17 to about 20 nucleotides, about 20 to about 50 nucleotides, about 20 to about 40 nucleotides, about 20 to about 30 nucleotides, about 20 to about 25 nucleotides, about 25 to about 90 nucleotides, about 25 to about 80 nucleotides, about 25 to about 50 nucleotides, about 25 to about 40 nucleotides, about 25 to about 35 nucleotides, about 25 to about 30 nucleotides, at least about 17 nucleotides, at least about 20 nucleotides, at least about 25 nucleotides, at least about 30 nucleotides, at least about 35 nucleotides, at least about 40 nucleotides, at least about 50 nucleotides, at least about 60 nucleotides, at least about 70 nucleotides, at least about 80 nucleotides, at least about 90 nucleotides, at least about 100 nucleotides in length, or more, and any value or range therein.

A "trans-activating CRISPR (tracr) nucleic acid" or "tracr nucleic acid" as used herein refers to any tracr RNA (or its encoding DNA). A tracr nucleic acid comprises from 5' to 3' a bulge, a nexus hairpin and terminal hairpins, and optionally, at the 5' end, an upper stem (See, Briner et al. (2014) *Molecular Cell.* 56(2):333-339). A tracr nucleic acid functions in hybridizing to the repeat portion of mature or immature crRNAs, recruits Cas9 protein to the target site, and may facilitate the catalytic activity of Cas9 by inducting structural rearrangement. Sequences for tracrRNAs are specific to the CRISPR-Cas Type II system and can be variable. When a phasmid is engineered to comprise a heterologous Type II CRISPR-Cas system in addition to a Type II crRNA, any tracr nucleic acid, known or later identified, can be used. In some embodiments, a tracr nucleic acid can be fused to a crRNA of the invention to form a single guide nucleic acid, and therefore, in some embodiments, an antimicrobial (chimeric construct) of the invention comprises a CPP linked to a crRNA and a tracr nucleic acid. In an exemplary embodiment, a Type II crRNA be fused to a trans-activating CRISPR (tracr) sequence to form a single guide RNA (sgRNA), the single guide RNA having a 3' end and 5' end and comprising: (A) a spacer sequence having a 5' end and a 3' end and a length of about 17-100 nucleotides, (B) a Type II repeat sequence having a 5' end and a 3' end, (C) a loop having a 5' end and a 3' end; and (D) a trans-activating CRISPR (tracr) sequence having a 5' end and a 3' end, wherein the spacer sequence is linked at the 3' end to the 5' end of the Type II repeat sequence, the 3' end of the Type II repeat sequence is linked to the 5' end of the loop, and the 3' end of the loop is linked to the 5' end of the tracr sequence. In some embodiments, the loop (e.g., linker) may comprise one to about 100 nucleotides (see, e.g., Briner et al. *Molecular Cell* 56: 1-7 (Oct. 23, 2014)).

As used herein "sequence identity" refers to the extent to which two optimally aligned polynucleotide or peptide sequences are invariant throughout a window of alignment of components, e.g., nucleotides or amino acids. "Identity" can be readily calculated by known methods including, but not limited to, those described in: Computational Molecular Biology (Lesk, A. M., ed.) Oxford University Press, New York (1988); *Biocomputing: Informatics and Genome Projects* (Smith, D. W., ed.) Academic Press, New York (1993); *Computer Analysis of Sequence Data*, Part I (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

As used herein, the phrase "substantially identical," or "substantial identity" in the context of two nucleic acid molecules, nucleotide sequences or protein sequences, refers to two or more sequences or subsequences that have at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and/or 100% nucleotide or amino acid residue identity, when compared and aligned for maximum correspondence, as measured using one of the following sequence comparison algorithms or by visual inspection. In particular embodiments, substantial identity can refer to two or more sequences or subsequences that have at least about 70%, at least about 75%, at least about 80%, at least about 85%, at least about 90%, at least about 95, 96, 96, 97, 98, or 99% identity.

For sequence comparison, typically one sequence acts as a reference sequence to which test sequences are compared. When using a sequence comparison algorithm, test and reference sequences are entered into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Package® (Accelrys Inc., San Diego, Calif.). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, Proc. Natl. Acad. Sci. USA 89: 10915 (1989)).

In addition to calculating percent sequence identity, the BLAST algorithm also performs a statistical analysis of the similarity between two sequences (see, e.g., Karlin & Altschul, Proc. Nat'l. Acad. Sci. USA 90: 5873-5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleotide sequence to the reference nucleotide sequence is less than about 0.1 to less than about 0.001. Thus, in some embodiments of the invention, the smallest sum probability in a comparison of the test nucleotide sequence to the reference nucleotide sequence is less than about 0.001.

As used herein, a "target DNA," "target nucleotide sequence," "target region," or a "target region in the genome" refers to a region of a target bacterium's genome that is fully complementary or substantially complementary (e.g., at least 70% complementary (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to a spacer sequence in a crRNA of this invention, optionally wherein the bacterium is an animal pathogen or a human pathogen. In some embodiments, a target region may be about 17 to about 100 consecutive nucleotides in length (e.g., about 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 nucleotides, or any value or range therein) or about 25 to about 100 consecutive nucleotides in length (e.g., about 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 nucleotides, or any value or range therein) which in Type I and Type II CRISPR-Cas systems is located immediately 3' or 5' to a PAM sequence, respectively, in the genome of the target bacterium.

A target nucleotide sequence or target DNA for use with a Type I and Type II CRISPR system is located adjacent to or flanked by a PAM (protospacer adjacent motif). While PAMs are often specific to the particular Type I or Type II CRISPR-Cas system, a PAM sequence can be determined by those skilled in the art through established experimental and computational approaches. Thus, for example, experimental approaches include targeting a sequence flanked by all possible nucleotides sequences and identifying sequence members that do not undergo targeting, such as through the transformation of target plasmid DNA (Esvelt et al. 2013. Nat. Methods 10:1116-1121; Jiang et al. 2013. Nat. Biotechnol. 31:233-239). In some aspects, a computational approach can include performing BLAST searches of natural spacers to identify the original target DNA sequences in bacteriophages or plasmids and aligning these sequences to determine conserved sequences adjacent to the target sequence (Briner and Barrangou. 2014. *Appl. Environ. Microbiol.* 80:994-1001; Mojica et al. 2009. *Microbiology* 155:733-740).

A "target bacterium" or "target bacterial cell" as used herein includes any genera, species or strain of bacteria for which eradication or reduction in numbers is desired. In some embodiments, the bacterium can be an animal pathogen. In some embodiments, the target bacterium comprises an endogenous Type I, Type II, Type III or Type V CRISPR-Cas system. A pathogenic bacterium is any bacterium that has a deleterious effect on the health of an animal. In some embodiments, a target bacterial cell useful with this invention does not express an endogenous CRISPR-Cas system but instead the recombinant phasmid comprised in the host bacterium of the invention is engineered to further comprise a heterologous CRISPR-Cas system to complement (work with) the crRNA of the engineered phasmid. The selection of the CRISPR-Cas system (e. g., Type I, Type II, Type III or Type V) is based on the crRNA comprised on the phasmid of the invention and to be used to target the killing of the target bacterium. Thus, if the crRNA is a Type I-E crRNA (e.g., comprises a Type I-E repeat) then the CRISPR-Cas system that is selected for introduction into the target bacterium or target archaeon is a Type I-E CRISPR-Cas system as well. The components of Type I, Type II, Type III and Type V CRIPSR systems are well known (Gomaa et al. *mBio* 5(1): e00928-13 (2014); Semenova et al. *Nucleic Acids Res.* 43(12):6049-61 (2015); Selle et al. *Proc Natl Acad Sci USA.;* 112(26):8076-81 (2015); Marraffini et al. *Science* 322 (5909): 1843-1845 (2008); and Hale et al. *Mol. Cell.* 54(3): 292-302 (2012)).

In some embodiments, a target bacterium can be any bacterium for which a bacteriophage sequence and a CRISPR-Cas system has been described. Exemplary target bacteria having at least one endogenous CRISPR-Cas system that may be useful with this invention include, but are not limited to, *Francisella tularensis, Novicida meningitidis, Pseudomonas aeruginosa, Salmonella enterica, Klebsiella pneumoniae, Staphylococcus aureus*, group B streptococci (e.g., *Streptococcus pyogenes, Streptococcus thermophilus, Streptococcus mutans, Streptococcus agalactiae, Streptococcus pneumoniae*), *Clostridium difficile, Escherichia coli, Enterococcus* spp. (e.g., *Enterococcus faecalis*), *Clostridium tetani, Helicobacter pylori, Fusobacterium nucleatum, Gardnerella vaginitis, Porphyromonas gingivalis, Aggregatibacter actinomycetemcomitans, Listeria monocytogenes, Staphylococcus aureus, Campylobacter jejuni, Vibrio vulnificus, Salmonella typhi, Clostridium botulinum, Mycobacterium tuberculosis, Mycobacterium leprae, Mycobacterium lepromatosis, Corynebacterium diptheriae, Klebsiella pneumoniae* or *Acinetobacter baumannii*.

Any polynucleotide of this invention (e.g., a heterologous polynucleotide encoding a Cas polypeptide (e.g., Cas9, Cas3, Cas7, etc.), a Cascade polypeptide, a Csm polypeptide and/or a Cmr polypeptide) can be codon optimized for expression in any species of interest. Codon optimization is well known in the art and involves modification of a nucleotide sequence for codon usage bias using species-specific codon usage tables. The codon usage tables are generated based on a sequence analysis of the most highly expressed genes for the species of interest. When the nucleotide sequences are to be expressed in the nucleus, the codon usage tables are generated based on a sequence analysis of highly expressed nuclear genes for the species of interest. The modifications of the nucleotide sequences are determined by comparing the species-specific codon usage table with the codons present in the native polynucleotide sequences. As is understood in the art, codon optimization of a nucleotide sequence results in a nucleotide sequence having less than 100% identity (e.g., 50%, 60%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and the like) to the native nucleotide sequence but which still encodes a polypeptide having the same function as that encoded by the original nucleotide sequence. Thus, in representative embodiments of the invention, a CRISPR-Cas polynucleotide can be codon optimized for expression in the particular target bacterial strain, species or genera.

In further embodiments of the invention, polynucleotides comprising tracr nucleic acids and/or crRNA and polynucleotides encoding a Cas polypeptides, Cascade polypeptides, Csm polypeptides, Cmr polypeptides, and the like, can be operatively associated with a variety of promoters, terminators and other regulatory elements for expression in the host bacterium. Thus, in representative embodiments, at least one promoter and/or terminator can be operably linked to a CRISPR polynucleotide. Any promoter useful with this invention can be used and includes, for example, promoters functional with the organism of interest including but not limited to constitutive, inducible, developmentally regulated, and the like, as described herein. A regulatory element as used herein can be endogenous or heterologous. In some embodiments, an endogenous regulatory element derived from the subject organism can be inserted into a genetic context in which it does not naturally occur (e.g., a different position in the genome than as found in nature), thereby producing a recombinant or non-native nucleic acid.

By "operably linked" or "operably associated" as used herein, it is meant that the indicated elements are functionally related to each other, and are also generally physically related. Thus, the term "operably linked" or "operably associated" as used herein, refers to nucleotide sequences on a single nucleic acid molecule that are functionally associated. Thus, a first nucleotide sequence that is operably linked to a second nucleotide sequence means a situation when the first nucleotide sequence is placed in a functional relationship with the second nucleotide sequence. For instance, a promoter is operably associated with a nucleotide sequence if the promoter effects the transcription or expression of the nucleotide sequence. Those skilled in the art will appreciate that the control sequences (e.g., promoter) need not be contiguous with the nucleotide sequence to which it is operably associated, as long as the control sequences function to direct the expression thereof. Thus, for example, intervening untranslated, yet transcribed, sequences can be present between a promoter and a nucleotide sequence, and the promoter can still be considered "operably linked" to the nucleotide sequence.

A "promoter" is a nucleotide sequence that controls or regulates the transcription of a nucleotide sequence (i.e., a coding sequence) that is operably associated with the promoter. The coding sequence may encode a polypeptide and/or a functional RNA. Typically, a "promoter" refers to a nucleotide sequence that contains a binding site for RNA polymerase and directs the initiation of transcription. In general, promoters are found 5', or upstream, relative to the start of the coding region of the corresponding coding sequence. The promoter region may comprise other elements that act as regulators of gene expression. These include, but are not limited to, a −35 element consensus sequence and a −10 consensus sequence (Simpson. 1979. *Proc. Natl. Acad. Sci. U.S.A.* 76:3233-3237).

Promoters can include, for example, constitutive, inducible, temporally regulated, developmentally regulated, and/or chemically regulated promoters for use in the preparation of recombinant nucleic acid constructs, polynucleotides, expression cassettes and vectors comprising the polynucleotides and recombinant nucleic acid constructs of the invention. These various types of promoters are known in the art.

Thus, in some embodiments, expression of a construct of the invention can be made constitutive, inducible, temporally regulated, developmentally regulated, and/or chemically regulated using the recombinant nucleic acid constructs of the invention operatively linked to the appropriate promoter functional in an organism of interest. In representative embodiments, repression can be made reversible using the recombinant nucleic acid constructs of the invention operatively linked to, for example, an inducible promoter functional in an organism of interest.

Promoters useful with this invention can include any promoter functional in bacteria. Exemplary promoters include useful with this invention include promoters functional in bacteria. A promoter useful with bacteria can include, but is not limited to, L-arabinose inducible (araBAD, $P_{BAD}$) promoter, any lac promoter, L-rhamnose inducible (rhaP$_{BAD}$) promoter, T7 RNA polymerase promoter, trc promoter, tac promoter, lambda phage promoter ($p_L$, $p_L$-9G-50), anhydrotetracycline-inducible (tetA) promoter, trp, lpp, phoA, recA, proU, cst-I, cadA, nar, lpp-lac, cspA, T7-lac operator, T3-lac operator, T4 gene 32, T5-lac operator, nprM-lac operator, Vhb, Protein A, corynebacterial-$E.$ $coli$ like promoters, thr, horn, diphtheria toxin promoter, sig A, sig B, nusG, SoxS, katb, α-amylase (Parry), Ptms, P43 (comprised of two overlapping RNA polymerase σ factor recognition sites, σA, σB) Ptms, P43, rplK-rplA, ferredoxin promoter, and/or xylose promoter. (See, K. Terpe $Appl.$ $Microbiol,$ $Biotechnol.$ 72:211-222 (2006); Hannig et al. Trends in Biotechnology 16:54-60 (1998); and Srivastava, $Protein$ $Expr$ $Purif$ 40:221-229 (2005)).

The choice of promoter will vary depending on the quantitative, temporal and spatial requirements for expression, and also depending on the host cell to be transformed. Promoters for many different organisms are well known in the art. Based on the extensive knowledge present in the art, the appropriate promoter can be selected for the particular host organism of interest. Thus, for example, much is known about promoters upstream of highly constitutively expressed genes in model organisms and such knowledge can be readily accessed and implemented in other systems as appropriate.

In some embodiments of the invention, inducible promoters can be used. Thus, for example, chemical-regulated promoters can be used to modulate the expression of a gene in an organism through the application of an exogenous chemical regulator. Regulation of the expression of nucleotide sequences of the invention via promoters that are chemically regulated enables the RNAs and/or the polypeptides of the invention to be synthesized only when, for example, an organism is treated with the inducing chemicals. Depending upon the objective, the promoter may be a chemical-inducible promoter, where application of a chemical induces gene expression, or a chemical-repressible promoter, where application of the chemical represses gene expression. In some aspects, a promoter can also include a light-inducible promoter, where application of specific wavelengths of light induce gene expression (Levskaya et al. 2005. $Nature$ 438:441-442).

"Introducing," "introduce," "introduced" (and grammatical variations thereof) in the context of a "microbiome" means placing the host bacterium in the same microbiome where at least one target bacterium is found such as in the gastrointestinal tract or digestive system (e.g., stomach, intestine, crop, proventiculus, rumen, reticulum, omasum, cecum), the skin, the urogenital tract (e.g., urethra, vagina, etc), the mouth, the respiratory tract, and/or the conjunctiva.

"Introducing," "introduce," "introduced" (and grammatical variations thereof) in the context of a polynucleotide of interest means presenting a polynucleotide of interest to a host organism or a cell of the organism (e.g., host cell such as a bacterial cell) in such a manner that the polynucleotide gains access to the interior of a cell and includes such terms as transformation," "transfection," and/or "transduction." Where more than one polynucleotide is to be introduced these polynucleotides can be assembled as part of a single polynucleotide or nucleic acid construct, or as separate polynucleotide or nucleic acid constructs, and can be located on the same or different expression constructs or transformation vectors. In some embodiments, introducing can include injection of phage DNA into a bacterial cell by a virion.

The terms "transformation," "transfection," and "transduction" as used herein refer to the introduction of a heterologous polynucleotide into a cell. Such introduction into a cell may be stable or transient. Thus, in some embodiments, a host cell or host organism is stably transformed with a nucleic acid molecule of the invention. In other embodiments, a host cell or host organism is transiently transformed with a recombinant nucleic acid molecule of the invention.

"Transient transformation" in the context of a polynucleotide means that a polynucleotide is introduced into the cell and does not integrate into the genome of the cell and cannot be maintained through antibiotic selection or addictive systems.

By "stably introducing" or "stably introduced" in the context of a polynucleotide introduced into a cell is intended that the introduced polynucleotide is stably incorporated into the genome of the cell, and thus the cell is stably transformed with the polynucleotide.

"Stable transformation" or "stably transformed" as used herein means that a nucleic acid molecule is introduced into a cell and integrates into the genome of the cell. As such, the integrated nucleic acid molecule is capable of being inherited by the progeny thereof, more particularly, by the progeny of multiple successive generations. "Genome" as used herein also includes the nuclear and the plasmid genome, and therefore includes integration of the nucleic acid construct into, for example, the plasmid genome. Stable transformation as used herein can also refer to a transgene that is maintained extrachromasomally, for example, as a minichromosome or a plasmid.

Transient transformation may be detected by, for example, an enzyme-linked immunosorbent assay (ELISA) or Western blot, which can detect the presence of a peptide or polypeptide encoded by one or more transgene introduced into an organism. Stable transformation of a cell can be detected by, for example, a Southern blot hybridization assay of genomic DNA of the cell with nucleic acid sequences which specifically hybridize with a nucleotide sequence of a transgene introduced into an organism (e.g., a bacterium). Stable transformation of a cell can be detected by, for example, a Northern blot hybridization assay of RNA of the cell with nucleic acid sequences which specifically hybridize with a nucleotide sequence of a transgene introduced into the cell. Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods Transformation can also be detected by direct sequencing and/or hybridization protocols well known in the art.

A polynucleotide of the invention can be introduced into a cell by any method known to those of skill in the art. Exemplary methods of transformation include transformation via electroporation of competent cells, passive uptake by competent cells, chemical transformation of competent cells, as well as any other electrical, chemical, physical (mechanical) and/or biological mechanism that results in the introduction of nucleic acid into a cell, including any combination thereof.

In some aspects, transformation of a cell may comprise nuclear transformation. In other aspects, transformation of a cell may comprise plasmid transformation and conjugation.

Procedures for transforming prokaryotic organisms are well known and routine in the art and are described throughout the literature (See, for example, Jiang et al. 2013. *Nat. Biotechnol.* 31:233-239; Ran et al. *Nature Protocols* 8:2281-2308 (2013))

"Effective amount" as used herein refers to an amount of a host bacterium and/or composition thereof that is sufficient to produce a desired effect, which can be a therapeutic and/or beneficial effect. The effective amount will vary with the age, general condition of the subject, the severity of the condition being treated, the particular agent administered, the duration of the treatment, the nature of any concurrent treatment, the pharmaceutically acceptable carrier used, and like factors within the knowledge and expertise of those skilled in the art. As appropriate, an "effective amount" in any individual case can be determined by one of skill in the art by reference to the pertinent texts and literature and/or by using routine experimentation. In some embodiments, an effective amount of a host bacterium and/or composition thereof may be about $10^5$ to about $10^{10}$ colony forming units (cfus). In some embodiments, an effective amount may be an amount that reduces the bacterial cell load by about 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100%, and any value or range therein.

A "therapeutically effective" amount as used herein is an amount that provides some improvement or benefit to the subject. Alternatively stated, a "therapeutically effective" amount is an amount that will provide some alleviation, mitigation, or decrease in at least one clinical symptom in the subject. Those skilled in the art will appreciate that the therapeutic effects need not be complete or curative, as long as some benefit is provided to the subject. In some embodiments, a therapeutically effective amount of a host bacterium of the invention or composition thereof may be about $10^5$ to about $10^{10}$ colony forming units (cfus) and any range or value therein. In some embodiments, a therapeutically effective amount results in the reduction of the bacterial population by about 1 to 5 log. In some embodiments, a therapeutically effective amount may be an amount that reduces the bacterial cell load by about 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100%, and any value or range therein.

By the terms "treat," "treating," or "treatment," it is intended that the severity of the subject's condition is reduced or at least partially improved or modified and that some alleviation, mitigation or decrease in at least one clinical symptom is achieved, and/or there is a delay in the progression of the disease or condition, and/or delay of the onset of a disease or illness. With respect to an infection, a disease or a condition, the term refers to, e.g., a decrease in the symptoms or other manifestations of the infection, disease or condition. In some embodiments, treatment provides a reduction in symptoms or other manifestations of the infection, disease or condition by at least about 5% to about 100%, e.g., about 5%, 10%, 15%, 20%, 25%, 30%, 35%, 40%, 45%, 50% or more.

Further, with respect to an infection, a disease or a condition, the terms "treat," "treating," or "treatment of" and the like refer to, e.g., elimination of or a decrease in the presence or amount of a microorganism (e.g., bacteria) in the subject. Thus, by treating the infection, disease, and/or condition in the subject, the infection, disease, and/or condition is ameliorated, alleviated, severity reduced, symptoms reduced and the like as compared to a similar subject not treated with the chimeric constructs of this invention, thereby treating the infection, disease and/or condition. In some embodiments, the treatment of an infection by a bacterium as described herein can be, for example, bactericidal and/or bacteriostatic. Thus, in some embodiments, the presence of a bacterium may be reduced by about 10% to about 100% (e.g., 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100%, or any value or range therein) upon contact with the chimeric construct of the invention of a composition thereof.

The term "bactericidal," refers to killing the microorganism and the term "bacteriostatic" "refers to inhibiting or retarding the growth of a bacterium, without killing the bacterium.

As used herein, the terms "eliminate," "eliminated," and/or "eliminating" refer to complete cessation of the specified activity.

As used herein, the terms "retarding the growth" or "retardation of growth" refers to reducing, delaying, inhibiting, and/or hindering the activity contributing to the growth and multiplication of a microorganism.

In some embodiments, a subject in need of treatment may be identified by, for example, well-established hallmarks of an infection, such as fever, puls, culture of organisms, and the like, or a subject may be treated prior to infection to prevent or reduce the likelihood of infection in the subject.

The terms "prevent," "preventing," and "prevention" (and grammatical variations thereof) refer to prevention and/or delay of the onset of an infection, disease, condition and/or a clinical symptom(s) in a subject and/or a reduction in the severity of the onset of the infection, disease, condition and/or clinical symptom(s) relative to what would occur in the absence of carrying out the methods of the invention prior to the onset of the disease, disorder and/or clinical symptom(s).

A "prevention effective" amount as used herein is an amount of a chimeric construct of the invention that is sufficient to reduce a bacterial load by at least about 10% to about 100%, and any range or value therein.

"Concurrently" means sufficiently close in time to produce a combined effect (that is, concurrently can be simultaneously, or it can be two or more events occurring within a short time period before or after each other). In some embodiments, the administration of two or more compounds "concurrently" means that the two compounds are administered closely enough in time that the presence of one alters the biological effects of the other. The two compounds can be administered in the same or different formulations or sequentially. Concurrent administration can be carried out by mixing the compounds prior to administration, or by administering the compounds in two different formulations, for example, at the same point in time but at different anatomic sites or using different routes of administration.

The present invention finds use in veterinary and medical applications as well as research applications. A "subject" of the invention includes any animal that has or is susceptible to an infection, disease or condition involving bacteria. Thus, such subject can be mammals, avians, reptiles, amphibians, insects or fish. Mammalian subjects include but are not limited to humans, non-human primates (e.g., gorilla, monkey, baboon, and chimpanzee, etc.), dogs, cats, goats, horses, pigs, cattle, sheep, and the like, and laboratory animals (e.g., rats, guinea pigs, mice, gerbils, hamsters, and the like). Avian subjects include but are not limited to chickens, ducks, turkeys, geese, quail, pheasants, and birds kept as pets (e.g., parakeets, parrots, macaws, cockatoos, canaries, and the like). Suitable subjects include both males and females and subjects of any age, including embryonic (e.g., in utero or in ovo), infant, juvenile, adolescent, adult and geriatric subjects. In some embodiments, a subject of this invention is a human.

A "subject in need" of the methods of the invention can be a subject known to have, suspected of having, or having an increased risk of developing an infection, disease, or condition, including secondary infections, caused by bacteria.

In some embodiments, the subject is one that has a bacterial infection, has had a bacterial infection, or is at risk for a bacterial infection. A subject at risk for a bacterial infection can be one that is, for example, in a hospital and is thereby exposed to infectious bacteria.

As a further aspect, the invention provides pharmaceutical compositions comprising the host bacterium of the invention and methods of administering the same to treat bacterial infections. In some embodiments, the composition may further comprise a pharmaceutically acceptable carrier.

By "pharmaceutically acceptable" it is meant a material that is not biologically or otherwise undesirable, i.e., the material can be administered to a subject without causing any undesirable biological effects such as toxicity.

The compositions of the invention can optionally comprise medicinal agents, pharmaceutical agents, carriers, adjuvants, dispersing agents, diluents, and the like. The compositions of the invention can be formulated for administration in a pharmaceutical carrier in accordance with known techniques. See, e.g., Remington, *The Science And Practice of Pharmacy* ($21^{th}$ Ed. 2005). In the manufacture of a pharmaceutical composition according to the invention, the host bacterium (delivery vehicle) may be admixed with, inter alia, an acceptable carrier. The carrier can be a solid (including a powder) or a liquid, or both, and is preferably formulated with the host bacteria as a unit-dose composition, for example, a tablet, which can contain from 0.01% or 0.5% to 95% or 99% by weight of the bacterial composition.

A further aspect of the invention is a method of treating subjects in vivo, comprising administering to a subject a pharmaceutical composition comprising the host bacteria of the invention in a pharmaceutically acceptable carrier, wherein the pharmaceutical composition is administered in a therapeutically effective amount. Administration of the host bacteria of the present invention to a human subject or an animal in need thereof can be by any means known in the art for administering such delivery vehicles as the host bacteria of this invention.

The recombinant host bacteria of the invention and compositions thereof can be manufactured in a form suitable for oral, rectal, topical, buccal (e.g., sub-lingual), vaginal, parenteral (e.g., subcutaneous, intramuscular including skeletal muscle, cardiac muscle, diaphragm muscle and smooth muscle, intradermal, intravenous, intraperitoneal), topical (i.e., both skin and mucosal surfaces, including airway surfaces), intranasal, transdermal, intraarticular, intrathecal, and inhalation administration, administration to the liver by intraportal delivery, as well as direct organ injection (e.g., into the liver, into the brain for delivery to the central nervous system, into the pancreas, or into a tumor or the tissue surrounding a tumor). In some embodiments, the host bacterial composition is delivered to the site of tissue infection, to a wound, to a burn, and the like. The most suitable route in any given case will depend on the nature and severity of the condition being treated.

For oral administration, the host bacteria of the invention can be administered in solid dosage forms, such as capsules, tablets, and powders, or in liquid dosage forms, such as elixirs, syrups, and suspensions. The host bacteria and/or compositions thereof can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that can be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Compositions suitable for buccal (sub-lingual) administration include lozenges comprising a flavored base, usually sucrose and acacia or tragacanth; and pastilles comprising an inert base such as gelatin and glycerin or sucrose and acacia.

Compositions suitable for rectal administration are preferably presented as unit dose suppositories. These can be prepared by admixing the host bacteria in one or more conventional solid carriers, for example, cocoa butter, and then shaping the resulting mixture.

Compositions suitable for topical application to the skin preferably take the form of an ointment, cream, lotion, paste, gel, spray, aerosol, or oil. Carriers which can be used include petroleum jelly, lanoline, polyethylene glycols, alcohols, transdermal enhancers, and combinations of two or more thereof.

Compositions suitable for transdermal administration can be presented as discrete patches adapted to remain in intimate contact with the epidermis of the recipient for a prolonged period of time. Compositions suitable for transdermal administration can also be delivered by iontophoresis (see, for example, Tyle, *Pharm. Res.* 3:318 (1986)) and typically take the form of an optionally buffered aqueous solution of the host bacterium.

The host bacteria can alternatively be formulated for nasal administration or otherwise administered to the lungs of a subject by any suitable means, e.g., administered by an aerosol suspension of respirable particles comprising the host bacteria of the invention, which the subject inhales. The respirable particles can be liquid or solid. The term "aerosol" includes any gas-borne suspended phase, which is capable of being inhaled into the bronchioles or nasal passages. Specifically, aerosol includes a gas-borne suspension of droplets, as can be produced in a metered dose inhaler or nebulizer, or in a mist sprayer. Aerosol also includes a dry powder composition suspended in air or other carrier gas, which can be delivered by insufflation from an inhaler device, for example. See Ganderton & Jones, *Drug Delivery to the Respiratory Tract*, Ellis Horwood (1987); Gonda (1990) *Critical Reviews in Therapeutic Drug Carrier Systems* 6:273-313; and Raeburn et al., *J. Pharmacol. Toxicol. Meth.* 27:143 (1992). Aerosols of liquid particles comprising the host bacteria of the invention can be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the host bacteria of the invention can likewise be produced with any solid particulate medicament aerosol generator, by techniques known in the pharmaceutical art.

Alternatively, one can administer the host bacteria in a local rather than systemic manner, for example, in a depot or sustained-release composition.

Further, the present invention provides liposomal formulations of the host bacteria disclosed herein. The technology for forming liposomal suspensions is well known in the art. When the host bacteria is in the form of an aqueous-soluble material, using conventional liposome technology, the same can be incorporated into lipid vesicles. In such an instance, the host bacteria can be substantially entrained within the hydrophilic center or core of the liposomes. The lipid layer employed can be of any conventional composition and can either contain cholesterol or can be cholesterol-free. Alternatively, employing conventional liposome formation technology, the host bacteria can be substantially entrained within the hydrophobic lipid bilayer which forms the structure of the liposome. In either instance, the liposomes which are produced can be reduced in size, as through the use of standard sonication and homogenization techniques. The liposomal compositions containing the host bacteria disclosed herein, can be lyophilized to produce a lyophilizate which can be reconstituted with a pharmaceutically acceptable carrier, such as water, to regenerate a liposomal suspension.

In addition, the host bacteria and compositions thereof can contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Other additives that are well known in the art include, e.g., detackifiers, anti-foaming agents, antioxidants (e.g., ascorbyl palmitate, butyl hydroxy anisole (BHA), butyl hydroxy toluene (BHT) and tocopherols, e.g., α-tocopherol (vitamin E)), preservatives, chelating agents (e.g., EDTA and/or EGTA), viscomodulators, tonicifiers (e.g., a sugar such as sucrose, lactose, and/or mannitol), flavorants, colorants, odorants, opacifiers, suspending agents, binders, fillers, plasticizers, lubricants, and mixtures thereof. The amounts of such additives can be readily determined by one skilled in the art, according to the particular properties desired.

The additive can also comprise a thickening agent. Suitable thickening agents can be those known and employed in the art, including, e.g., pharmaceutically acceptable polymeric materials and inorganic thickening agents. Exemplary thickening agents include polyacrylate and polyacrylate co-polymer resins, for example poly-acrylic acid and poly-acrylic acid/methacrylic acid resins; celluloses and cellulose derivatives including: alkyl celluloses, e.g., methyl-, ethyl- and propyl-celluloses; hydroxyalkyl-celluloses, e.g., hydroxypropyl-celluloses and hydroxypropylalkyl-celluloses such as hydroxypropyl-methyl-celluloses; acylated celluloses, e.g., cellulose-acetates, cellulose-acetatephthallates, cellulose-acetatesuccinates and hydroxypropylmethyl-cellulose phthallates; and salts thereof such as sodium-carboxymethyl-celluloses; polyvinylpyrrolidones, including for example poly-N-vinylpyrrolidones and vinylpyrrolidone co-polymers such as vinylpyrrolidone-vinylacetate co-polymers; polyvinyl resins, e.g., including polyvinylacetates and alcohols, as well as other polymeric materials including gum traganth, gum arabicum, alginates, e.g., alginic acid, and salts thereof, e.g., sodium alginates; and inorganic thickening agents such as atapulgite, bentonite and silicates including hydrophilic silicon dioxide products, e.g., alkylated (for example methylated) silica gels, in particular colloidal silicon dioxide products. Such thickening agents as described above can be included, e.g., to provide a sustained release effect. However, where oral administration is intended, the use of thickening agents as aforesaid will generally not be required and is generally less preferred. Use of thickening agents is, on the other hand, indicated, e.g., where topical application is foreseen.

In particular embodiments, the host bacteria may be administered to a subject in a therapeutically effective amount, as that term is defined above. The therapeutically effective dosage will vary somewhat from patient to patient, and will depend upon the condition of the patient and the route of delivery. In one embodiment, the host bacteria are administered at a dose of about $10^5$ to about $10^{10}$ colony forming units (cfu), e.g., about $10^5$, $5 \times 10^5$, $10^6$, $5 \times 10^6$, $10^7$, $5 \times 10^7$, $10^8$, $5 \times 10^8$, $10^9$, $5 \times 10^9$, $10^{10}$ cfu, and any range or value therein. The present invention encompasses every sub-range within the cited ranges and amounts.

There are no effective precision strategies to eradicate bacterial pathogens in Western medicine, though the therapeutic potential of bacteriophages has been appreciated since the 1930s (d'Herelle, F. *Bull N Y Acad Med* 1931, 7, 329-348). Now that antibiotic-resistance has become a major public health threat, investigations in bacteriophage therapy have revived, yet with limited success. Issues that have yet to be overcome include: 1) lack of homogeneity, partly due to the fragile nature of precursor phage particles (Abedon et al. *The bacteriophages.*, 2nd ed.; Calendar, R., Ed.; Oxford University Press, 2005; Powledge, T. M. *PLoS Biol* 2004, 2, e53 DOI: 10.1371/journal.pbio.0020053; 2) the susceptibility of many phages to low pH, which means that broad application of purified phage particles by oral administration will be unlikely to succeed (Chatain-Ly, M. H. *Frontiers in Microbiology* 2014, and 3) the inability of purified phage to target intracellular pathogens.

In the present invention, the inventors have developed new antimicrobial compositions (biotherapeutic delivery-vehicles) for alteration of an animal microbiome comprising a recombinant host bacterium comprising a recombinant phasmid, the recombinant phasmid comprising: (a) an origin of replication for a plasmid, (b) a genome from a bacteriophage of a target bacterium, wherein the bacteriophage genome comprised in the phasmid does not include the bacteriophage replication and lysis modules, and (c) at least one CRISPR RNA (crRNA) (e.g., 1, 2, 3, 4, 5, 6, 7, 8, 9, 10 or more crRNAs) comprising (i) a repeat sequence, having a 5' end and a 3' end, and (ii) a spacer-repeat sequence, having a 5' end and a 3' end, and the repeat sequence is linked at its 3' end to the 5' end of the spacer-repeat sequence, wherein the spacer is at least about 70% complementary to a nucleic acid of the target bacterium. In some embodiments, the spacer sequence comprises a seed sequence at the 5' end of the spacer (i.e., about 7-12 consecutive nucleotides or about 9 consecutive nucleotides at the 5' end of the spacer sequence), the seed sequence having 100% identity to the nucleic acid of the target bacterium. An exemplary biotherapeutic delivery-vehicle of the invention comprising *Lactobacillus reuteri* as the host bacterium is provided in FIG. 1.

The selectivity of the methods and compositions of the present invention is based on both the bacteriophage host-range and the CRISPR-array sequence. The selection of the target DNA of any given target bacterium can vary. Target DNA can be, for example, pathogen specific (toxins, adhesins) but can also be a target DNA that is less specific for a particular bacterial strain but which distinguishes between species, for example a 16S rRNA gene. Selection of sequences that are conserved within a target species but diverse in other species and genera can be desirable.

In some embodiments, the recombinant phasmid may comprise the phage genome modules (without the replication or lytic modules) in a single cluster. In some embodiments, a phasmid comprises in the following order a plasmid origin of replication, phage genome modules (absent the replication and lysis modules) and the CRISPR array (crRNA). In other embodiments, the crRNA of the phasmid can be located between phage genome modules. The phasmid is constructed so as to avoid interfering with native transcription patterns. In some embodiments, the phasmid can be about 10 kb to about 60 kb in size (e.g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 kb).

The genome of any bacteriophage that is known or later identified as infecting the target bacterium can be used with this invention. The phage genome modules that are incorporated into the phasmid include all genes necessary for phage head morphogenesis, tail morphogenesis and DNA packaging and do not include the replication modules or the lytic modules. Exemplary bacteriophage useful with this invention include but are not limited to CD196 for *C. difficile*, Funu1 for *F. nucleatum*, and/or KHP30 for *H. pylori*.

An origin of replication (ORI) useful with this invention can be any ORI that allows replication of the virions in the host bacterium, for example, phage P1, pAMß, pSH71, and/or mega-plasmid origins of replication.

In some embodiments the crRNA can be a Type I, Type II, Type III or Type V crRNA. In some embodiments, when the crRNA is a Type II crRNA the phasmid may further comprise a trans-activating CRISPR (tracr) sequence and a nucleic acid encoding a Cas9 polypeptide. In some embodiments, when the crRNA is a Type II crRNA the phasmid may further comprise a trans-activating CRISPR (tracr) sequence fused to the crRNA to form a single guide RNA (sgRNA) and a nucleic acid encoding a Cas9 polypeptide. In some embodiments, when the crRNA is a Type-I cRNA, the phasmid may further comprise a nucleic acid encoding a Type I CRISPR-Cas polypeptide and Type I Cascade polypeptides. In some embodiments, when the crRNA is a Type I crRNA, the crRNA can be a synthetic Type I processed guide RNA.

A spacer of a crRNA that is useful with this invention can be any sequence of consecutive nucleotides from the genome of a target bacterial strain, species or genus that is selective for that strain, species or genus. In some embodiments, a crRNA can comprise one or more spacer-repeat sequences (e.g., 1, 2, 3, 4, 5, 6, 7, 8, 9, 10 and the like).

In some embodiments, when the crRNA comprises two or more spacer-repeat sequences, the spacers of the two or more spacer-repeat sequences are each are separately at least 70% identical (e.g., about 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%) to the same or a different region of the genome of the same target bacterium or to a region of the genome of a different target bacterium.

In some embodiments, a host bacterium of the invention can be any nonpathogenic bacterium that can be engineered to comprise the recombinant phasmid of the invention and can survive in the same environment or microbiome in which the target bacterium is found (e.g., the gastrointestinal tract or digestive system (e.g., stomach, intestine, crop, proventiculus, rumen, reticulum, omasum, cecum), the skin, the urogenital tract (e.g., urethra, vagina, etc), the mouth, the respiratory tract, and/or the conjunctiva). In particular embodiments, the host bacterium can be a probiotic bacterium (a bacterium that when administered in adequate amounts, confer a health benefit on the host). In some embodiments, a host bacterium can be a lactic acid bacterium (e.g., *Lactobacillus* spp., *Lactococcus* spp., *Streptcoccus* spp.). In representative embodiments, a host bacterium can include but is not limited to *Lactococcus lactis*, *Streptococcus thermophilus*, *Lactococcus lactis*, *Lactobacillus reuteri*, *Lactobacillus acidophilus*, *Lactobacillus gasseri*, *Lactobacillus rhamnnosis*, *Lactobacillus johnsonii*, *Lactobacillus jensenii*, *Lactobacillus salivarius*, *Lactobacillus helveticus*, *Lactobacillus plantarum*, *Lactobacillus casei*, *Lactobacillus paracasei*, or *Lactobacillus pentosus*.

In some embodiments, a host bacterium can be engineered to lyse and release the phage particles comprising the crRNA in a controlled manner. Thus, in some embodiments, the host bacterium may comprise in its genome a heterologous nucleic acid operably linked to a promoter having a 5' end and a 3' end, the heterologous nucleic acid encoding a holin polypeptide and an endolysin polypeptide. In some embodiments, the lysis of the host bacterium is inducible by temperature or by the presence of an inducer molecule. Thus, in some embodiments, the host bacterial genome can comprise a nucleotide sequence located between the promoter and the heterologous nucleic acid that encodes a holin polypeptide and a endolysin polypeptide, the nucleotide sequence forming a secondary structure, for example, when the bacterium is grown below body temperature but not at temperatures at or above body temperature (i.e., the structure resolves at or above body temperature), wherein the secondary structure blocks transcription of the heterologous nucleic acid. In some embodiments, the secondary structure may be a hairpin loop. Alternatively, or in combination, a promoter that is inducible in the presence of particular compounds may be used to express the lysis construct (e.g., holing/endolsyin). Such compounds can include, but are not limited to, a bile acid. In some embodiments, a bacteriocin-based induction system may be used. In further embodiments two bacteria amy be used. For example, in one embodiment, the recombinant host bacteria of this invention that proliferates (e.g., in-vivo) may be one bacterium and bacteria producing an 'inducer' or, for example, lysin to induce lysis of the recombinant bacterium may be included as a second bacterium to release the engineered virions.

In some embodiments, the genome of the host bacterium may be modified, wherein the modification results in the host bacterium being auxotrophic for at least one compound required for its growth. Such a modification for auxotrophy in the host bacterium can be used in conjunction with a phasmid comprising a nucleic acid that when expressed complements the auxotrophy of the host bacterium, thereby providing phasmid stability in the host bacterium in the absence of antibiotic selection. Exemplary auxotrophic genes include alanine racemase (alr), and/or thymidine synthase (thyA).

In still further embodiments, the host bacterium can further comprise a nucleic acid encoding internalin. Such a modification may be used when the target bacterium is an intracellular bacterium.

In some embodiments, a target bacteria can include but is not limited to, *Clostridium difficile, Escherichia coli, Clostridium tetani, Helicobacter pylori, Fusobacterium nucleatum, Gardnerella vaginitis, Porphyromonas gingivalis, Aggregatibacter actinomycetemcomitans, Listeria monocytogenes, Staphylococcus aureus, Campylobacter jejuni, Vibrio vulnificus, Salmonella typhi, Clostridium botulinum, Mycobacterium tuberculosis, Mycobacterium leprae, Mycobacterium lepromatosis, Corynebacterium diptheriae, Klebsiella pneumoniae, Acinetobacter baumannii, Streptococcus mutans*, group B streptococci, including but not limited to, *Staphylococcus aureus, Streptococcus agalactiae, Streptococcus pneumonia, Enterococcus* spp. including, but not limited to, *Enterococcus faecalis*. In representative embodiments, the target bacterium can be *Clostridium difficile, Helicobacter pylori, Fusobacterium nucleatum*, or *Escherichia coli*.

In particular embodiments, the host bacterium can be *L. reuteri*, the bacteriophage strain can be CD196 and the target bacteria can be *C. difficile*. In further embodiments, the host bacterium can be *L. lactis*, the bacteriophage strain can be CD196 and the target bacteria can be *C. difficile*. In further embodiments, the host bacterium can be *L. reuteri*, the bacteriophage strain can be Funu1 and the target bacteria can be *F. nucleatum*. In additional embodiments, the host bacterium can be *L. reuteri*, the bacteriophage strain can be KHP30 and the target bacteria can be *H. pylori*.

In some embodiments, a composition is provided comprising a host bacterium of this invention, optionally wherein the composition further comprises a pharmaceutically acceptable carrier.

In some embodiment, a method of altering a the microbial composition of a microbiome is provided, the method comprising introducing a host bacteria of the invention or a composition comprising the host bacterium of the invention into the microbiome, thereby altering the microbial composition of the microbiome.

As used herein, "microbiome" refers to the population of microorganisms that are present in a particular environment, such as the gut or digestive system, the urogentical tract, the mouth and the like. A microbiome is a microbial population defined by the diversity as well as the relative amounts of bacteria that compose a particular microbiome. Thus, microbiomes can be altered by adding or removing certain genotypes, or by altering their relative quantitative ratios (see, e.g., Gomaa et al. *mBio* 5(1):e00928-13(January/February 2014) (doi:10.1128/mBio.00928-13)).

In some embodiments, a method of treating a bacterial infection in a subject in need thereof is provided, comprising administering to the subject a therapeutically effective amount of the host bacteria of the invention or a composition of the invention, thereby treating the bacterial infection.

In some embodiments, a method of killing of a target bacterial genus, species or strain present in or on a subject is provided, the method comprising administering to the subject a therapeutically effective amount of the host bacteria of the invention or a composition of the invention, thereby killing the target bacterial genus, strain or species present in or on the subject.

In some embodiments, a method of killing of a target bacterial genus, species or strain is provided, the method comprising contacting the host bacteria of the invention or a composition thereof, thereby killing the target bacterial genus, strain or species present in or on the subject.

In some embodiments, the bacteria targeted for killing or the bacteria that are causing the bacterial infection include but are not limited to, *Clostridium difficile, Escherichia coli, Clostridium tetani, Helicobacter pylori, Fusobacterium nucleatum, Gardnerella vaginitis, Porphyromonas gingivalis, Aggregatibacter actinomycetemcomitans, Listeria monocytogenes, Staphylococcus aureus, Campylobacter jejuni, Vibrio vulnificus, Salmonella typhi, Clostridium botulinum, Mycobacterium tuberculosis, Mycobacterium leprae, Mycobacterium lepromatosis, Corynebacterium diptheriae, Klebsiella pneumoniae, Acinetobacter baumannii, Streptococcus mutans*, group B streptococci, including but not limited to, *Staphylococcus aureus, Streptococcus agalactiae, Streptococcus pneumonia, Enterococcus* spp. including, but not limited to, *Enterococcus faecalis*. In representative embodiments, the bacterial infection is caused by *Clostridium difficile*.

In some embodiments, a method of reducing carcinogenesis of colorectal cancer in a subject in need thereof is provided, comprising administering to the subject a therapeutically effective amount of the host bacteria of the invention or a composition of the invention, thereby reducing carcinogenesis of colorectal cancer. In some embodiments, the method of carcinogenesis of colorectal cancer comprises administering host bacteria of the invention, wherein the target bacterium is *Fusobacterium nucleatum* (Fn). In some embodiments, carcinogenesis of colorectal cancer results in reduced inflammation and halting of tumor growth in addition to reducing the Fn bacterial load in the subject. In some embodiments, prophylactic eradication of Fn reduces carcinogenesis of colorectal cancer.

Additional aspects of the invention provide kits comprising one or more of the host bacteria of the invention and/or a composition comprising one or more host bacteria of the invention.

The invention will now be described with reference to the following examples. It should be appreciated that these examples are not intended to limit the scope of the claims to the invention, but are rather intended to be exemplary of certain embodiments. Any variations in the exemplified methods that occur to the skilled artisan are intended to fall within the scope of the invention.

EXAMPLES

Example 1

*Clostridium difficile* (CD) is the leading cause for nosocomial antibiotic-associated diarrhea. A major contributing factor to CD disease is antibiotics. Antibiotics cause a significant disruption of the patients' gastrointestinal microbiota that allows CD to quickly expand to consequently result in toxin-induced diarrhea, among other clinical manifestations (Britton and Young, 2014). In up to 30% of people previously treated for a CD infection, every future antibiotic treatment will trigger another episode of CD expansion, mostly instigated by hyper-virulent strains. The hyper-virulent phenotype (Merrigan et al., 2010), resistance to antibiotics commonly used in the clinic (He et al., 2013), and the realistic prospect that acquired antibiotic-resistance will go beyond the documented fluoroquinolone resistance (Baines et al., 2008; Freeman et al., 2010), collectively creates a perfect storm for a large epidemic. To date, the only successful remedy to recurrent CD infection is a fecal microbial transplant (FMT). Although FMT has success rates of about 90%, it has become evident in the last decade that the composition of the gut microbiota can be linked to a variety of diseases (Cho and Blaser, 2012), including obesity (Ley et al., 2005; Ridaura et al., 2013), and thus widespread FMT application should be cautioned. This is substantiated by a recent report that describes a case of a women who received a FMT, and rapidly gained 37 pounds and became obese (Alang and Kelly, 2015). Thus, subtle approaches to treat CD are much needed. The present invention is directed to a biotherapeutic platform to kill CD by hijacking the native adaptive immune system, CRISPR-Cas (Clustered, Regularly Interspaced Short Palindromic Repeats, and accompanying CRISPR-Associated sequences) (Horvath and Barrangou, 2010; Barrangou, 2013) of the target bacterial cell. In our invention, engineered virions, released by, for example, the host bacterium *Lactococcus lactis*, inject a CRISPR guide in CD cells to yield a transcript that together with CD native CRIPSR-Cas system causes self-destruction of the CD cells. This invention is expected to have a broad translational impact in the prevention and treatment of a wide-range of bacterial infections.

CRISPR-Cas systems and bacteriophages have been identified in many bacteria whose genomes have been sequenced, including many bacterial pathogens, all of which can be exploited to adapt our approach to prevent or treat many different bacterial infections. This approach should reduce the need for traditional antibiotics, thereby reducing the need for excessive application of antibiotics that has occurred in animal feed and in hospitals that combined with lack of alternative strategies, has resulted in bacterial antibiotic resistance and persistence (World Health Organization, 2014). Also, reducing or omitting antibiotic use should minimize the disruption of the microbiota, thereby preventing health problems associated with antibiotic use in early-life (Russell et al., 2012; Cox and Blaser, 2014).

Figure 2A:
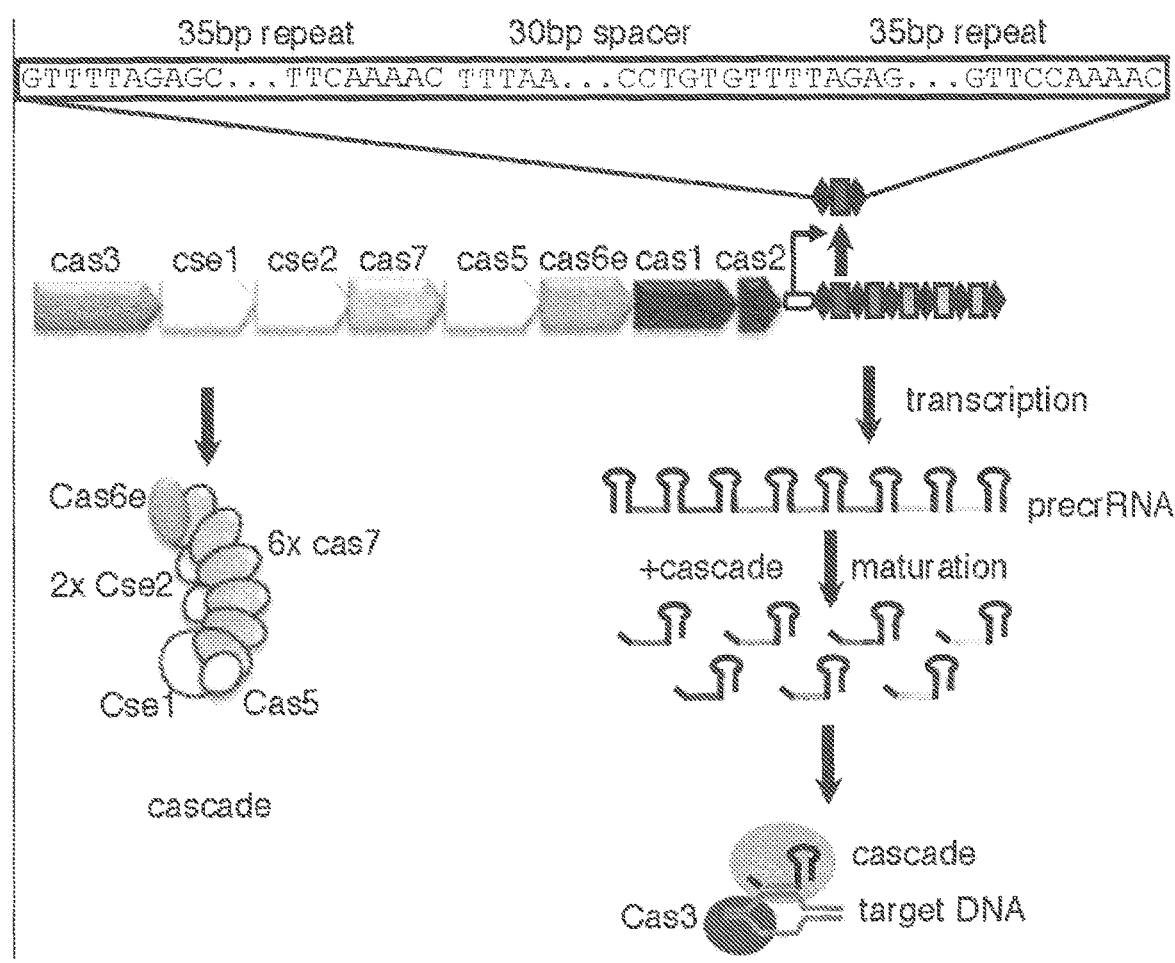
FIG. 2A-2B show a Type I CRISPR-Cas system mechanism of action and delivery of an engineered CRISPR array.

A. In-Vitro Assembly of a Phasmid that Replicates in *Lactococcus lactis*, and Produces Engineered Virions that Kill *Clostridium difficile* Upon Injection of a CRISPR-Array into the Bacterium Clustered regularly interspaced short palindromic repeats (CRISPR) and associated sequences (cas) constitute the adaptive immune system in bacteria and archaea (Barrangou et al. *Science* 2007, 315, 1709-1712), and are key in fending off viruses in bacteria and microbial communities (Tyson and Banfield, *Environ Microbiol* 2008, 10, 200-207). Generally, three distinct major types of CRISPR-Cas systems exist, namely Types I, II and III (Makarova et al. *Nat Rev Microbiol* 2011, 9, 467-477). FIG. 2A provides a detailed overview of Type I CRISPR-Cas system, which is conserved in hyper-virulent *Clostridium difficile* strains, and is exploited in the present invention directed to self-destruction of this pathogen. Although much of the interest in CRISPR-Cas systems has focused on their genome editing potential (Jiang et al. *Nat Biotech* 2013, 31, 233-239; Mali et al. *Nat Meth* 2013, 10, 957-963; Oh and van Pijkeren, *Nucleic Acids Research* 2014, 42, e131-e131), CRISPR-Cas is also a powerful tool to remove cells from a mixed community (Gomaa et al. *mBio* 2014, 5, e00928-13 DOI: 10.1128/mBio.00928-13.). However, the major bottleneck is the limitation to efficiently introduce the CRISPR-Cas in the target cell. One application has recently been published describing bacteriophages that deliver CRISPR-Cas to the target bacteria yielding strain-specific killing of *Staphylococcus* (Bikard et al. *Nat Biotech* 2014, 32, 1146-1150). However, the application of helper phage to package the DNA is problematic as only a portion (2.9%) of phages in the total phage population was reported to have packaged the phagemid encoding CRISPR-Cas, further reducing homogeneity when produced in batch. The present approach capitalizes on the fusion of a replicating plasmid and phage DNA (=phasmid) that produces functional virions (Nicoletti et al. *Mol Gen Genet* 1983, 189, 343-347; Piekarowicz et al. *J. Virol.* 2014, 88, 1002-1010)

Ligation-cycle reaction (LCR) can be used to generate a food-grade phasmid that replicates in *L. lactis*, which includes DNA encoding a crRNA guide that will direct the endogenous Type-I-B CRISPR-Cas system cascade machinery towards the chromosome of *C. difficile*.

Amplification and synthesis of phasmid components. Template DNA and amplification of the various components of the phasmid are obtained as follows. The genome sequence of phage CD38-2 has been determined (Sekulovic et al., 2011), and this phage infects a variety of strains with the hyper-virulent 027 ribotype, including *C. difficile* CD196 (Sekulovic et al., 2014). ORFs 1-21 of CD38-2, the CRISPR-cassette targeting the toxin A gene of clinical isolates of *C. difficile* 196 and the lactococcal origin of replication (ORI)(van Kranenburg and de Vos, 1998) are synthesized (GeneArt® Strings™, Life Technologies), and the auxotrophic marker alanine racemase (alr), including promoter, is amplified from *L. lactis* MG1363. The pSMART® BAC vector system is obtained from Lucigen.

In-vitro assembly of the phasmid using *E. coli* as a cloning host. Although purified plasmids and conventional ligations can be transformed effortlessly in *L. lactis*, *E. coli* has been used in this example for transforming assemblies obtained by ligation cycle reaction (LCR) due to the superior transformation efficiency of *E. coli*, which is 1,000-10,000-fold higher when using ultra-competent cells. Therefore, in this example, *E. coli* is used as the intermediate cloning host, followed by electroporation of purified phasmid in *L. lactis*. All the different components are assembled in the pSMART® BAC vector system to allow replication in *E. coli*. We have previously shown that LCR can be used to generate plasmids of 30 kb with the pSMART® BAC vector system. Once assembly is accomplished, the full size phasmid is isolated using the QIAfilter Plasmid kit (Qiagen), which supports purification of plasmids up to about 50 kb.

Figure 2B:
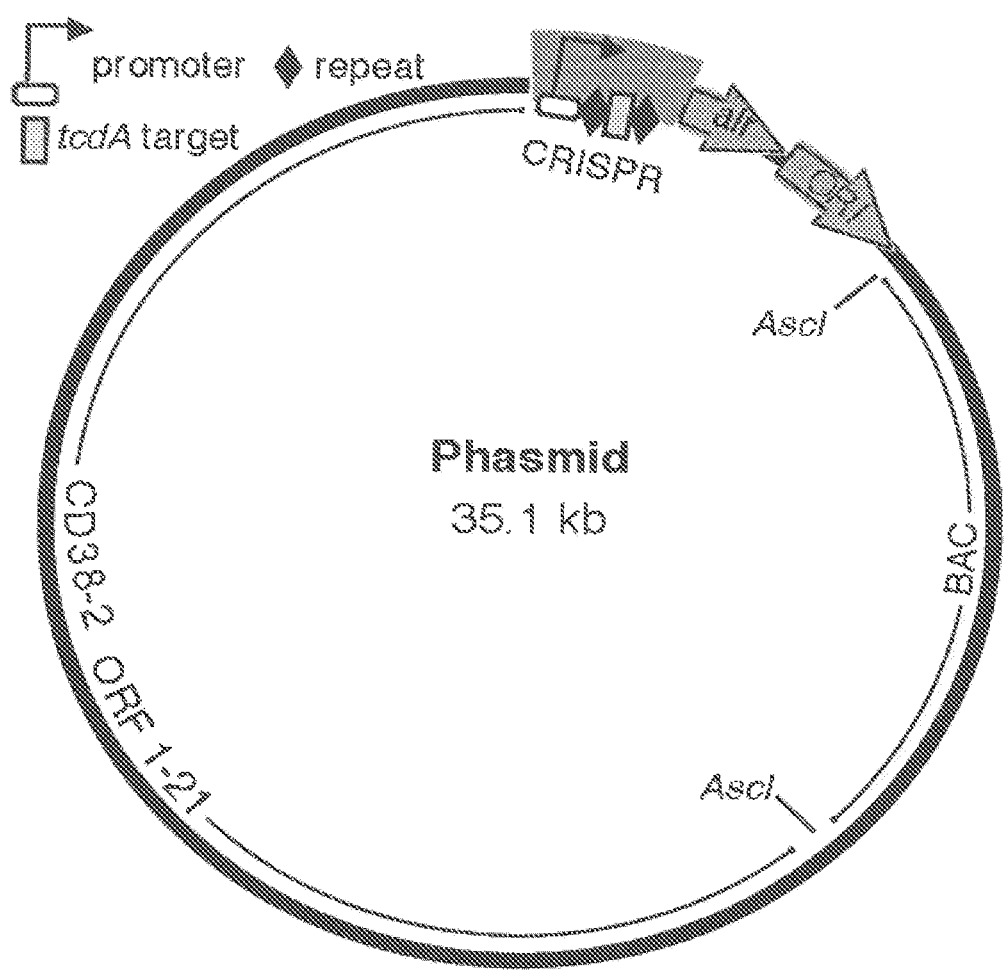

FIG. 2A-2B show a Type I CRISPR-Cas system mechanism of action and delivery of an engineered CRISPR array. FIG. 2A provides an overview of a prototypical Type I CRISPR-Cas system. FIG. 2B shows an exemplary phasmid that supports replication in *E. coli*. DNA fragments, each about 5 kb in size are synthesized, corresponding to open reading frames (ORF) 1-21 of a phage, for example, CD38-2, as shown in FIG. 2B. These ORFs encode all of the genes essential for the phage head morphogenesis, tail morphogenesis, and DNA packaging, and are sufficient to generate virions that can inject DNA into a target organism such as *C. difficile*. The synthetic CRISPR array (grey trapezoid) consists of a promoter and a repeat-spacer-repeat sequence. In this example, the genome sequence of *C. difficile* 196 is used as a template for design, which is a rational approach as the CRISPR-Cas repeats and promoter sequences are highly conserved in *C. difficile* genomes. The spacer sequence corresponds to the toxin A (tcdA) that is conserved in hyper-virulent *C. difficile*. As shown, the CRISPR-cassette, the gene encoding alanine racemace (alr), and the lactococcal origin of replication (ORI) are fused to yield a single amplicon. Alanine racemase is an exemplary auxotrophic marker that can be used for selection for the phasmid in *L. lactis*Δalr. Notably, the ORI has been previously characterized and supports replication of about a 40 kb plasmid in *L. lactis* MG1363 (van Kranenburg et al. *Journal of Bacteriology* 1998, 180, 5285-5290). The bacterial strains described in this proposal are direct derivatives of *L. lactis* MG1363, and thus this ORI will be functional to support replication of our phasmid. Two PCR amplicons are generated corresponding to the pSMART® BAC vector. The flanks of the pSMART BAC vector will have a AscI restriction recognition site included, which will allow removal of the pSMART backbone. The different fragments are subjected to a LCR reaction, as previously described (de Kok et al. *ACS Synth. Biol.* 2014, 3, 97-106), followed by electroporation in ultracompetent BAC-Optimized Replicator™ v2.0 Electrocompetent Cells (Lucigen). A control phasmid is constructed that does not contain a CRISPR-sequence targeting *C. difficile*. Integrity of constructs are verified by PCR and Sanger sequencing analysis.

Establishing the phasmid in *L. lactis*Δalr. For replication in *L. lactis*Δalr the backbone of pSMART BAC becomes obsolete, and therefore this backbone is removed. AscI restriction digest, followed by self-ligation (FIG. 2B) yields a 27.6 kb phasmid (phasmid_tcdA and phasmid_ctrl) that can replicate in *L. lactis*. The phasmid does not contain an antibiotic marker but instead the alr gene, encoding the enzyme alanine racemace, which will ensure stable replication in *L. lactis*Δalr. The enzyme alanine racemase is responsible for the interconversion of L-alanine (L-Ala) and D-alanine (D-Ala), the latter a key component in the peptidoglycan backbone of *L. lactis* cells. Using this mechanism, the recombinant *L. lactis* becomes completely dependent on exogenously added D-Ala when the alr gene is deleted, which can be exploited as a stringent selection maker in lactic acid bacteria, including *L. lactis* (Bron et al., 2002). Other such nucleic acids that confer auxotrophy when modified (to reduce or eliminate their expression) are well known in the art and may be used interchangeably.

By a conventional double-crossover method, as previously has been described for a variety of lactic acid bacteria (Law et al., 1995; van Pijkeren et al., 2006), the alr gene is deleted yielding *L. lactis*Δalr, and this derivative serves as a host for our phasmid constructs. Electrocompetent cells of *L. lactis*Δalr are prepared, and purified phasmid DNA is electroporated. Cells are plated on regular GM17-agar plates, and colonies that are obtained after electroporation are expected to contain phasmid_tcdA or phasmid_ctrl as it provides the alanine racemace enzyme in-trans allowing the *L. lactis*Δalr cells to grow in the absence of exogenously added D-Ala. Colonies are screened by PCR analysis to confirm the presence of each phasmid.

Testing the supernatant of *L. lactis*Δalr harboring phasmid_tcdA for killing activity of *C. difficile* 196. Autolysis, mediated by the protein AcmA, is a well-documented phenomenon in *L. lactis*, and is characterized by a reduction of the optical density (up to 60%) of a culture that has reached late stationary growth phase (Buist et al., 1997). Therefore, it is expected that virions produced from the phasmid will be released in the supernatant of stationary phase cells. This approach is a preferred over mechanical cell disruption or enzymatic treatment, both of which can damage the virions.

The culture supernatant of stationary phase *L. lactis*Δalr cells harboring phasmid_tcdA is collected and used to show that the produced virions are functional in their ability to kill *C. difficile* by injecting the CRISPR-tcdA. As a control, supernatant of *L. lactis*Δalr harboring phasmid_ctrl is also harvested. Bacteria are cultured in the presence of MOPS buffer to maintain a stable pH of about 7, and supernatant is filtered by filter sterilization (0.45 µm). Lactococcal growth medium (GM17) is filter-sterilized for use as another negative control.

*C. difficile* 196 is cultured anaerobically in a glove box chamber (Coy Laboratories) to mid-logarithmic phase, and diluted to $10^4$ cells/ml in pre-reduced Brain Heart Infusion (BHI) broth. Cells are supplemented with 1% (v/v) of filter-sterilized: GM17 medium, supernatant derived from *L. lactis*Δalr+phasmid_tcdA or supernatant derived from *L. lactis*Δalr+phasmid_ctrl. Every 15 minutes *C. difficile* cells are collected followed by viable plate count to assess cell killing. A minimum of three biological replicates are collected and samples are analyzed by a paired t-test.

In some instances, lysates can be concentrated to provide more virions than may be present in a natural lysate. As controls, concentrated lysates of the strain harboring phamsid_ctrl, and TP901-1 can be included. The latter will be tested in its lytic host *L. lactis* 3107 (Stockdale et al., 2013).

Panel a shows in-vitro assembly of nine amplicons corresponding to the *L. lactis* bacteriophage sequence TP901-1 (amplicon 1-7) and the vector backbone pSMART BAC (Lucigen; amplicon 8-9) by ligation cycle reaction (LCR). Panel b confirms assembly by PCR analysis of a representative correctly assembled clone. Oligonucleotide pairs (ab, cd, of etcetera) are indicated on top of the gel. Each primer was located on the proximal end of each adjacent fragment, as indicated in Panel a, to confirm assembly.

Figure 3:
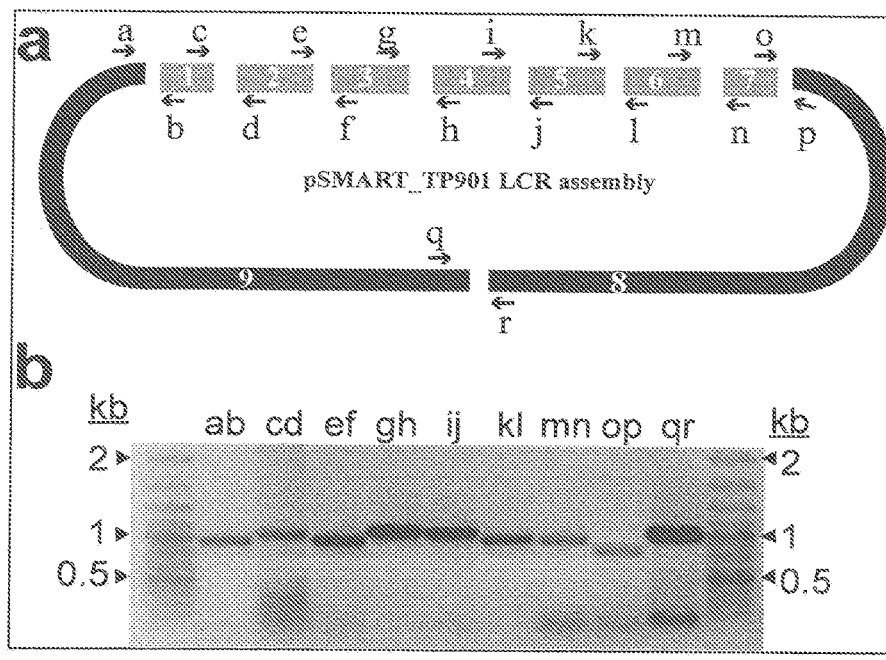
FIG. 3 shows an exemplary in-vitro assembly of 30 kb phasmid by ligation cycle reaction. Panel a shows in-vitro assembly of nine amplicons corresponding to the *L. lactis* bacteriophage sequence TP901-1 (amplicon 1-7) and the vector backbone pSMART BAC (Lucigen; amplicon 8-9) by ligation cycle reaction (LCR). Panel b confirms assembly by PCR analysis of a representative correctly assembled clone. Oligonucleotide pairs (ab, cd, of etcetera) are indicated on top of the gel. Each primer was located on the proximal end of each adjacent fragment, as indicated in Panel a, to confirm assembly.

Phasmid assembly. In-vitro assembly of an exemplary 30 kb phasmid is shown in FIG. 3. Here, nine amplicons corresponding to the *L. lactis* bacteriophage sequence TP901-1 (Stockdale et al., 2013) (amplicon 1-7) and the vector backbone pSMART BAC (Lucigen; amplicon 8-9) by ligation cycle reaction (LCR, (de Kok et al., 2014)) (Panel a). The bacteriophage amplicons were 1.7 kb (fragment 1), 4 kb (fragments 2-6) and 1.1 kb (fragment 7) totaling 22.9 kb. Two 3.8 kb amplicons were generated corresponding to the pSMART BAC vector (fragments 8-9). LCR was performed as described (de Kok et al., 2014) with the only modification that 50 cycles were performed. Although only 4% of our LCR mixture was electroporated in sub-optimal electrocompetent *E. coli* cells ($10^8$ cfu/µg pKan plasmid), we confirmed by PCR correct assembly of 60% of the colonies tested. Confirmation of assembly by PCR analysis of a representative correctly assembled clone is shown in Panel b. All amplicons were shown to have the expected size, which was between 788 bp (oligo pair 'op') and 1067 bp (oligo 'gh'). The water controls were all negative and the positive controls using TP901-1 DNA (cd, ef, gh, ij, kl, mn), pSMART BAC DNA (qr) all yielded amplicons of the same size, while no amplicon was generated with 'ab' and 'op'.

Figure 4:
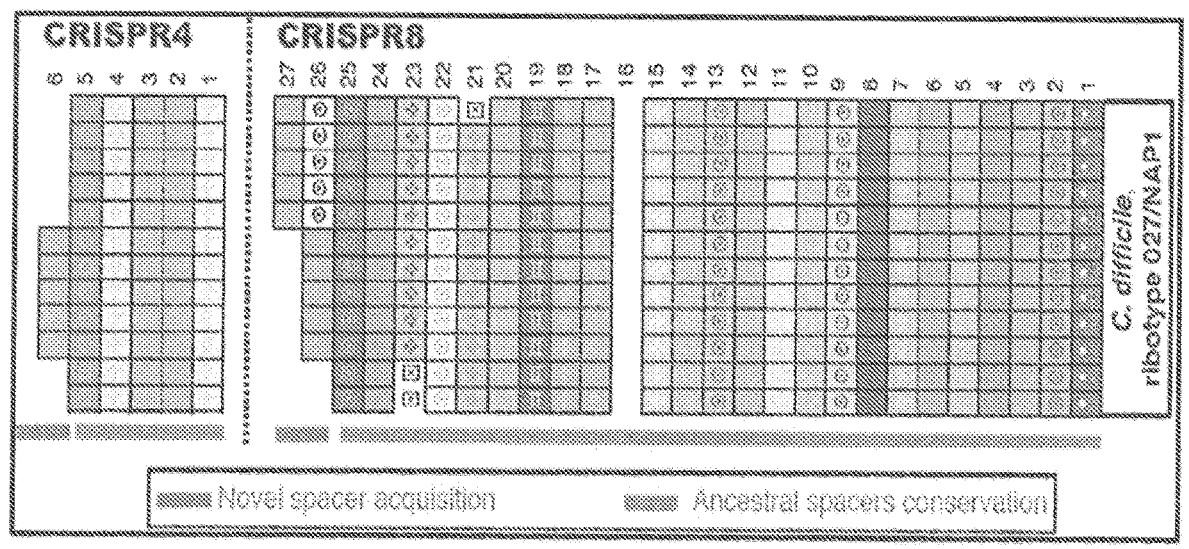
FIG. 4 provides a visualization of the Type I-B CRISPR spacer content for 12 *Clostridium difficile* ribotype 027 isolates. Each line represents the CRISPR content from one strain. Only spacers are represented, all conserved repeats were removed. Each square represents a CRISPR spacer, and unique color combinations represent unique spacer sequences. Deletions/missing spacers are represented as crossed squares. Spacers are numbered in order of predicted acquisition in the locus. Conserved ancestral spacers are highlighted with a blue line below this section of the array, and variable and recently acquired spacers are highlighted with a red line below this portion of the locus.

Activity of CRISPR-Cas Type-I-B system in hyper-virulent *Clostridium difficile*. Bioinformatics analyses indicate that the CRISPR-Cas Type-I-B system is widespread, conserved, and active in hyper-virulent *Clostridium difficile* (FIG. 4), thus supporting our approach to exploit the native Cascade (CRISPR associated complex for antiviral defense) machinery for specific sequence targeting of the host *C. difficile* chromosome. FIG. 4 shows two distinct CRISPR arrays present at two distinct loci on the chromosome are represented, namely CRISPR4 and CRISPR8. Given the variety of spacers found in the different hyper-virulent *C. difficile* strains, including strain *C. difficile* 196 (ribotype 027/NAP1), thus shows that the CRISPR-Cas Type-I-B system is active.

B. Biotherapeutic Efficacy.

Lactic acid bacteria, including *Lactococcus lactis*, have been part of the human diet for thousands of years given their role in the fermentation of dairy products. The long history of human consumption of *L. lactis*, its inability to colonize humans (Vesa et al., 2000), as well as proven clinical safety (Villatoro-Hernandez et al., 2011) yields no doubt that this lactic acid bacterium is an ideal host to deliver therapeutics safely in-situ. Although lactic acid bacteria are generally not genetically accessible, a variety of genetic tools are available to engineer *L. lactis*. Aside from earlier established tools to integrate genes in the chromosome (Law et al., 1995; Solem et al., 2008), we have developed several tools for use in lactic acid bacteria (van Pijkeren and Britton, 2012; Oh and van Pijkeren, 2014), including single-stranded DNA recombineering (SSDR), which is highly efficient in *L. lactis* (van Pijkeren et al., 2012). SSDR provides the opportunity to use oligonucleotides to make subtle base changes, insert multiple bases, or to make deletions up to 500 bp in a high-throughput manner without the need for antibiotic selection.

Increased bile resistance of *L. lactis* is believed to increase its survival during gastrointestinal transit (Watson et al., 2008), while programmed expression of a bacteriophage holin may yield slow lysis of *L. lactis* (de Ruyter et al., 1997). Delivery of CRISPR arrays carrying multiple self targeting spacers in *C. difficile* may further increase the killing efficacy of *C. difficile* as it is documented that multiple CRISPR spacers reduce the number of 'escapers' (Barrangou et al., 2007; Barrangou, 2013; Levin et al., 2013). A lactic acid bacterium with increased bioactivity during gastrointestinal transit that will increase the number of cells subjected to programmed lysis when the cells encounter 37° C. will be engineered, thereby increasing the efficacy of virion release in-vivo and increasing the therapeutic load in-situ. This will be tested by inserting the *Listeria monocytogenes* bilE gene in the *L. lactis* chromosome, while programmed lysis will be achieved by cloning a *Lactococcus* bacteriophage holin gene, the expression of which is temperature controlled. In addition, a phasmid will be constructed that contains multiple CRISPR cassettes.

Temperature-dependent lysis. *L. lactis* strain is engineered that starts releasing the virions once the animals ingest the bacterium but not when cultured in-vitro. Since the optimum growth temperature for *L. lactis* is 30° C., a system was engineered that activates *L. lactis* cell lysis once the bacteria encounter body temperature (37° C.). This is accomplished using an RNA thermosensor present in *Listeria monocytogenes* that plays a key role in temperature dependent activation of a master regulator in virulence, PrfA (Johansson et al., 2002). Downstream of the prfA promoter is an untranslated mRNA (UTR) region. At 30° C. no PrfA is produced: the prfA-UTR is predicted to mask the ribosomal binding site, thus blocking translation, while at 37° C. the structure of UTR allows prfA to be highly expressed. Placing the prfA-UTR upstream of a gene that induces cell lysis will ensure that virions are being released in-situ once the cells are ingested, and not during in-vitro experiments or batch culturing. This may be an advantageous characteristic for industrial production and sustained homogeneity.

A variety of options for inducing cell lysis in *L. lactis* exist but for use in the gastrointestinal tract, lysis should occur slowly to ensure that virions are being released during gastrointestinal transit, and not suddenly when the cells encounter 37° C. Therefore, the bacteriophage TP901-1 holin protein (Labrie et al., 2004; Stockdale et al., 2013), which is referred herein as LytH will be used. Bacteriophage holins and lysins induce lysis of a bacterium during the lytic cycle of the bacteriophage. LytH is a small protein that makes lesions in the bacterial membrane resulting in membrane collapse, after which the lysin protein can degrade the peptidoglycan to yield full cell lysis. It has been shown that expression of only LytH yields slow lysis in *L. lactis* (de Ruyter et al., 1997). Thus, the combination of prfA-UTR fused to lytH should yield slow cell lysis when the cells encounter 37° C., and thus slow release of virions during gastrointestinal transit. After synthesis of the promoter-lytH DNA, the cassette is inserted in the host bacterial chromosome in an identical manner as described above, yielding strain *L. lactis*::lytH.

To experimentally validate the dynamics of cell lysis at 37° C. in-vitro, strains *L. lactis* wild-type and *L. lactis*::lytH are cultured at 30° C. to different growth phases (early-mid-late logarithmic phase, and early stationary phase). Subsequently, half of each culture is transferred to 37° C. (t=0). Subsequent samples are taken every 30 minutes for 8 hours to measure growth rate, cell viability, and to collect the supernatant to assess cell lysis. A well-established assay is used to determine the level of the intracellular peptidase X-prolyl dipeptidyl aminopeptidase (PepX) in the culture supernatant, which is a measure for cell lysis (Buist et al., 1997; Steen et al., 2005). A supernatant of cells (same growth stage, same volume) is included that has been completely disrupted by bead-beating and the corresponding $OD_{405\ nm}$ will represent 100% lysis. The results will give us insight how much and how quickly lysis occurs in strain *L. lactis*::lytH compared to the control *L. lactis* wild-type strain. These results can be extrapolated to the minimal lysis that can be expected during 8 hours in-vivo transit. The timing when lysis is initiated is relevant to the amount of virions that will be released. A minimum of three independent experiments are performed, followed by statistical analysis of the data (Student t test, two-tailed, paired).

Integration of bilE to increase bile resistance. Increased viability of *L. lactis* during gastrointestinal transit can be obtained by increasing the cell's ability to exclude bile. This was previously achieved in *L. lactis* by cloning the bilE gene of *Listeria monocytogenes* in a high-copy plasmid under the control of its native promoter (Watson et al., 2008). To develop a biotherapeutic that is food-grade, bilE will be integrated as a single copy in the *L. lactis* chromosome thereby omitting the need to include plasmids encoding antibiotic-resistance. A fusion of the strong constitutive lactococcal P23 promoter (Que et al., 2000), the bilE gene that is codon-optimized for expression in *L. lactis*, and the lactococcal pepN inverted repeat that is known to be a strong transcriptional terminator (de Ruyter et al., 1996) is synthesized. (GeneArt® Strings™, Life Technologies). The bilE gene is integrated in an intergenic region whereby the gene upstream and downstream is in opposite orientation so any potential polar effect is minimized. The pORI19/pVE6007 system (Law et al., 1995; van Pijkeren et al., 2006) is used to integrate bilE yielding strain *L. lactis*::bilE. The integrity of the new strain is assessed by amplification of the insert by high-fidelity PCR, followed by sequence analysis.

Upon construction of *L. lactis*::bilE, the recombinant strain is assessed for increased growth and survival characteristics when exposed to bile acids compared to *L. lactis* wild-type. The same conditions as above for temperature dependent lysis, with the following modifications. Cells are harvested by centrifugation at each of the above mentioned growth stages, and pellets are resuspended in an equal volume GM17 or GM17 supplemented with either 0.2-0.4-0.6-0.8-1% porcine bile (Sigma) followed by incubation at 37° C. This range is chosen, as the physiological relevant bile concentration will vary depending, for example, on the location of the intestine and the individual's diet (Martinez-Augustin and Sanchez de Medina, 2008). Over a period of 8 hours, corresponding to a typical transit time (Padmanabhan et al., 2013), every 30 minutes, the optical density and the viability will be determined by spectrophotometric measurements and by plating a sample from each culture, respectively. A 5-10-fold increased survival of L. lactis::bilE is expected compared to L. lactis wild-type when cultured in the presence of 1% bile. A minimum of three independent experiments will be performed, followed by two-way ANOVA analysis. Following this analysis L. lactis::bilE::lytH is constructed accordingly.

In-vivo assessment of recombinant L. lactis strains. To assess whether in-vitro findings translate to in-vivo efficacy a mouse feeding study will be undertaken. Plating fecal material from mice directly on GM17 plates will yield a high number of background colonies (data not shown). In order to ensure that the colonies represent the recombinant L. lactis strains of the invention, a gene encoding antibiotic resistance is incorporated to enable selection. The gene encoding for erythromycin resistance (Em) in L. lactis wild-type and in L. lactis::bilE::lytH, and the gene encoding chloramphenicol resistance (Cm) is incorporated in the in the chromosomes of L. lactis::bilE, using the aforementioned pVE6007/pORI19 system. A variety of derivatives of pVE6007/pORI19 harboring different antibiotic markers are available. The location of integration is an intergenic region whereby the gene upstream and downstream are in opposite orientation so a potential polar effect is minimized. After confirming that the in-vitro fitness by growth rate at 30° C. is similar between the strain combinations to be tested in-vivo, the experiments outlined in the next two sections are carried out.

In-vivo fitness of L. lactis::bile. L. lactis wild-type ($Em^r$) and L. lactis::bilE ($Cm^r$) are mixed at 1:1 ratio, and 100 µl cells ($10^8$ cfu/animal) are gavaged in eight (Power analysis, power 0.9, effect size as in G*power 1) female BALB/c mice (8 weeks, Harlan Laboratories). It has been documented that the gastrointestinal transit time from oral intake to rectum can be as short as 6-7 hours while after 24 hours no material could be detected in the gastrointestinal tract (Padmanabhan et al., 2013). Thus, after gavage, fecal material from each animal is collected at 6 hours post gavage (T=6 h). Also at T=12 and T=24, fecal material is collected, which can inform us whether increased bile resistance now enables L. lactis to accumulate in-vivo that can result in prolonged persistence. Fecal pellets are resuspended in PBS, and plated on GM17-Em, GM17-Cm and GM17-Em/Cm, followed by incubation at 30° C. The ratio of $Em^+/Cm^+$ colonies will determine to what extent bilE has increased the survivability during gastrointestinal transit. It is expected that at least 10-fold more L. lactis::bilE will be recovered compared to L. lactis wild-type. Animals are kept in a specific pathogen-free facility, and receive feed and water ad libitum.

In-vivo fitness of L. lactis::bilE::lytH. An identical experiment as described in the above paragraph is performed but now using a 1:1 mixture of L. lactis::bilE ($Cm^r$) and L. lactis::bilE::lytH ($Em^r$). This is done to assess whether in-vivo passaging of L. lactis::bilE::lytH reduces the total number of viable cells recovered in feces when compared to the corresponding control. Based on viable counts, it is expected that at least 5-fold fewer colonies will be recovered for strains expressing LytH compared to the non-lytic wild-type strain. These data, combined with the in-vitro assessment of lysis by measuring PepX will confirm that L. lactis is lysing during gastrointestinal transit, and thus would release a larger therapeutic load during transit.

Construction of L. lactisΔalr::bilE::lytH. After confirmation that BilE and LytH increased bile resistance and yield a slow-lysis phenotype at 37° C., respectively, we will build a platform for therapeutic delivery that is free of antibiotic markers. The strain L. lactisΔalr will warrant stable phasmid replication. In L. lactisΔalr, lytH and bilE is inserted in intergenic regions at 3 and 4 o'clock as described above to yield L. lactisΔalr::bilE::lytH. Regular maintenance of this strain is in media supplemented with D-ala. Transformation of our food-grade phasmid will provide the auxotrophic marker alanine racemace in-trans and will thus alleviate the need to supplement D-ala to the growth media. Finally, in-vitro analyses is used to confirm that L. lactisΔalr::bilE::lytH yields identical phenotypes with regard to resistance to bile and increased lytic activity at 37° C. when compared to L. lactis::bilE and L. lactis::lytH, respectively.

Increase killing efficiency by delivery of multiple CRISPR-targets. To address the possibility of a small proportion of cells in the target bacterial population (e.g., C. difficile) surviving targeting by CRISPR-Cas, a phasmid is engineered that contains a second CRISPR cassette targeting the toxin B gene (tcdB), as well as CRISPR arrays that contain multiple targeting spacers targeting housekeeping genes.

The CRISPR-cassette (promoter-repeat-target-repeat) is incorporated in the phasmid backbone downstream of the origin of replication (ORI; see, e.g., FIG. 2B). The rationale for this approach is that a homologous recombination event between the repeat sequences of the different CRISPR-cassettes occurs, each located upstream and downstream of the ORI, would delete the ORI and shut down virion production derived from these phasmids. This approach should assist in maintaining a homogenous virion population and increasing the overall efficiency.

New phasmid variants are constructed by LCR as described above, yielding phasmid_tcdA_tcdB, and phasmid_multilocus. Virions derived from phasmid_tcdA and the two newly constructed phasmids are tested for their ability to kill C. difficile 196 in-vitro as described above. To measure the number of virion particles that are present in the supernatant, total DNA (n=6 per supernatant) is prepared from each supernatant fraction using standard approaches. By quantitative real-time PCR the number of phasmid copies present in the supernatant is determined based on standard curve analyses (BioRad, iCycler). The killing data of the different supernatants is normalized against the number of average phasmid copies present in the supernatant. At least three biological replicates are obtained, and the data analyzed by t-Test analyses (unpaired, two-tailed).

Alternative promoters and lytic constructs. An alternative promoter to prfA-UTR includes the clpP promoter whose expression is regulated by the well-characterized class-three stress gene repressor (CtsR) that is conserved in Gram-positive bacteria (Derre et al., 1999; Elsholz et al., 2010). An increase in temperature (i.e. 37° C.) induces the expression of genes involved in the stress response, including clpP (Derre et al., 2000). Further, ssDNA recombineering (van Pijkeren and Britton, 2012) can be used to generate a variety of mutations in ctsR that previously have been characterized in the highly conserved regulatory sequence (Derre et al., 2000). Complementary to this approach would be the insertion of multiple copies of lytR in the chromosome, all under the control of clpP promoter, which would increase the holin levels proportional to the number of copies present in the chromosome.

C. Determine the Efficacy of Our Recombinant *L. lactis* Strain to Treat an Active and Recurrent *C. difficile* Infection in a Humanized Murine *C. difficile* Infection Model.

Figure 5:
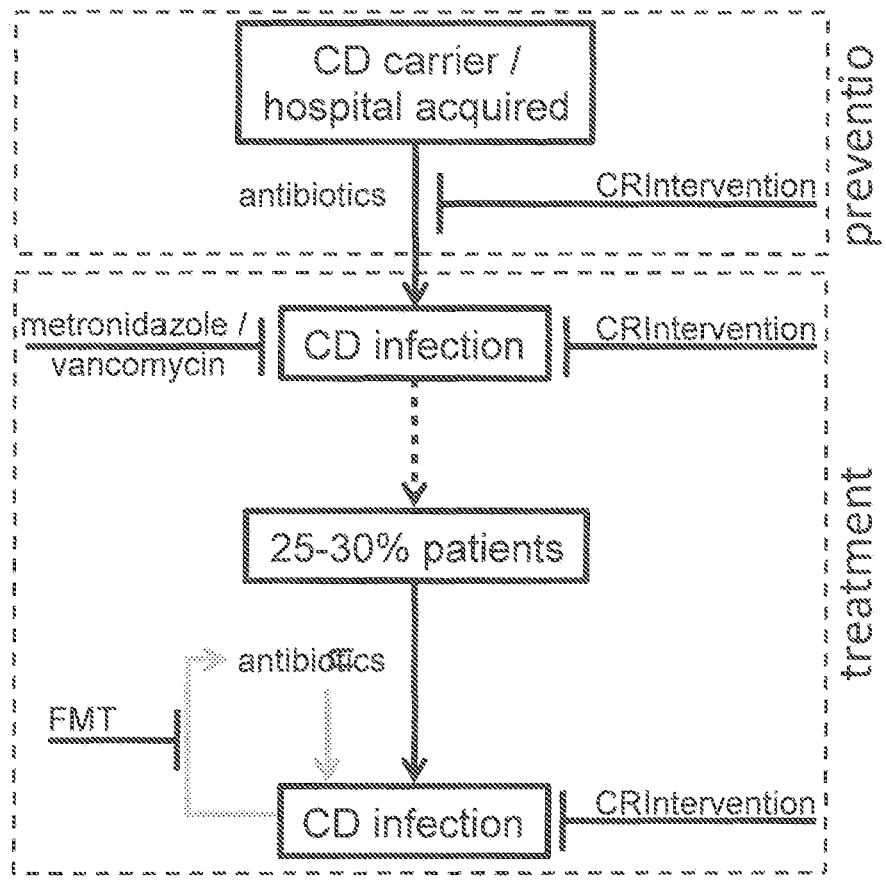
FIG. 5 is a flow chart of *C. difficile* (CD) infection highlighting the potential of engineered virions (CR intervention) for both prevention and treatment.

Antibiotics play a central role in the development of *Clostridium difficile* infection (CDI), and ironically antibiotics are mostly used to treat *C. difficile* (CD). Antibiotic-induced relapses of infection are encountered in 25-30% of the patients, which so far can only be efficiently treated by a fecal microbial transplant. Successful delivery of CRISPR-guides to CD by engineered virions (CRIntervention) may play a significant role in both prevention and treatment of this devastating disease (FIG. 5). As shown in FIG. 5, people can be carriers or can acquire CD in the hospital. Antibiotics to treat infections other than CD will wipe out a large part of the intestinal microbial community, which can lead to an active CDI. Antibiotics such as vancomycin or metronidazole may be used to treat CDI. Clearly, strategies to eliminate (antibiotic resistant) pathogens with subtle manipulation of the gut microbiota would address these concerns, and are much needed. Application of a biotherapeutic CRISPR-delivery platform of the invention (CRIntervention) in CD (and other diseases) is an example of such an approach Humanized gnotobiotic mice as a model for CD infection and relapse. Germ-free C57/B6 mice are gavaged with a mixture of human fecal material to establish $^{hm}$mice, identical as described before (Robinson et al., 2014). $^{hm}$Mice are housed in gnotobiotic isolators, and the derived progeny are subsequently housed under specific pathogen free conditions.

Figure 6:
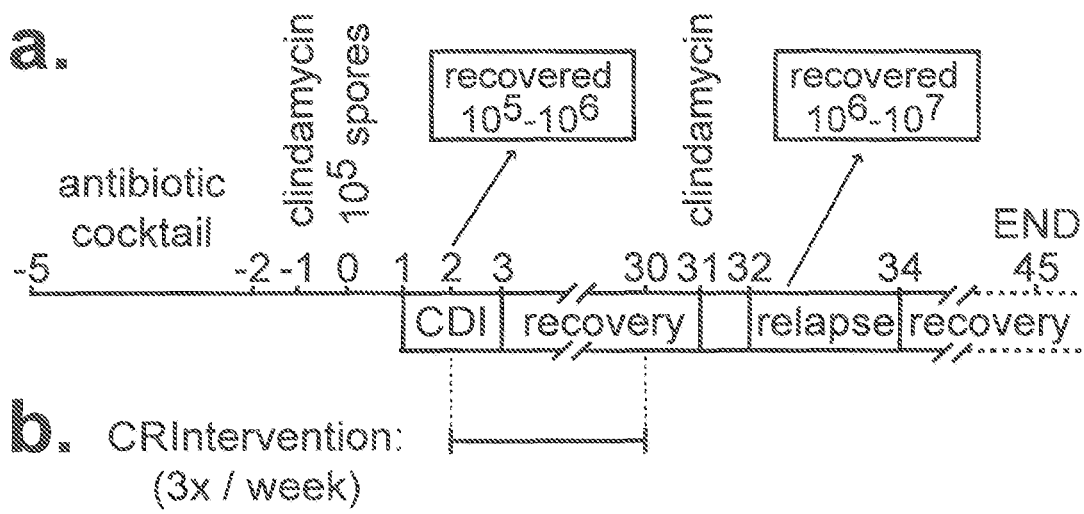
FIG. 6 shows the *C. difficile* infection/relapse model with humanized gnotobiotic mice. Panel a shows the time line of infection and Panel b shows CR intervention time points.

The layout of a novel CD infection/relapse mouse model using humanized microbiota mice ($^{hm}$mice; Collins et al., manuscript in preparation) is depicted in FIG. 6. The preparation of spores for infection, and enumeration in fecal material is performed by established protocols (Robinson et al., 2014), with the minor change that CD will be enumerated on BHI plates supplemented with 1 µg/ml erythromycin. Strain CD196 is moderately resistant to erythromycin (MIC 2 µg/ml, (Stabler et al., 2009)) while *L. lactis* is sensitive. This ensures that we do not recover *L. lactis* on plate that is biologically active, as virions may be released on plate leading to an underestimate of CD numbers due to ex-vivo killing by virion injection of CRISPR.

A mix of five antibiotics is added to the drinking water to which animal have freely access to for a period of 3 days (Chen et al., 2008): kanamycin (0.4 mg/ml), gentamicin (0.035 mg/ml), colistin (850 U/ml), metronidazole (0.215 mg/ml), and vancomycin (0.045 mg/ml), followed by a single i.p. administration of clindamycin (10 mg/kg). Animals are now reproducibly susceptible to *Clostridium difficile* infection. Mice are gavaged with $10^5$ *C. difficile* spores, and after 24 hours signs of *Clostridium difficile* infection (CDI) appear, including watery stool and weight loss. Infection is confirmed by the recovery of $10^5$-$10^6$ spores/g feces at 48-72 h after time of infection. Animals usually don't succumb to the infection but recover (day about 3-31), however, another injection of clindamycin (+31) causes a relapse in disease (similar to that observed in humans) but now with a about 10-fold increase in spores recovered, indicative for more severe CDI, after which the cycle of recovery starts again. To determine the efficacy of the recombinant *L. lactis* biotherapeutic of the invention (CRIntervention strategy), animals are gavaged ($10^8$ or $10^{10}$ recombinant *L. lactis*) beginning at +2 when CDI is active and after more than 10% weight loss has been confirmed. The animals continue to be feed 3 times/week for a period of 4 weeks. This approach allows us to monitor the effect of CRIntervention on active CDI (days 2-3), and will inform us the impact of continuous biotherapeutic supplementation on CDI relapse, a significant problem in health care. The experiment will be ended 45 days after feeding the CD spores.

CRIntervention in humanized mouse CDI and relapse model. Seven groups of animals are subjected to the CDI/relapse model as described above (FIG. 6). Each group will be housed in a separate cage, and will be treated 3 times per week for a period of 4 weeks starting at +2 (see above paragraph) by oral gavage (100 µl). The treatment groups consist of: 1) PBS control; 2) $10^8$ recombinant *L. lactis*+phasmid_ctrl; 3) $10^8$ recombinant *L. lactis*+phasmid_tcdA; 4) $10^8$ recombinant *L. lactis*,+phasmid_multilocus; 5) $10^{10}$ recombinant *L. lactis*+phasmid_ctrl; 6) $10^{10}$ recombinant *L. lactis*+phasmid_tcdA; 7) $10^{10}$ recombinant *L. lactis*+phasmid_multilocus. Starting at +1 fecal material will be collected daily to determine the level of CD. By a-priori power analysis (G*Power 3.1, (Faul et al., 2007)) for ANOVA (power=0.95, effect size [f] as in G*Power=0.4) we determined that a total sample size should be 42, thus 6 animals/group. We will obtain two biological replicates.

References

Abedon S T, Calendar R. The bacteriophages. 2nd ed. Calendar R, editor. Oxford University Press; 2005.

Alang N, Kelly C R. Weight Gain After Fecal Microbiota Transplantation. Open Forum Infect Dis. Oxford University Press; 2015 Jan. 1; 2(1):ofv004-4.

Baines S D, O'Connor R, Freeman J, Fawley W N, Harmanus C, Mastrantonio P, et al. Emergence of reduced susceptibility to metronidazole in *Clostridium difficile*. J Antimicrob Chemother. Oxford University Press; 2008 Nov. 1; 62(5):1046-52.

Barrangou R. CRISPR-Cas systems and RNA-guided interference. Wiley Interdiscip Rev RNA. John Wiley & Sons, Inc; 2013 May; 4(3):267-78.

Barrangou R, Fremaux C, Deveau H, Richards M, Boyaval P, Moineau S, et al. CRISPR provides acquired resistance against viruses in prokaryotes. Science. American Association for the Advancement of Science; 2007 Mar. 23; 315(5819):1709-12.

Bikard D, Euler C W, Jiang W, Nussenzweig P M, Goldberg G W, Duportet X, et al. Exploiting CRISPR-Cas nucleases to produce sequence-specific antimicrobials. Nat Biotech. Nature Publishing Group; 2014 Nov. 1; 32(11):1146-50.

Britton R A, Young V B. Role of the intestinal microbiota in resistance to colonization by *Clostridium difficile*. Gastroenterology. 2014 May 1; 146(6):1547-53. PMCID: PMC3995857

Bron P A, Benchimol M G, Lambert J, Palumbo E, Deghorain M, Delcour J, et al. Use of the alr gene as a food-grade selection marker in lactic acid bacteria. Appl Environ Microbiol. 2002 November; 68(11):5663-70. PMCID: PMC129899

Buist G, Karsens H, Nauta A, van Sinderen D, Venema G, Kok J. Autolysis of *Lactococcus lactis* caused by induced overproduction of its major autolysin, AcmA. Appl Environ Microbiol. 1997 Jul. 1; 63(7):2722-8. PMCID: PMC168568

Chatain-Ly M H. The factors affecting effectiveness of treatment in phages therapy. Frontiers in Microbiology. Frontiers; 2014 Feb. 18; 5.

Cho I, Blaser M J. The human microbiome: at the interface of health and disease. Nat Rev Genet. Nature Publishing Group; 2012 Apr. 1; 13(4):260-70.

Cox L M, Blaser M J. Antibiotics in early life and obesity. Nature Reviews Endocrinology. 2014 Dec. 9; 11(3):182-90.

d'Herelle F. Bacteriophage as a Treatment in Acute Medical and Surgical Infections. Bull N Y Acad Med. 1931 May; 7(5):329-48. PMCID: PMC2095997 de Kok S, Stanton L H, Slaby T, Durot M, Holmes V F, Patel K G, et al. Rapid and Reliable DNA Assembly via Ligase Cycling Reaction. ACS Synth. Biol. American Chemical Society; 2014 Jan. 15; 3(2):97-106.

de Ruyter P G G A, Kuipers O P, Meijer W C, de Vos W M. Food-grade controlled lysis of Lactococcus lactis for accelerated cheese ripening. Nat Biotech. Nature Publishing Group; 1997 Oct. 1; 15(10):976-9.

Freeman J, Bauer M P, Baines S D, Corver J, Fawley W N, Goorhuis B, et al. The Changing Epidemiology of Clostridium difficile Infections. Clin. Microbiol. Rev. American Society for Microbiology; 2010 Jul. 1; 23(3): 529-49.

Frese S A, Hutkins R W, Walter J. Comparison of the Colonization Ability of Autochthonous and Allochthonous Strains of Lactobacilli in the Human Gastrointestinal Tract. Advances in Microbiology. Scientific Research Publishing; 2012 Sep. 24; 02(03):399-409.

Gomaa A A, Klumpe H E, Luo M L, Selle K, Barrangou R, Beisel C L. Programmable Removal of Bacterial Strains by Use of Genome-Targeting CRISPR-Cas Systems. mBio. American Society for Microbiology; 2014 Feb. 28; 5(1):e00928-13.

He M, Miyajima F, Roberts P, Ellison L, Pickard D J, Martin M J, et al. Emergence and global spread of epidemic healthcare-associated Clostridium difficile. Nat Genet. Nature Publishing Group; 2013 Jan. 1; 45(1):109-13.

Horvath P, Barrangou R. CRISPR/Cas, the immune system of bacteria and archaea. Science. 2010 Jan. 8; 327(5962): 167-70.

Jiang W, Bikard D, Cox D, Zhang F, Marraffini L A. RNA-guided editing of bacterial genomes using CRISPR-Cas systems. Nat Biotech. 2013 Mar. 1; 31(3):233-9.

Lewis K. Platforms for antibiotic discovery. Nature Reviews Drug Discovery. Nature Publishing Group; 2013 May 1; 12(5):371-87.

Ley R E, Backhed F, Turnbaugh P, Lozupone C A, Knight R D, Gordon J I. Obesity alters gut microbial ecology. Proc Natl Acad Sci USA. 2005 Aug. 2; 102(31):11070-5. PMCID: PMC1176910

Makarova K S, Haft D H, Barrangou R, Brouns S J J, Charpentier E, Horvath P, et al. Evolution and classification of the CRISPR-Cas systems. Nat Rev Microbiol. 2011 Jun. 1; 9(6):467-77. PMCID: PMC3380444

Mali P, Esvelt K M, Church G M. Cas9 as a versatile tool for engineering biology. Nat Meth. 2013 October; 10(10): 957-63.

Merrigan M, Venugopal A, Mallozzi M, Roxas B, Viswanathan V K, Johnson S, et al. Human hypervirulent Clostridium difficile strains exhibit increased sporulation as well as robust toxin production. Journal of Bacteriology. 2010 Oct. 1; 192(19):4904-11. PMCID: PMC2944552

Nicoletti M, Bertani G. DNA fusion product of phage P2 with plasmid pBR322: A new phasmid. Mol Gen Genet. Springer-Verlag; 1983 Mar. 1; 189(2):343-7.

Oh J-H, van Pijkeren J-P. CRISPR-Cas9-assisted recombineering in Lactobacillus reuteri. Nucleic Acids Research. Oxford University Press; 2014 Jan. 1; 42(17):e131-1. PMCID: PMC4176153

Piekarowicz A, Klyz A, Majchrzak M, Szczesna E, Piechucki M, Kwiatek A, et al. Neisseria gonorrhoeae filamentous phage Ngo D6 is capable of infecti . . . —PubMed—NCBI. J. Virol. 2013 Dec. 30; 88(2):1002-10. PMCID: PMC3911633

Powledge T M. New Antibiotics—Resistance Is Futile. PLoS Biol. 2004; 2(2):e53.

Rea M C, Alemayehu D, Ross R P, Hill C. Gut solutions to a gut problem: bacteriocins, probiotics and bacteriophage for control of Clostridium difficile infection. 2013 Sep. 1; 62(Pt 9):1369-78.

Ridaura V K, Faith J J, Rey F E, Cheng J, Duncan A E, Kau A L, et al. Gut Microbiota from Twins Discordant for Obesity Modulate Metabolism in Mice. Science. American Association for the Advancement of Science; 2013 Sep. 6; 341(6150):1241214.

Russell S L, Gold M J, Hartmann M, Willing B P, Thorson L, Wlodarska M, et al. Early life antibiotic-driven changes in microbiota enhance susceptibility to allergic asthma. EMBO Rep. 2012 May; 13(5):440-7. PMCID: PMC3343350

Ryan E M, Gorman S P, Donnelly R F, Gilmore B F. Recent advances in bacteriophage therapy: how delivery routes, formulation, concentration and timing influence the success of phage therapy. Journal of Pharmacy and Pharmacology. 2011 Jul. 6; 63(10):1253-64.

Sekulovic O, Garneau J R, Neron A, Fortier L C. Characterization of temperate phages infecting Clostridium difficile isolates of human and animal origins. Appl Environ Microbiol. American Society for Microbiology; 2014 Mar. 25; 80(8):2555-63. PMCID: PMC3993186

Sekulovic O, Meessen-Pinard M, Fortier L C. Prophage-Stimulated Toxin Production in Clostridium difficile NAP1/027 Lysogens. Journal of Bacteriology. American Society for Microbiology (ASM); 2011 May 12; 193(11): 2726-34.

Stockdale S R, Mahony J, Courtin P, Chapot-Chartier M-P, van Pijkeren J-P, Britton R A, et al. The lactococcal phages Tuc2009 and TP901-1 incorporate two alternate forms of their tail fiber into their virions for infection specialization. Journal of Biological Chemistry. 2013 Feb. 22; 288(8):5581-90. PMCID: PMC3581408

Tyson G W, Banfield J F. Rapidly evolving CRISPRs implicated in acquired resistance of microorganisms to viruses. Environ Microbiol. Blackwell Publishing Ltd; 2008 Jan. 1; 10(1):200-7.

van Kranenburg R, de Vos W M. Characterization of multiple regions involved in replication and mobilization of plasmid pNZ4000 coding for exopolysaccharide production in Lactococcus lactis. Journal of Bacteriology. American Society for Microbiology (ASM); 1998 October; 180(20): 5285-90. PMCID: PMC107574 van Pijkeren J-P, Britton R A. High efficiency recombineering in lactic acid bacteria. Nucleic Acids Research. 2012 May 1; 40(10):e76. PMCID: PMC3378904 van Pijkeren J-P, Britton R A. Precision genome engineering in lactic acid bacteria. Microb Cell Fact. BioMed Central Ltd; 2014 Aug. 29; 13 Suppl 1:S10-0. PMCID: PMC4155826 van Pijkeren J-P, Morrissey D, Monk I R, Cronin M, Rajendran S, O'Sullivan G C, et al. A novel Listeria monocytogenes-based DNA delivery system for cancer gene therapy. Hum. Gene Ther. 2010 April; 21(4):405-16.

van Pijkeren J-P, Neoh K M, Sirias D, Findley A S, Britton R A. Exploring optimization parameters to increase ssDNA recombineering in *Lactococcus lactis* and *Lactobacillus reuteri*. Bioengineered. 2012 Jul. 1; 3(4):209-17. PMCID: PMC3476877 van Pijkeren J-P, Ryan K A, Li Y, Claesson M J, Sheil B, Steidler L, et al. Comparative and functional analysis of sortase-dependent proteins in the predicted secretome of *Lactobacillus salivarius* UCC118. Appl Environ Microbiol. 2006 June; 72(6):4143-53. PMCID: PMC1489637

Weingarden A R, Chen C, Bobr A, Yao D, Lu Y, Nelson V M, et al. Microbiota transplantation restores normal fecal bile acid composition in recurrent *Clostridium difficile* infection. Am J Physiol Gastrointest Liver Physiol. American Physiological Society; 2014 Feb. 15; 306(4): G310-9. PMCID: PMC3920123

World Health Organization. Antimicrobial resistance: global report on surveillance. World Health Organization; 2014.

Example 2

Colorectal cancer (CRC) is the third most common cancer worldwide, accounting for up to 9% of all cancer cases 10. In 2015 it is predicted that in the US alone, 130,000 people will be diagnosed with CRC11. Although the etiology of CRC is mostly unknown, people suffering from ulcerative colitis and Crohn's disease are at increased risk, as chronic intestinal inflammation is known to alter the host physiology to promote CRC (Rubin et al. *Front Immunol* 2012, 3, 107; Arthur et al. *Science* 2012, 338, 120-123). Recent findings provide a strong connection between microbial dysbiosis and the development of colorectal adenomas and CRC (Pagnini et al. *J. Clin. Gastroenterol.* 2011, 45, 602-610; Shen. *Gut Microbes* 2010, 1, 138-147; Geng et al. *Gut Pathog* 2014, 6, 26). Specifically, when comparing human-derived CRC and normal tissues, CRC tissues clearly have an increased abundance of *Fusobacterium nucleatum* (Fn), a Gram-negative intracellular pathogen (Castellarin et al. *Genome Res* 2012, 22, 299-306; Tahara et al. *Cancer Res* 2014, 74, 1311-1318; McCoy et al. *PLoS ONE* 2013, 8, e53653 DOI: 10.1371/journal.pone.0053653; Warren et al. *Microbiome* 2013, 1, 16). In APCmin/+ mice, which carry a mutation in the apc gene leading to multiple intestinal neoplasia (Min), Fn leads to a significant increase in tumor development and inflammation compared to control animals (Kostic et al. *Cell Host & Microbe* 2013, 14, 207-215. Elegant work by Rubinstein et al. (*Cell Host & Microbe* 2013, 14, 195-206) demonstrated that the Fn surface protein FadA, required for adhesion and invasion of Fn, plays a key role in these events. Purified FadA increases CRC growth and induces inflammation (Id.). Also, patients with CRC have elevated fadA gene expression levels compared to non-CRC tissue suggesting increased Fn virulence in CRC cells. Collectively, these studies have unequivocally shown that a specific member of the human microbiota promotes intestinal tumor growth. Given the fact that Fn may constitute up to about 90% of the tumor microbiota (Kostic et al. *Genome Res* 2012, 22, 292-298), eradication of this pathogen from tumor cells is expected to both reduce inflammation and halt Fn-induced tumor growth. Because Fn elicits proinflammatory stimuli, it is also expected that prophylactic removal of Fn would benefit the host.

This invention is directed to a biotherapeutic platform to kill Fn by hijacking the cell's native adaptive immune system, CRISPR-Cas (Clustered, Regularly Interspaced Short Palindromic Repeats, and accompanying CRISPR-Associated sequences) (Horvath Science 2010, 327, 167-170; Barrangou, R. Wiley *InterdiscipRev RNA* 2013, 4, 267-278). The invention provides engineered virions, released by *Lactobacillus reuteri*, inject a CRISPR guide in Fn to yield a transcript that together with native Cas causes self destruction of the Fn cells. The invention is anticipated to have a broad translational impact in the prevention and treatment of a wide range of bacterial diseases.

For example, CRISPR-Cas systems and bacteriophages have been identified in many bacterial pathogens whose genomes have been sequenced, which we expect can be exploited in our approach for preventing or treating bacterial infections. Also, our approach eliminates the need for antibiotics and is therefore expected to be of importance in addressing problems associated with antibiotic use.

Figure 7:
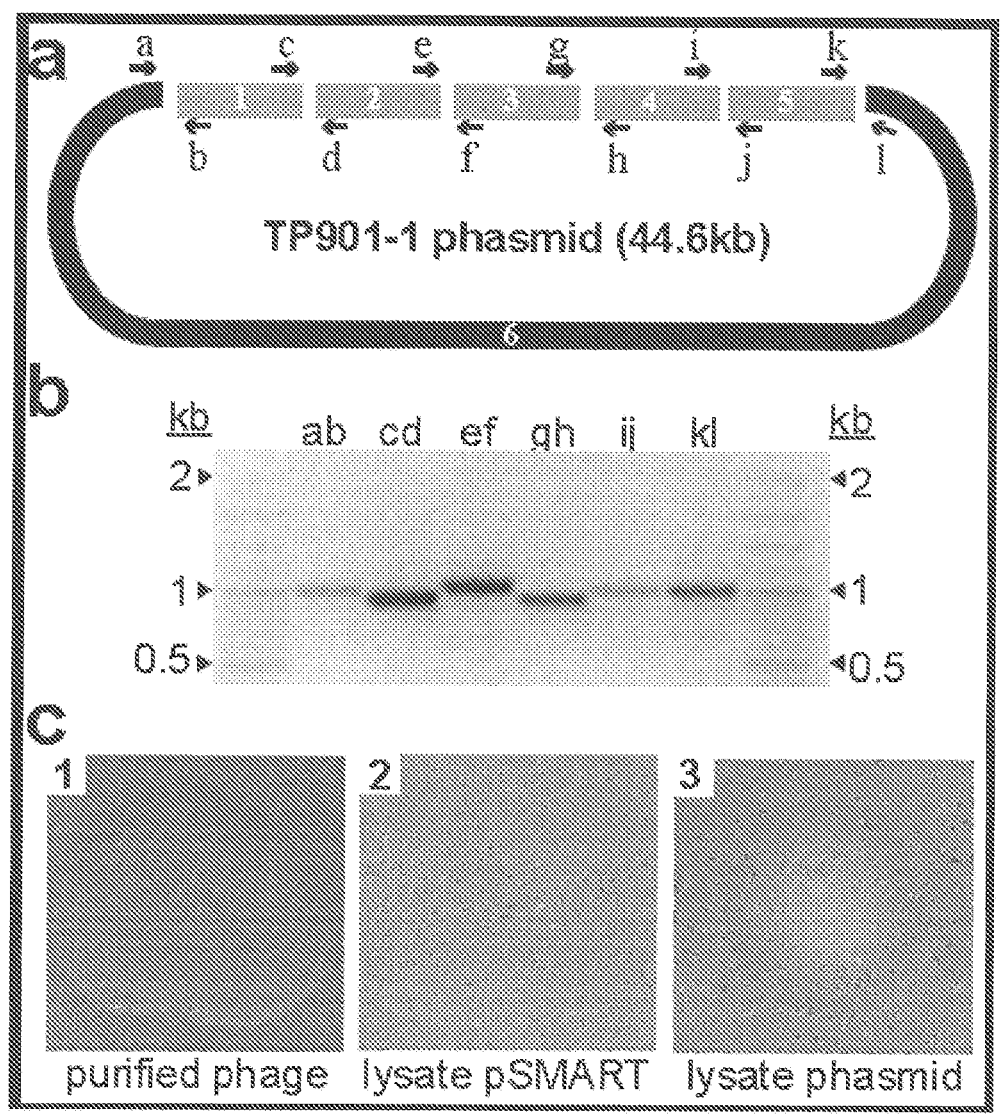
FIG. 7 shows that de-novo assembly of an exemplary 44.6 kb phasmid yielding functional virions. Panel a: six amplicons were assembled corresponding to the *L. lactis* bacteriophage sequence TP901-130 (amplicon 1-5) and the vector backbone pSMART BAC (Lucigen; amplicon 6). The bacteriophage amplicons were 7.8 kb (fragment 1), 7.9 kb (fragments 2-3), 8.4 kb (fragment 4) and 5 kb (fragment 5) totaling 37.5 kb. Amplicon 6 corresponds to the pSMART BAC vector. Panel b shows confirmation by PCR of assembly of a representative correctly assembled clone. Panel c provides confirmation that the phasmid yields active virions. Panel c1 is purified TP901-1 phage, Panel c2 is lysate derived from *E. coli* harboring control plasmid pSMART (empty vector) and Panel c3 is lysate derived from *E. coli* harboring the TP901-1 phasmid.

An exemplary biotherapeutic delivery vehicle of the invention is shown in FIG. 1 in which a recombinant *L. reuteri* host bacterium comprises a phasmid in which the DNA of a pathogen-derived bacteriophage is fused with a plasmid origin of replication (ORI), a *L. reuteri* auxotrophic marker, and a CRISPR-cassette. The auxotrophic marker on the phasmid, when deleted on the *L. reuteri* chromosome, yields stable maintenance of the phasmid. The CR reproduces in *L. reuteri* virions that contain an engineered CRISPR-array in their genome. Optional expression of the internalin A protein by *L. reuteri* allows the delivery vehicle to localize intracellularly for subsequent virion release. This allows targeting invasive pathogens, such as *Fusobacterium nucleatum*. Our approach to achieve programmed release of the virions includes such methods as temperature-controlled expression of a phage lytic protein (holin and/or lysin). When, for example, the mesophilic *L. reuteri* is cultured at 30° C., a secondary structure (hairpin loop) at the ribosomal binding site (RBS) blocks translation, while incubation at body temperature (37° C.) dissociates the structure, thereby making the RBS accessible for translation to yield the holin/lysin polypeptides and subsequent lysis of *L. reuteri*. The onset of lysis occurs several hours after the temperature shift, which allows therapeutic delivery in, for example, the gastrointestinal (GI) tract. Lysis will thus release the virions in situ. Complete lysis is also a robust approach to achieve biological containment—another added advantage of the present invention. The released virions inject their DNA in the pathogens. Transcription of the phasmid encoded CRISPR-array will, combined with the native Cas-nuclease of the pathogen, yield killing in a strain-, species-, or genus-specific manner A. Phasmid construction: Six amplicons corresponding to the *L. lactis* bacteriophage sequence TP901-130 (amplicon 1-5) and the vector backbone pSMART BAC (Lucigen; amplicon 6) were assembled to generate the phasmid TP901-1 (FIG. 7). The bacteriophage amplicons were 7.8 kb (fragment 1), 7.9 kb (fragments 2-3), 8.4 kb (fragment 4) and 5 kb (fragment 5) totaling 37.5 kb. Amplicon 6 corresponds to the pSMART BAC vector. All clones (5) tested were confirmed to be assembled correctly (FIG. 7, Panel b) Oligonucleotide pairs (ab, cd, of etcetera) are indicated on top of the gel in FIG. 7, Panel b. Each primer was located on the proximal end of each adjacent fragment, as indicated in Panel a, to confirm assembly. All amplicons had the expected size, which was between 941 bp (oligo pair 'cd') and 1051 bp (oligo 'ef'). The water controls were all negative and the positive controls using TP901-1 DNA (cd, ef, gh, ij) all yielded amplicons of the same size, while no amplicon was generated with 'ab' and 'kl'. Confirmation that the phasmid yields active virions is provided in FIG. 7, Panel c. We hypothesized that if virions were produced from the TP901-1 phasmid, small amounts should be present in the supernatant as a small sub-population of bacterial cells lysed during growth. Filter-sterilized supernatants (5 ml) of *E. coli* harboring pSMART vector or the phasmid were precipitated and eluted in water (200 µl). Using the agar overlay technique, the lytic host for TP901-1, *L. lactis* 3107, was poured on top of the bottom agar. On solidified plates, we spotted 10 µl of purified TP901-1 phage (FIG. 7, Panel c1), lysate derived from *E. coli* harboring control plasmid pSMART (empty vector) (FIG. 7, Panel c2) and lysate derived from *E. coli* harboring the TP901-1 phasmid (FIG. 7, Panel c3). Thus, FIG. 7, Panel c shows that the TP901-1 phasmid yields functional virions.

B. Distribution CRISPR-Cas: Bioinformatics analysis revealed that CRISPR-Cas is conserved in *F. nucleatum* strains (Table 1, below), which supports our approach to use the native Cas nuclease to induce cell killing upon delivery of the CRISPR-array. Using the CRISPRdb web server (crispr.u-psud.fr), we identified CRISPR-Cas systems in Fn and determined the type of CRISPR repeat along with the number of spacers that had been acquired. Based on the type of cas genes present, the CRISPR subtype was determined. For mechanism of action of Type-I CRISPR-Cas see FIG. 2A.

e37116). A clinical study showed that *L. reuteri* 6475 survives passage through the human GI tract (Frese et al. *Advances in Microbiology* 2012, 02, 399-409), and the murine GI tract (Oh et al. *ISME J* 2010, 4, 377-387), which is important for in situ delivery of a therapeutic load.

Moreover, *Lactobacillus reuteri* is genetically amenable. Thus, for example, single stranded DNA recombineering (SSDR) has been applied successfully in lactic acid bacteria, including *L. reuteri* (van Pijkeren et al.; *Nucleic Acids Research* 2012, 40, e76 DOI: 10.1093/nar/gks147). SSDR enables incorporation of an oligonucleotide in the chromosome to yield subtle base changes. This is a powerful approach to edit RBS, promoters, and DNA coding for active sites to optimize therapeutic efficacy (van Pijkeren et al. *Bioengineered* 2012, 3, 209-217; van Pijkeren et al. *Microb Cell Fact* 2014, 13 *Suppl* 1, S10-S10). Recent work shows successful application of CRISPR-Cas genome editing in *L. reuteri* (Oh et al. *Nucleic Acids Research* 2014, 42, e131-e131), and allows the identification of low-efficiency mutagenesis events. Collectively, the features of *L. reuteri* such as its ability to survive GI passage, high natural genetic stability, probiotic characteristics, and the fact that the present inventors have developed high-throughput technologies to engineer this strain makes *L. reuteri* an ideal platform to be developed as a biotherapeutic delivery-vehicle to promote human health.

TABLE 1

Overview of the CRISPR-Cas systems in Fusobacterium nucleatum (Fn) strains.

| Fn strain | Repeat | Lenght (bp) | # spacers | CRISPR subtype |
|---|---|---|---|---|
| subsp animalis 7_1 | ATGAACTAAAAACTTGAAAAGTTTTGAAAT | 30 | 19 | I-B |
| subsp nucleatum ATCC 25586 | ATTTAAATTCTAATATAGAAATACATAAAT | 30 | 17 | I-B |
| subsp polymorphum ATCC 10953 | ATTTATGTATTTCTATATTAGAATTTAAAT | 30 | 29 | I-B |
| subsp Vincentii 3_1_36A2 | GTTTGAGAGTAATGTTATTTTAAATAGATTCAAAAC | 36 | 19 | II-A |
| sp. 4_8 | ATGAACTGTAAACTTGAAAAGTTTTGAAAT | 30 | 53 | I-B |

Also, we confirmed that CRISPR-Cas is widely distributed in a large number of bacteria, among which are *S. aureus, C. difficile, S. pneumoniae, Salmonella, C. botulinum* and *L. monocytogenes*. This, in addition to the bacteriophages that have been identified for these pathogens (M. Deghorain *Viruses* 2012, 4, 3316-3335; Sekulovic et al. *Appl Environ Microbiol* 2014, 80, 2555-2563; Ronda et al. *J. Virol.* 1981, 40, 551-bau082; De Lappe et al. *J. Med. Microbiol.* 2009, 58, 86-93; Carlton et al. *Regul. Toxicol. Pharmacol.* 2005, 43, 301-312), emphasizes that this invention is widely applicable. The invention does not require lytic phages, as only injection of the CRISPR is required, and it allows bacterial killing in a strain-specific manner.

Figure 8:
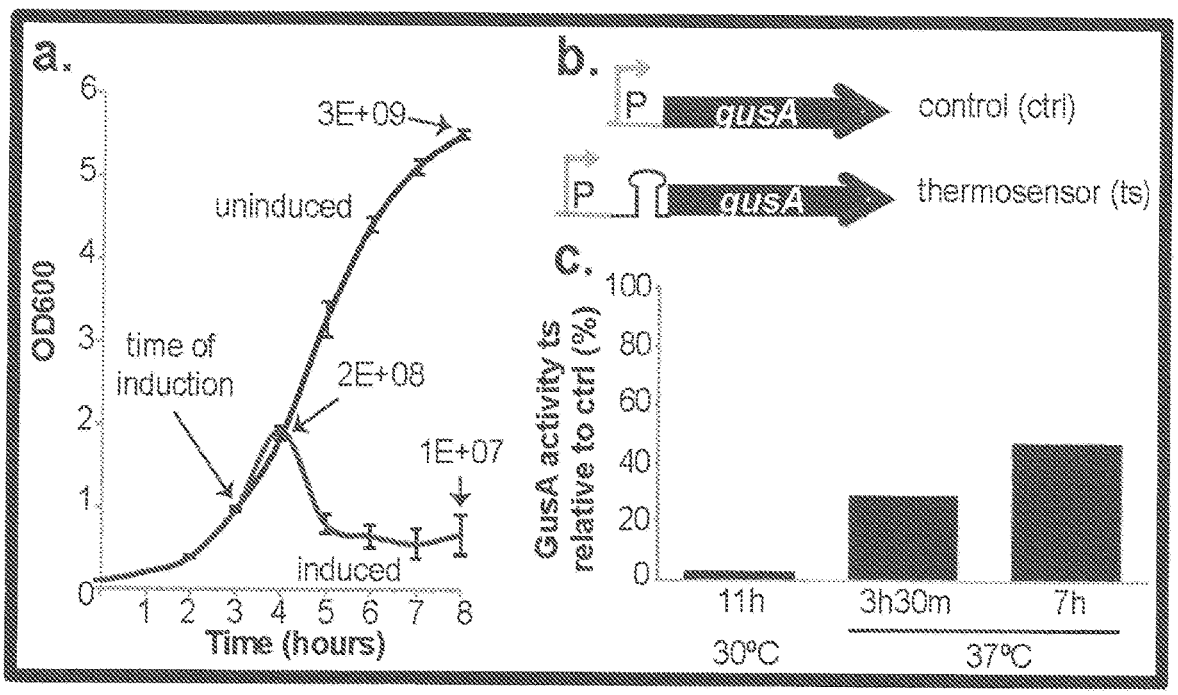
FIG. 8 shows induced lysis and applicability of a thermosensor in *L. reuteri*. Panel a shows expression of a bacteriophage-derived holin lyses *L. reuteri* (grey line) killing 95% of the population. Average viability levels are indicated; Panel b provides an overview of the gusA constructs to assess functionality of a thermosensor; Panel c shows that shifting the temperature from 30° C. to 37° C. increased GusA activity, thereby confirming functionality of the thermosensor. Data shown are averages of three experiments, and error bars indicate standard deviation.

C. Advantages of *Lactobacillus reuteri* as a biotherapeutic platform: The *L. reuteri* strain in this example is a direct derivative of the human milk isolate *L. reuteri* ATCC PTA 6475. It is an undomesticated strain (about 15 passages since original isolation) with probiotic features, which include anti-inflammatory properties (Thomas et al. *PLoS ONE* 2012, 7, e31951 DOI: 10.1371/journal.pone.0037116.g006; Liu et al. *Am J Physiol Gastrointest Liver Physiol* 2010, 299, G1087-G1096), prevention of bone loss (Britton et al. *J Cell Physiol* 2014, 229), amelioration of infection by pathogenic *E. coli* (Eaton et al. *Infect Immun* 2011, 79, 185-191), and in the presence of glycerol the strain produces the antimicrobial molecule reuterin (De Weirdt et al. *PLoS ONE* 2012, 7, D. Induced lysis and thermoregulation: Lysis is needed to release the biotherapeutic virions of the invention in-situ. Induced lysis has been demonstrated in *Lactococcus lactis* by expression of 'lytic' genes derived from the virulent *L. lactis* bacteriophage US352. To date, no *L. reuteri* 6475 bacteriophages have been characterized. Therefore, we investigated whether *L. reuteri* 6475 has prophages in its genome, which could be a source for lytic genes to induce lysis. The phage search tool (PHAST) (Zhou et al. PHAST: A Fast Phage Search Tool. 2011, 39, W347-W352 DOI: 10.1093/nar/gkr48) revealed the presence of four prophages of which two are predicted to be intact. In one of the intact phages a holin-endolysin cassette was identified, which are typically employed by bacteriophages to achieve host lysis. Holins are small proteins that are incorporated in the bacterial membrane to lead to an increased permeability. The endolysin protein then has access to the peptidoglycan for subsequent degradation of the cell wall. Prolonged and heterologous induced expression of holins alone do induce lysis (de Ruyter et al. Nat Biotech 1997, 15, 976-979; Shi et al. *Virol J* 2012, 9, 70-70) as a consequence of increased membrane permeability, possibly combined with the presence of native endonucleases. We cloned the holin gene in the inducible expression vector pSIP55, and confirmed induced lysis in *L. reuteri* (FIG. 8, Panel a). These data confirm that lysis can be induce in *L. reuteri* that can be further optimized and exploited for efficient local therapeutic release.

Lysis should occur gradually over time, allowing release of the therapeutic load during GI transit. In mice, which will be our in-vivo model, it takes 6-8 hours to reach the colon after gavage (Padmanabhan et al. *EJNMMI Research* 2013, 3, 60). The current inducible expression systems in *L. reuteri* (Sorvig et al. *FEMS Microbiol Lett* 2003, 229, 119-126; Wu et al. *Biosci Biotechnol Biochem* 2006, 70, 757-767) require the addition of an exogenously added molecule to induce expression, which is not a practical approach for in-vivo expression due to, for example, lack of bioavailability and stability of the inducer molecules, especially intracellular inducer molecules. An alternative approach can be application of a thermosensor that can regulate gene expression (Johansson et al. *Cell Regen* 2002, 110, 551-561). The basis for this is that at low temperatures the mRNA sequence in the 5' untranslated region forms a secondary structure, which blocks the Shine-Dalgarno sequence from binding to the ribosome, and thus translation will not occur. At elevated temperatures, the secondary structure resolves, leading to translation. Neupert developed de-novo simple thermosensors for use in *E. coli* (*Nucleic Acids Research* 2008, 36, e124-e124), and we confirmed that the application of a thermosensor in the mesophilic *L. reuteri* is a realistic approach to regulate gene expression (FIG. 8, Panel b; FIG. 8, Panel c).

As shown in FIG. 8, Panel a, expression of a bacteriophage-derived holin lyses *L. reuteri* (grey line), killing 95% of the population. *L. reuteri* cells harboring pSIP-holin (FIG. 8, Panel b) were cultured overnight, diluted to OD600=0.1 and at OD600=1, the culture was split, and one culture was induced for holin expression. A constitutive *L. reuteri* promoter was cloned upstream of gusA (control), while a second construct contained the thermosensor U6 (Neupert et al. *Nucleic Acids Research* 2008, 36, e124-e124) as indicated by the hairpin loop (FIG. 8, Panel b); The control and temperature sensitive (ts) cultures were grown overnight at 30° C., sub-cultured to OD600=0.05 and grown at 30° C. and 37° C. At 30° C., GusA levels were only 2% for ts compared to the control, while prolonged incubation at 37° C. increased GusA levels for the ts culture relative to the control, confirming temperature-regulated induction of expression.

E. Assemble a phasmid that replicates in LR, and produces virions that kill *Fusobacterium nucleatum* (Fn) by CRISPR-delivery: Native Cas nucleases will be exploited for self-destruction of *Fusobacterium nucleatum*. Following methods described in Example 1, section A, for targeting of *C. difficile*. Ligation cycle reaction (LCR) is used to generate a food-grade phasmid that replicates in *L. reuteri*, which includes DNA encoding a crRNA guide that will direct the endogenous Type-I-B CRISPR-Cas system cascade machinery towards the chromosome of Fn.

Amplification and synthesis of phasmid components. The genome sequence of *Fusobacterium* phage Funu1 has been sequenced (www.ebi.ac.uk/ena/data/view/KR131710). It uses as a host the tumorigenic strain *F. nucleatum* 7/1. With the PHAge Search Tool (PHAST) (Zhou et al. PHAST: A Fast Phage Search Tool. 2011, 39, W347-W352 DOI), we determined that the region 3495-36452 (33 kb) encodes all ORFs required for the phage head morphogenesis, tail morphogenesis, and DNA packaging to generate virions that can inject DNA into the Fn target organisms. Seven 4.7 kb fragments are synthesized that collectively make up the 33 kb phage. Also, the CRISPR-cassette targeting the *Fusobacterium* adhesin A (fadA), and the Grampositive origin of replication (ORI)67 are synthesized (GeneArt® Strings™, Life Technologies). The auxotrophic marker thymidylate synthase (thyA), including promoter, is amplified from *L. reuteri* 6475. The pSMART® BAC vector system is obtained from Lucigen.

In-vitro assembly of the phasmid using *E. coli* as a cloning host. Although purified plasmids and conventional ligations can be transformed effortlessly in *L. lactis*, *E. coli* is preferred when transforming assemblies obtained by ligation cycle reaction (LCR) due to the superior transformation efficiency of *E. coli*, which is 1000-fold higher when using ultra-competent cells. Therefore, *E. coli* is used as the intermediate cloning host, followed by electroporation of purified phasmid in *L. reuteri*. All the different components are assembled in the pSMART® BAC vector system to allow replication in *E. coli*. We have previously shown that LCR can be used to generate plasmids of 30 kb with the pSMART® BAC vector system. Once assembled, the full size phasmid is isolated using the QIAfilter Plasmid kit (Qiagen), which supports purification of plasmids up to about 50 kb.

Figure 9:
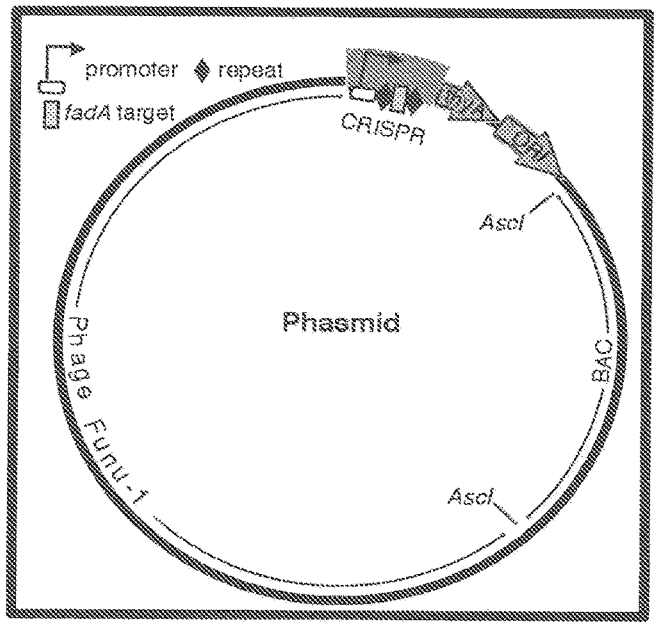
FIG. 9 shows an exemplary phasmid for specific targeting of the bacterium, *F. nucleatum*.

The phasmid that supports replication in *E. coli* is assembled by LCR29. DNA fragments of each about 8 kb are synthesized, corresponding to phage Funu-1. The synthetic CRISPR array (grey trapezoid shape) consists of a promoter, and a repeat-spacer-repeat sequence. The genome sequence of E *nucleatum* 7_1 is used as a template for design. The spacer sequence corresponds to the *Fusobacterium* adhesin A (fadA) that is conserved in clinical isolates of E *nucleatum*. The CRISPR-cassette, the gene encoding thymidylate synthase (thyA), and the Gram-positive origin of replication (ORI) By PCR will be fused to yield a single amplicon. Thymidylate synthase is an auxotrophic marker that will provide selection for the phasmid in *L. reuteri*ΔthyA. Notably, the ORI has been previously characterized and supports replication of a 40 kb plasmid in a Gram-positive host (van Kranenburg et al. *Journal of Bacteriology* 1998, 180, 5285-5290). Two PCR amplicons are generated corresponding to the pSMART® BAC vector. The flanks of the pSMART BAC vector have a AscI restriction recognition site included, which allow removal of the pSMART backbone. The different fragments are subjected to a LCR reaction, as previously described (de Kok et al. *ACS Synth. Biol.* 2014, 3, 97-106), followed by electroporation in ultra-competent BAC-Optimized Replicator™ v2.0 Electrocompetent Cells (Lucigen). A control phasmid is constructed that does not contain a CRISPR-sequence targeting Fn. Integrity of constructs will be verified by PCR and Sanger sequencing analysis. FIG. 9 shows an exemplary phasmid for specific targeting of the pathogenic bacterium, *F. nucleatum*.

Establishing the phasmid in *L. lactis*Δalr. The essential thyA gene as a selection marker in an analogous manner as described for *L. acidophilus* (Fu et al. *Microbiol Immunol* 2000, 44, 551-556). By CRISPR-Cas-assisted recombineering technology (Oh et al. *Nucleic Acids Research* 2014, 42, e131-e131), the thyA gene is deleted to yield *L. reuteri*ΔthyA, which makes the cells dependent on exogenously added thymidine. *L. reuteri*ΔthyA can be used as host to stably maintain phasmids that encode ThyA from their backbone, which omits the need for antibiotic selection. For replication in *L. reuteri*Δalr the backbone of pSMART BAC becomes obsolete, and therefore this backbone is removed. AscI restriction digest, followed by self-ligation yields a 35 kb phasmid (phasmid_tcdA and phasmid_ctrl). The phasmids are transformed in *L. reuteri*ΔthyA.

Cells are plated on regular MRS-agar plates, and colonies that are obtained after electroporation are expected to contain phasmid_fadA or phasmid_ctrl as it provides the thymidine synthase enzyme in-trans that allow the *L. reuteri*ΔthyA cells to grow in the absence of exogenously added thymidine. Colonies are screened by PCR analysis to confirm the presence of each phasmid.

Testing the supernatant of *L. reuteri*ΔthyA harboring phasmid_fadA for killing activity of Fn. We have shown that expression of a *L. reuteri* phage holin causes lysis of *L. reuteri*. *L. reuteri*ΔthyA harboring phasmid_fadA or phasmid_ctrl are transformed with vector pSIPholin, which contains the holin gene under the control of an inducible promoter, and at mid-logarithmic phase, expression of the holin enzyme is induced to yield lysis and thus release of the virions in the supernatant. The lysate of *L. reuteri*ΔthyA cells harboring phasmid_fadA or phasmid_ctrl, respectively, is collected followed by neutralizing the pH to 7 with NaOH, and filter sterilization (0.45 µm).

To show that the produced virions are functional in their ability to kill Fn by injecting the CRISPR-fadA the clinical isolate Fn 7_1, host of phage Funu-1, will be used. Fn will be cultured in our anaerobic chamber at 37° C. to mid-logarithmic phase in Tryptic Soy Broth (TSB) supplemented with 5 µg/mL hemin, 1 µg/mL menadione (Sigma Aldrich), and diluted to $10^4$ cells/ml. Supernatants containing phasmid_fadA or phasmid_ctrl will be added to Fn cultures, followed by assessment of Fn viability in a time-course experiment. A minimum of three biological replicates are obtained and samples are analyzed by a paired t-test.

Fn numbers are expected to be reduced by at least 2-orders of magnitude. The ability to construct phasmids by LCR exemplifies the potential to use synthetic biology approaches to generate a variety of phasmids, each producing virions targeting different bacterial strains, in a high-throughput manner. The native Cas endonuclease of Fn should act on the CRISPR-fadA delivered by the engineered virion, inducing self-destruction. It is appealing to capitalize on the native Cas nuclease as it may increase the efficacy of cell killing compared to introduction of heterologous cas. However, introduction of heterologous cas is a further aspect of this invention and may be advantageous, in particular, when no native CRISPR-cas system is identified for a particular target bacterial population.

F. Optimize biotherapeutic efficacy: The probiotic-based platform of this invention allows modification of the microbiota in a strain specific manner. The efficacy of the invention relies on: 1) timely release of the virions; 2) the efficacy of virion release; 3) the number of CRISPR-arrays delivered; and 4) can intracellular location of *L. reuteri* when targeting an invasive bacteria.

Intracellular delivery of engineered virions is achieved upon programmed lysis of *L. reuteri* which, combined with delivery of multiple CRISPR targeting guides, will collectively enhance the biotherapeutic efficacy of the engineered virions to eradicate *F. nucleatum*. For this example, a thermosensor fused to a lysin gene is integrated into the *L. reuteri* chromosome, and intracellular accumulation of *L. reuteri* is established by insertion of the *L. monocytogenes* internalin A gene. In addition, a phasmid can be constructed to comprise multiple CRISPR repeat-spacers units.

Increase killing efficiency by delivery of multiple CRISPR-targets In order to maintain a homogenous virion population with an intact spacer, a phasmid is constructed that contains a second CRISPR cassette targeting a gene that is annotated as a virulence factor (mviN), as well as CRISPR arrays that contain multiple targeting spacers targeting Fn housekeeping genes. Such an optimization may improve the efficacy of eradication of particular target bacteria.

We will incorporate a CRISPR-cassette (promoter-repeat-spacer-repeat) in the phasmid backbone downstream of the origin of replication (ORI; see FIG. 9). The rationale for this approach is that if a homologous recombination event between the repeat sequences of the different CRISPR-cassettes occurs, each located upstream and downstream of the ORI, that would delete the ORI and shut down virion production derived from these phasmids. We expect that this approach will increase the likelihood that a homogenous virion population is maintained, and will further increase the overall efficiency of our system.

New phasmid variants are constructed by LCR as described above, Example 2, part E, yielding phasmid_fadA_mviN, and phasmid_multilocus. Virions derived from phasmid_fadA and the two newly constructed phasmids are tested for their ability to kill Fn in-vitro as described above, Example 2, part E. To measure the number of virion particles that are present in the supernatant, total DNA (n=6 per supernatant) is prepared from each supernatant fraction using standard approaches. By quantitative real-time PCR the number of phasmid copies present in the supernatant is determined based on standard curve analyses (BioRad, iCycler). The killing data of the different supernatants is normalized against the number of average phasmid copies present in the supernatant. At least three biological replicates are obtained, and the data analyzed by t-Test analyses (unpaired, two-tailed).

Intracellular delivery. A variety of bacterial pathogens, including Fn73, are intracellular pathogens. We expect that Fn killing will be most efficient if the antimicrobial is delivered by *L. reuteri* inside the cell. This can be achieved by expression of the *L. monocytogenes* internalin A (InlA) protein, as previously has been shown in *L. lactis* (Guimarães et al. *Microbes Infect* 2005, 7, 836-844). InlA complexes with E-cadherin, and mediates the invasion of *L. monocytogenes* in mammalian cells, including in solid breast tumor cells (van Pijkeren et al. *Hum. Gene Ther.* 2010, 21, 405-416). Colorectal cancer (CRC) cells are also of epithelial origin and express Ecadherin (Elzagheid et al. *World J Gastroenterol* 2006, 12, 4304-4309), which allows InlA-mediated invasion. For this example, an inlA derivative, inlAmurine, is integrated in the *L. reuteri* chromosome. Compared to InlA, InlAmurine has the amino acid changes S192N and Y369S. These amino acid changes result in increased invasion in mouse cells and human cells that can be attributed to increased binding affinity to the epithelial cell surface (Wollert et al. *Cell Regen* 2007, 129, 891-902). This is expected to maximize the number of *L. reuteri* cells that can accumulate in the tumor for subsequent virion release. To accomplish this, inlAmurine is first codon-optimize for expression in *L. reuteri*. The synthetic gene will be placed under the control or PHELP (Riedel et al. *Appl Environ Microbiol* 2007, 73, 3091-3094) for which we have demonstrated constitutive expression in *L. reuteri*. *L. reuteri* wild-type (negative control) and the strain expressing InlAmurine are assessed for their ability to enter Caco-2 colon cancer cells by a gentamicin-protection-assay (Elsinghorst, E. A. *Meth Enzymol* 1994, 236, 405-420; van Pijkeren et al. *Hum. Gene Ther.* 2010, 21, 405-416). As a positive control, *L. monocytogenes* EGDe is included. Three biological replicates will be carried out, each replicate consisting of three technical replicates. Statistical significant differences will be calculated by the Student t test (unpaired, two-tailed).

Temperature-dependent lysis. To fine tune the timing of lysis of the host bacterium, a temperature-induced lysis system will be used that is gradually activated when *L. reuteri* encounters body temperature (37° C.). For this purpose, a thermosensor is used that blocks translation at 30° C. while incubation at 37° C. yields graduate translation of the gene located downstream. In addition, a bacteriophage lysin cassette, consisting of a holin and lysin gene, is also incorporated. Our preliminary data shows that induction of the holin protein results in 90% lysis. Here, *L. reuteri* strains are constructed that contain the thermosensor combined with different bacteriophage lysins to identify a *L. reuteri* derivative that yields the most robust lysis in a gradual manner.

Figure 10:
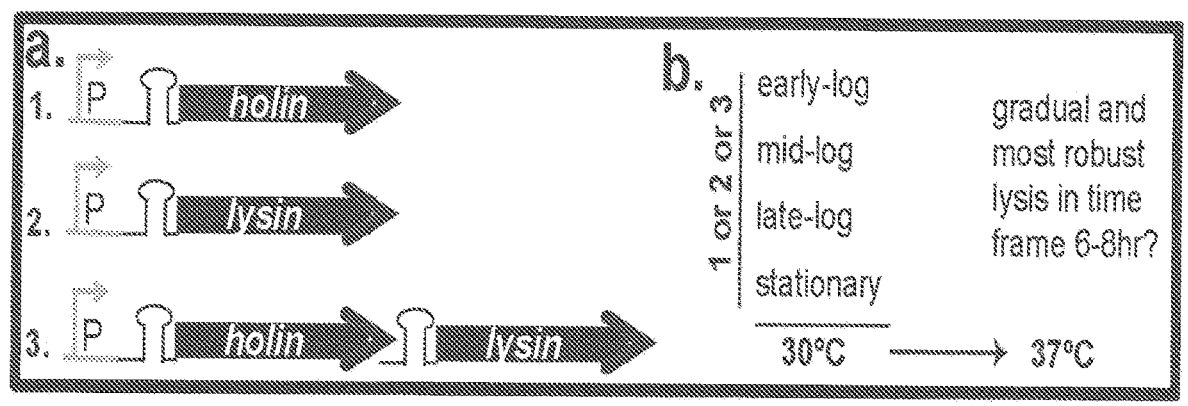
FIG. 10 provides an experimental overview of the *L. reuteri* delivery strains tested. Panel a shows fusion of a promoter (P) to a thermosensor (loop) and (a combination of) bacteriophage lysins; Panel b provides an overview of an experimental design to assess which strain combined with which growth phase yields most robust lysis at 37° C. at t=6-8 hr.

The constitutive *L. reuteri* mutL promoter, the U6 thermosensor (Neupert et al. *Nucleic Acids Research* 2008, 36, e124-e124) and the *L. reuteri* bacteriophage lysin (holin and/or lysin) are fused by LCR (de Kok et al. *ACS Synth. Biol.* 2014, 3, 97-106) (see, e.g., FIG. 10, Panel a). Well established methodologies are available for inserting gene cassettes in the *L. reuteri* chromosome. To assess which strain combined with which growth phase yields most robust lysis at 37° C. at t=6-8 hr, at the indicated growth phases, *L. reuteri* harboring construct 1, 2, or 3 are shifted from 30° C. to 37° C. and OD600 (Padmanabhan et al. *EJNMMI Research* 2013, 3, 60). Viability is assessed on an hourly basis. A minimum of three independent experiments are performed, followed by statistical analysis of the data (Student t test, two tailed, paired) (see, exemplary Panel b of FIG. 10).

Confirming and quantification of intracellular release. Antibiotic-induced bacterial lysis established for *L. monocytogenes* yielded release of bacterial extra-chromosomal molecules inside the eukaryotic cell (van Pijkeren et al. *Hum. Gene Ther.* 2010, 21, 405-416). This lysis has been further improved by extracellular lysin production. Prior to *L. reuteri* in-vivo experiments, lysis of *L. reuteri*, mediated by lysin production inside the bacterial cells, and release of extra-chromosomal molecules from *L. reuteri* in eukaryotic cells will be confirmed. The high-copy vector pNZ804881 is transformed to *L. reuteri* (LR), LR::inlAmurine, LR::inlAmurine::holin, LR::inlAmurine::lysin, and R::inlAmurine::holin::lysin. Bacteria are cultured at 30° C., and harvested at the growth phase for which we have established gradual and most robust lysis between 6-8 hours. A gentamycin-protection invasion assay is performed for 6, 7, and 8 hours. Eukaryotic cell lysates are prepared and examined for the number of viable *L. reuteri* by plate counts, while plasmid levels of pNZ8048 present in the eukaryotic lysate will be determine by quantitative real-time PCR. This will correlate the reduced bacterial viability with released extra-chromosomal molecules inside the eukaryotic cell. Replicates and statistics will be performed as described in the above subsection entitled Intracellular delivery.

Construction of *L. reuteri*ΔthyA::inlAmurine::lysin. The strain that displayed most robust lysis and release of extra-chromosomal molecules (determined according to the immediate above section) will be used as a template to delete the thyA gene by combining single-stranded DNA recombineering with CRISR-Cas selection (Oh et al. *Nucleic Acids Research* 2014, 42, e131-e131).

G. Determine the efficacy of biotherapeutic LR to eradicate Fn in APCmin/+ mice. Most human colorectal cancers are linked with a mutation in the tumor suppressor gene adenomatous polyposis coli (apc), which is considered a sentinel to regulate the progression of epithelial cells to the adenocarcinoma stage (for review, see Kinzler et al. *Cell Regen* 1996, 87, 159-170; Fodde, R. *Eur. J. Cancer* 2002, 38, 867-871). Mice with a nonsense mutation in the apc gene (C57BL/6-APCMin/+) display multiple intestinal neoplasia (Min) phenotype (Su et al. *Science* 1992, 256, 668-670) and serve as a model to study the development of colon cancer. Kostic et al. showed that C57BL/6-APCMin/+ mice developed significantly more colon tumors when the animals were fed Fn (*Cell Host & Microbe* 2013, 14, 207-215). We envision that successful delivery of CRISPR-guides to Fn by engineered virions will play a significant role in the prevention of Fn-induced colon tumor development. Using this mouse model and host bacteria of the invention comprising the bioengineered virions as described herein, strain-specific eradication of Fn will be shown to reduce the development of colon tumors in APCmin/+ mice, and reduces intratumor inflammation. For this purpose, the host bacteria comprising the bioengineered virions will be included in the drinking water of APCMin/+ mice two weeks after continuous Fn administration, followed by continuous administration of both the host bacteria comprising the bioengineered virions (biotherapeutic) and the pathogen. Following this experimental regime, colon (tumor) tissues are investigated for the bacterial load and inflammation.

Figure 11:
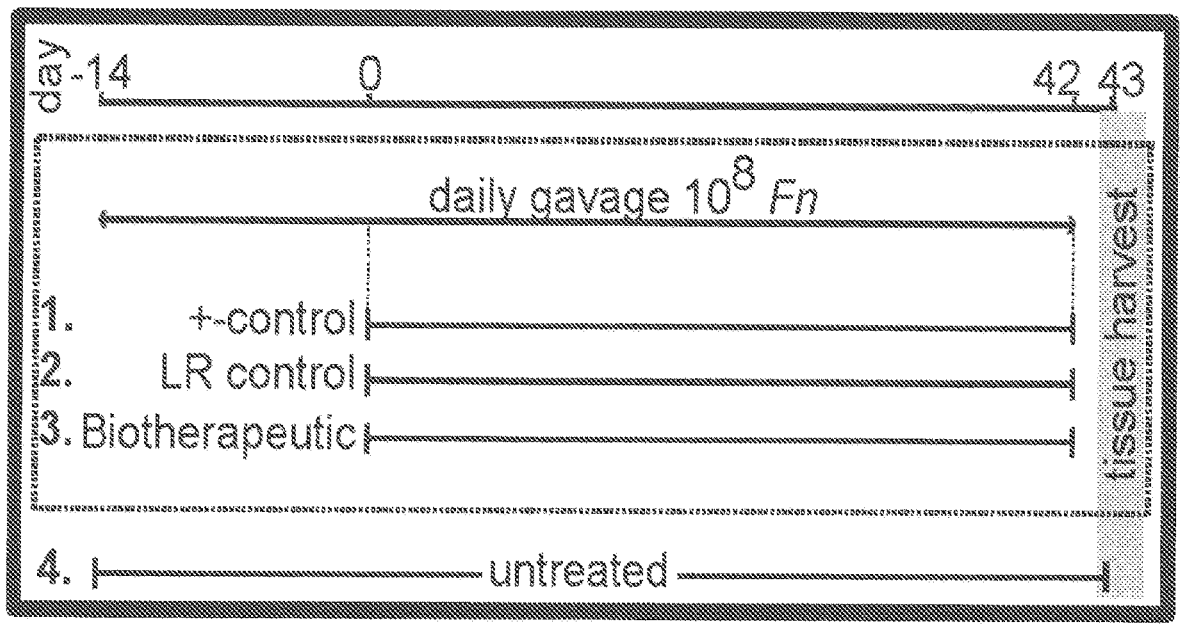
FIG. 11 provides an overview of the treatment groups and experimental design for C57BL/6J APCmin/+ mice and *Fusobacterium nucleatum* infection. Group 1: control (only Fn treatment); Group 2: LR::inlAmurine::lysin (LR control, which does contain thyA gene to maintain viability); Group 3: biotherapeutic producing virions targeting Fn; Group 4: untreated APCmin/+ mice.

Biotherapeutic treatment in APCmin/+ mice infected with Fn. A breeding pair C57BL/6J+/+ and C57BL/6J APCmin/+ is purchased, followed by in-house breeding under specific pathogen-free conditions. The APCmin/+ genotype will be determined by fecal genotyping, a reproducible non-invasive method (Erin L Symonds, *Biological Procedures Online* 2012, 14, 1 DOI: 10.1186/1480-9222-14-1). See FIG. 11 for the overview of the treatment groups, and the legend for details on the experimental design.

Thirty-six male C57BL/6J APCmin/+ mice (6 weeks old) are gavaged daily for eight weeks (days −14 to +42) with $10^8$ Fn21. At day 0, animals are split into three groups (12 animals per group as determined by PowerAnalysis (Faul et al. Behavior Research Methods 2009, 41, 1149-1160): f=0.67, α=0.05, Power=0.95, ANOVA, 2 measurements). Group 1: control (only Fn treatment); Group 2: LR::inlAmurine::lysin (LR control, which does contain thyA gene to maintain viability); Group 3: biotherapeutic producing virions targeting Fn; Group 4: untreated APCmin/+ mice. LR retains >90% viability in water (24 hours, room temperature; data not shown), and thus offers a convenient method to administrate LR (biotherapeutic) (Fåk et al. *PLoS ONE* 2012, 7, e46837-e46837). On average, it has been determined that C57BL/6J mice drink 8 ml/30 g body weight (Bachmanov et al. *Behav Genet* 2002, 32, 435-443), which combined with the weight of each animal, will enable us to supplement (biotherapeutic) *L. reuteri* to the drinking water to provide daily uptake of about $10^9$ (biotherapeutic) *L. reuteri*. At day 42, bacterial treatment(s) will be stopped for 24 hours prior to euthanasia. Bacterial loads of Fn and LR at day 43 represent bacteria that are host associated rather than passing through the system. Fecal pellets are collected on days −14 (i.e., 14 days prior to being provided the biotherapeutic), 0, and every day after until the end of the experiment (day +43). Drinking water is replaced daily. After euthanasia, the intestinal tract is removed, gently washed with PBS, and opened longitudinally. Sections of 4 cm are prepared corresponding to proximal, medial and distal regions of the small intestine. These regions and the colon are examined for tumors with a dissecting microscope by a blinded observer, and tumor sizes are reported. The experiment is repeated once to obtain two biological replicates.

Analyses of Collected Tissue/Fecal Material.

LR and Fn bacterial counts. Total DNA is extracted from fecal pellets (QiaAMP DNA stool mini kit) derived from the different time-points, followed by quantitative real-time PCR to determine the bacterial load (van Pijkeren et al. *Appl Environ Microbiol* 2006, 72, 4143-4153). This approach also allows enumeration of the number of Fn bacteria that have been killed by the host bacteria comprising the bioengineered virions (the biotherapeutic LR). This can be done by comparing Ct-values derived from reactions using a generic Fn oligonucleotide (representing total Fn levels) and an oligonucleotide that flanks the Cas-nuclease target site fadA (representing surviving Fn levels). The difference can be accounted for by the number of Fn cells that are killed. LR (biotherapeutic) that has been supplemented to the drinking water is also enumerate from fecal pellets both by culturing and by qRT-PCR. Oligonucleotides that amplify a region of the reuterin cluster that is unique to human LR strains are used (Spinler et al. *Genome Biol Evol* 2014 DOI: 10.1093/gbe/evu137.). The same oligonucleotides are used to verify that the obtained colonies are (biotherapeutic) LR. Half of the colon tumors that are harvested are also subjected to bacterial enumeration by qRT-PCR. Total DNA is extracted in an identical manner as previously described (Kostic et al. *Cell Host* & *Microbe* 2013, 14, 207-215).

Colon-tumor microbiota analyses. LR 6475 changes the GI microbiota composition (Britton et al. *J Cell Physiol* 2014, 229). To investigate the effect of biotherapeutic LR supplementation on the microbial colon-tumor microbiota, 16S metagenomic libraries of the V3/V4 region of the 16S rRNA gene are prepared. Library construction, sequencing, and analyses of the data is performed as described in the 16S Metagenomic Sequencing Library Preparation Protocol Part #15044223 Rev. B (Illumina Inc., San Diego, Calif., USA). The V3/V4 variable region will be amplified with nested primers. Region specific primers (Klindworth et al. *Nucleic Acids Research* 2013, 41, e1-e1) are modified to add Illumina adapter overhang nucleotide sequences to the gene-specific sequences. After initial amplification, the library size is verified and cleaned, followed by addition of Illumina dual indexes and Sequencing adapters. Quality and quantity of the finished libraries are assessed using an Agilent DNA1000 chip and Qubit dsDNA HS Assay kit, respectively. Libraries are standardized to 2 μM and pooled prior to sequencing. Paired end, 250 bp sequencing is performed using the Illumina MiSeq Sequencer and a MiSeq 500 bp (v2) sequencing cartridge. Images are analyzed using the standard Illumina Pipeline, version 1.8.2. OUT assignments, and diversity plots will be created using QIIME analysis pipeline (Caporaso et al. *Nat Meth* 2010, 7, 335-336).

Cytokine analysis. Tumors infected with Fn show increased expression of proinflammatory genes in both murine and human tissue, which in mice is most pronounced in colon tumors (Kostic et al. *Cell Host* & *Microbe* 2013, 14, 207-215). The effect of biotherapeutic-induced eradication of Fn on the colon tumor cytokine profile is determined by focusing initially on proinflammatory cytokines that were previously shown to be differentially expressed. These include: ptgs2, skyb, interleukin-6, tnf, and mmp3. For a broader screen, the cDNA from the different tumors will also be subjected to an Inflammatory Cytokines & Receptors PCR Array (Qiagen) that includes 84 key genes that mediate an inflammatory response.

To prevent the possibility of Fn naturally mutating and inactivating its native cas gene thereby resulting in resistance to the biotherapeutic LR, the LR that secretes an endolysin targeting Fn can be combined with LR that secretes small peptides that are known to inhibit Fn invasion (Rubinstein et al. *Cell Host* & *Microbe* 2013, 14, 195-206).

Example 3

Gastrointestinal inflammation, including those caused by enteric pathogens such as *E. coli* and *H. pylori*, and abnormal gut microbiota composition play important roles in the development of environmental enteric dysfunction (EED), a condition that is widespread in children and adults in low- and middle-income countries. Increased understanding of the role of select microbes in EED etiology, combined with a key role for the gastrointestinal (GI) microbiota as a whole to maintain human health, has created a conundrum in health care. As of today, antibiotics are the primary line of treatment to eradicate bacterial pathogens. Yet, application of antibiotics results in major perturbations of the GI microbiota. These perturbations, especially in early life, have been correlated with long-lasting metabolic changes leading to, for example, allergic asthma. In addition, historical overuse of antibiotics in both agriculture and healthcare has led to the emergence of microbial antibiotic resistance, a major health threat in $21^{st}$ century medicine.

In a further embodiment of the invention, a host bacterium, probiotic *Lactobacillus reuteri* (LR), is engineered to comprise a recombinant phasmid comprising a CRISPR guide that targets the bacterium *Heliobacter pylori* to yield a transcript that together with native Cas, causes self-destruction of the target bacterium (FIG. 1).

The probiotic strain that is used as a delivery-platform, *Lactobacillus reuteri* 6475, survives passage through the human and mouse GI tract, is genetically amenable, and has an intrinsically low mutation-rate. In addition, this probiotic platform is ideal to be exploited as a delivery vehicle in EED since this LR strain has anti-inflammatory properties and ameliorates infection by pathogenic *E. coli*, both known contributors to EED.

*Helicobacter pylori* (HP), a Gram-negative pathogen whose presence is linked to the development of EED, is a target bacterium. Several bacteriophages have been identified that infect HP, and bioinformatics analyses revealed that the CRISPR-Cas system is conserved in HP, which can be exploited here for self-killing upon delivery of the CRISPR by the engineered virions. A phasmid is engineered (as outlined in FIG. 1) in which the bacteriophage DNA of KHP30 is incorporated. KHP30 infects >60% of HP clinical isolates. A CRISPR-array is incorporated targeting the HP housekeeping gene gyrA. Plasmid-induced expression of the holin gene will release the virions for subsequent testing.

In some embodiments, the LR is engineered for optimal temperature-dependent lysis driven from chromosomal expressed genes for subsequent efficient release of the engineered virions as described above. To optimize targeting efficacy, a phasmid that encodes multiple CRISPRs is designed. Biological safety may be enhanced by making a LR-derivative that is sensitive to vancomycin, and genes encoding adhesins can be deleted to prevent colonization in the host. Efficacy of our biotherapeutic platform are assessed in-vivo. Because bacteriophages have been identified for the vast majority of bacterial targets, including those that have been proposed to play a role in the development of EED, combined with the fact that many bacteria encode a CRISPR-Cas system, the invention can be expanded to target other bacteria, including those that are notorious antimicrobial resistant bacteria. Further for those bacterial targets that do not comprise an endogenous CRISPR-Cas system, a heterologous system can be introduced in a host bacterium of this invention.

That which is claimed is:

1. A host bacterium comprising a recombinant phasmid, the recombinant phasmid comprising: (a) an origin of replication for a plasmid, (b) a genome from a bacteriophage of a target bacterium, wherein the bacteriophage genome does not include the bacteriophage replication and lysis modules, and (c) at least one CRISPR RNA (crRNA) comprising (i) a repeat sequence, having a 5' end and a 3' end, and (ii) a spacer-repeat sequence, having a 5' end and a 3' end, and the repeat sequence is linked at its 3' end to the 5' end of the spacer-repeat sequence, wherein the spacer is at least 70% complementary to a nucleic acid of the target bacterium.

2. The host bacterium of claim 1, wherein the at least one crRNA comprises two or more spacer-repeat sequences.

3. The host bacterium of claim 2, wherein the spacers of the two or more spacer-repeat sequences are each separately at least 70% identical to the same or a different region of the genome of the target bacterium or to a region of the genome of a different target bacterium.

4. The host bacterium of claim 1, wherein the host bacterium can survive in the digestive system, the mouth, the epidermis, conjunctiva, respiratory tract, and/or the urogenital tract of an animal body.

5. The host bacterium of claim 1, wherein the host bacterium is a lactic acid bacterium.

6. The host bacterium of claim 1, wherein the host bacterium is *Lactobacillus* spp., *Lactococcus* spp., or *Streptococcus* spp.

7. The host bacterium of claim 1, wherein the target bacterium is *Clostridium difficile, Escherichia coli, Clostridium tetani, Helicobacter pylori, Fusobacterium nucleatum, Gardnerella vaginitis, Porphyromonas gingivalis, Aggregatibacter actinomycetemcomitans, Listeria monocytogenes, Staphylococcus aureus, Campylobacter jejuni, Vibrio vulnificus, Salmonella typhi, Clostridium botulinum, Mycobacterium tuberculosis, Mycobacterium leprae, Mycobacterium lepromatosis, Corynebacterium diptheriae, Klebsiella pneumoniae, Acinetobacter baumannii, Streptococcus mutans*, group B streptococci, including but not limited to, *Staphylococcus aureus, Streptococcus agalactiae, Streptococcus pneumonia, Enterococcus* spp. including, but not limited to, *Enterococcus faecalis*.

8. The host bacterium of claim 1, wherein the crRNA is a Type I, Type II, Type III or Type V crRNA.

9. The host bacterium of claim 1, wherein the crRNA is a Type II crRNA and the phasmid further comprises a trans-activating CRISPR (tracr) sequence fused to the crRNA to form a single guide RNA (sgRNA).

10. The host bacterium of claim 1, wherein the crRNA is a Type II crRNA and the phasmid further comprises a trans-activating CRISPR (tracr) sequence and a nucleic acid encoding a Cas9 polypeptide.

11. The host bacterium of claim 9, wherein the phasmid further comprises a nucleic acid encoding a Cas9 polypeptide.

12. The host bacterium of claim 1, wherein the crRNA is a Type I crRNA.

13. The host bacterium of claim 12, wherein the crRNA is a synthetic Type I processed guide RNA.

14. The host bacterium of claim 12, wherein the phasmid further comprises a nucleic acid encoding a Type I CRISPR-Cas polypeptide and Type I Cascade polypeptides.

15. The host bacterium of claim 1, wherein the genome of the host bacterium is modified to provide lysis of the host bacterium.

16. The host bacterium of claim 15, wherein the host bacterium comprises in its genome a heterologous nucleic acid operably linked to a promoter and encoding a holin polypeptide and an endolysin polypeptide.

17. The host bacterium of claim 16, wherein lysis of the host bacterium is inducible by temperature or by the presence of an inducer molecule.

18. The host bacterium of claim 1, wherein the genome of the host bacterium is modified, the modification resulting in the host bacterium being auxotrophic for at least one compound required for its growth.

19. The host bacterium of claim 18, wherein the phasmid comprises a nucleic acid that when expressed complements the auxotrophy of the host bacterium.

20. The host bacterium of claim 1, wherein the genome of the host bacterium is modified to comprise a nucleic acid encoding internalin.

21. A method of treating a bacterial infection in a subject in need thereof, comprising administering to the subject a therapeutically effective amount of the host bacteria of claim 1, thereby treating the bacterial infection.

22. A method of killing a target bacterial genus, species or strain, comprising contacting the target bacterial genus, species or strain with the host bacterium of claim 1, thereby killing the bacterial species.

* * * * *

SEQUENCE LISTING

<160> NUMBER OF SEQ ID NOS: 14

<210> SEQ ID NO 1
<211> LENGTH: 30
<212> TYPE: DNA
<213> ORGANISM: Fusobacterium nucleatum

<400> SEQUENCE: 1
atgaactaaa aacttgaaaa gttttgaaat         30

<210> SEQ ID NO 2
<211> LENGTH: 30
<212> TYPE: DNA
<213> ORGANISM: Fusobacterium nucleatum

<400> SEQUENCE: 2
atttaaattc taatatagaa atacataaat         30

<210> SEQ ID NO 3
<211> LENGTH: 30
<212> TYPE: DNA
<213> ORGANISM: Fusobacterium nucleatum

<400> SEQUENCE: 3
atttatgtat ttctatatta gaatttaaat         30

<210> SEQ ID NO 4
<211> LENGTH: 36
<212> TYPE: DNA
<213> ORGANISM: Fusobacterium nucleatum

<400> SEQUENCE: 4
gtttgagagt aatgttattt taaatagatt caaaac         36

<210> SEQ ID NO 5
<211> LENGTH: 30
<212> TYPE: DNA
<213> ORGANISM: Fusobacterium nucleatum

<400> SEQUENCE: 5
atgaactgta aacttgaaaa gttttgaaat         30

<210> SEQ ID NO 6
<211> LENGTH: 10
<212> TYPE: DNA
<213> ORGANISM: Artificial
<220> FEATURE:
<223> OTHER INFORMATION: typical CRISPR-Cas repeat sequence

<400> SEQUENCE: 6
gttttagagc         10

<210> SEQ ID NO 7
<211> LENGTH: 13
<212> TYPE: DNA
<213> ORGANISM: Artificial
<220> FEATURE:
<223> OTHER INFORMATION: typical CRISPR-Cas repeat spacer sequence

<400> SEQUENCE: 7
ttcaaaactt taa         13

```
<210> SEQ ID NO 8
<211> LENGTH: 14
<212> TYPE: DNA
<213> ORGANISM: Artificial
<220> FEATURE:
<223> OTHER INFORMATION: typical CRISPR-Cas repeat spacer sequence

<400> SEQUENCE: 8
cctgtgtttt agag                                                      14

<210> SEQ ID NO 9
<211> LENGTH: 10
<212> TYPE: DNA
<213> ORGANISM: Artificial
<220> FEATURE:
<223> OTHER INFORMATION: typical CRISPR-Cas repeat sequence

<400> SEQUENCE: 9
gttccaaaac                                                           10

<210> SEQ ID NO 10
<211> LENGTH: 30
<212> TYPE: DNA
<213> ORGANISM: Fusobacterium nucleatum

<400> SEQUENCE: 10
atgaactaaa aacttgaaaa gttttgaaat                                     30

<210> SEQ ID NO 11
<211> LENGTH: 30
<212> TYPE: DNA
<213> ORGANISM: Fusobacterium nucleatum

<400> SEQUENCE: 11
atttaaattc taatatagaa atacataaat                                     30

<210> SEQ ID NO 12
<211> LENGTH: 30
<212> TYPE: DNA
<213> ORGANISM: Fusobacterium nucleatum

<400> SEQUENCE: 12
atttatgtat ttctatatta gaatttaaat                                     30

<210> SEQ ID NO 13
<211> LENGTH: 36
<212> TYPE: DNA
<213> ORGANISM: Fusobacterium nucleatum

<400> SEQUENCE: 13
gtttgagagt aatgttattt taaatagatt caaaac                              36

<210> SEQ ID NO 14
<211> LENGTH: 30
<212> TYPE: DNA
<213> ORGANISM: Fusobacterium nucleatum

<400> SEQUENCE: 14
atgaactgta aacttgaaaa gttttgaaat                                     30
```